US005733878A

United States Patent [19]
Kuberasampath et al.

[11] Patent Number: 5,733,878
[45] Date of Patent: Mar. 31, 1998

[54] MORPHOGEN-INDUCED PERIODONTAL TISSUE REGENERATION

[75] Inventors: Thangavel Kuberasampath, Medway; David C. Rueger, Hopkinton; Hermann Oppermann; Charles M. Cohen, both of Medway, all of Mass.; Roy H. L. Pang, Etna, N.H.

[73] Assignee: Creative BioMolecules, Inc., Hopkinton, Mass.

[21] Appl. No.: 643,763

[22] Filed: May 6, 1996

Related U.S. Application Data

[63] Continuation of Ser. No. 155,343, Nov. 15, 1993, Pat. No. 5,656,593, which is a continuation of Ser. No. 945,285, Sep. 15, 1992, abandoned, which is a continuation-in-part of Ser. No. 938,336, Aug. 28, 1992, abandoned, Ser. No. 938,337, Aug. 28, 1992, abandoned, Ser. No. 753,059, Aug. 30, 1991, abandoned, and Ser. No. 752,764, Aug. 30, 1991, abandoned, which is a continuation-in-part of Ser. No. 667,274, Mar. 11, 1991, abandoned, said Ser. No. 753,059, is a continuation-in-part of Ser. No. 667,274.

[51] Int. Cl.[6] ............ A61K 38/18; A61K 38/17; C07K 14/51
[52] U.S. Cl. .................. 514/12; 514/21; 530/350
[58] Field of Search ............... 435/1, 2; 514/2, 514/12, 21, 900, 902, 944; 424/48, 49; 530/350

[56] References Cited

U.S. PATENT DOCUMENTS

| | | | |
|---|---|---|---|
| 4,725,234 | 2/1988 | Ethridge | 433/215 |
| 4,877,864 | 10/1989 | Wang et al. | 514/12 |
| 4,919,939 | 4/1990 | Baker | 424/493 |
| 4,968,590 | 11/1990 | Kuberasampath et al. | 530/326 |
| 4,975,526 | 12/1990 | Kuberasampath et al. | 530/350 |
| 5,011,691 | 4/1991 | Oppermann et al. | 424/423 |
| 5,013,649 | 5/1991 | Wang et al. | 435/69.1 |
| 5,106,626 | 4/1992 | Parsons et al. | 424/423 |
| 5,108,753 | 4/1992 | Kuberasampath et al. | 424/422 |
| 5,141,905 | 8/1992 | Rosen et al. | 435/69.1 |
| 5,368,859 | 11/1994 | Dunn et al. | 424/426 |
| 5,455,041 | 10/1995 | Genco et al. | 424/435 |
| 5,459,047 | 10/1995 | Wozney et al. | 435/69.1 |

FOREIGN PATENT DOCUMENTS

| | | |
|---|---|---|
| 0148155 | 7/1985 | European Pat. Off. . |
| 0416578 | 3/1991 | European Pat. Off. . |
| 0495284 | 7/1992 | European Pat. Off. . |
| 88/00205 | 1/1988 | WIPO . |
| 89/09787 | 10/1989 | WIPO . |
| 89/09788 | 10/1989 | WIPO . |
| 89/10409 | 11/1989 | WIPO . |
| 90/03733 | 4/1990 | WIPO . |
| 90/10017 | 9/1990 | WIPO . |
| 92/15323 | 9/1992 | WIPO . |
| 93/00432 | 1/1993 | WIPO . |
| 93/09229 | 5/1993 | WIPO . |
| 95/24210 | 9/1995 | WIPO . |
| 95/24474 | 9/1995 | WIPO . |
| 95/33830 | 12/1995 | WIPO . |

OTHER PUBLICATIONS

Sampath et al. (1983), "Homology of Bone–Inductive Proteins From Human, Monkey, Bovine, and Rat Extracellular Matrix," *Proc. Natl. Acad. Sci. USA* 80:6591–6595.

Mason (1985), "Complementary DNA Sequences of Ovarian Follicular Fluid Inhibin Show Precursor Structure and Homology with Transforming Growth Factor–β," *Nature* 318:659–663.

Cate et al. (1986), "Isolation of the Bovine and Human Genes for Mullerian Inhibiting Substance and Expression of the Human Gene in Animal Cells," *Cell* 45:685–698.

Miller et al. (1987), "Phenotypic Modulation of the Swarm Rat Chondrosarcoma Induced by Morphogenetic Bone Matrix," *Cancer Research* 42:3589–3594.

Badgett et al. (1987), "A Transcript from a Drosophila Pattern Gene Predicts a Protein Homologous to the Transforming Growth Factor–β Family," *Nature* 325:81–84.

Weeks et al. (1987), "A Maternal mRNA Localized to the Vegetal Hemisphere Xenopus Eggs Codes for a Growth Factor Related to TGF–β," *Cell* 51:861–867.

Rosen et al.; Wozney et al.; Wang et al. (1988) *Calcified Tissue International* 42 (Suppl.): A35 (Abstr. No. 136); A37 (Abstr. No. 146 and 147).

Wang et al. (1988), "Purification and Characterization of Other Distinct Bone–Inducing Factors," *Proc. Natl. Acad. Sci. USA* 85:9484–9488.

Wozney et al. (1988), "Novel Regulators of Bone Formation: Molecular Clones and Activities," *Science* 242:1528–1533.

Dahlin et al. (1989), "Generation of New Bone Around Titanium Implants Using A Membrane Technique: An Experimental Study in Rabbits," 4 *Int. J. Oral Maxillofac. Implants* 19–25.

Lyons (1989), "VGR–1, A Mammalian Gene Related to Xenopus VG–1, is a member of the Transforming Growth Factor Beta Gene Superfamily", *Proc. Nat. Acad. Sciences* 86:4554–4558.

Lyons et al. (1989), "Patterns of Expression of Murine VGR–1 and BMP–2a RNA Suggest That Transforming Growth Factor–β–Like Genes Coordinately Regulate Aspects of Embryonic Development," *Genes & Development* 3:1657–1668.

Mason et al. (1989), "Activin B: Precursor Sequences, Genomic Structure and in Vitro Activities," *Molecular Endocrinology* 3 (No. 9):1352–1358.

Rosen et al. (1989), "Purification and Molecular Cloning of a Novel Group of BMPs and Localization of BMP mRNA in Developing Bone," 20 *Conn. Tissue Res.* 313–319.

(List continued on next page.)

*Primary Examiner*—Nancy Degen
*Attorney, Agent, or Firm*—Testa, Hurwitz & Thibeault, LLP

[57] ABSTRACT

Disclosed are methods and compositions for inducing periodontal tissue morphogenesis in a mammal which include a therapeutically effective concentration of a morphogen. The methods and compositions are useful for integrating an implanted tooth in a tooth socket and for inhibiting tissue loss associated with periodontal disease or injury.

54 Claims, 2 Drawing Sheets

OTHER PUBLICATIONS

Behringer et al. (1990), "Abnormal Sexual Development in Transgenic Mice Chronically Expressing Mullerian Inhibiting Substance," *Nature* 345:167–170.

Celeste et al. (1990), "Identification of Transforming Growth Factor Beta Family Members Present in Bone–Inductive Protein Purified from Bovine Bone," *Proc. Nat. Acad. Sciences* 87:9843–9847.

Green et al. (1990), "Graded Changes in Dose of a Xenopus Activin A Homologue Elicit Stepwise Transitions in Embryonic Cell Fate," *Nature* 347:391–394.

Katagiri et al. (1990), "The Non–Osteogenic Mouse Pluripotent Cell Line, C3H10T1/2, Is Induced to Differentiate Into Osteoblastic Cells By Recombinant Human Bone Morphogenetic Protein–2," *Biochem. Biophys. Res. Comm* 172:1:295–299.

Lee (1990), "Identification of a Novel Member (GDF–1) of the Transforming Growth Factor–$\beta$ Superfamily," *Molecular Endocrinology* 4 (No. 7):1034–1040.

Nakashima (1990), "The Induction of Reparative Dentine In The Amputated Dental Pulp of the Dog By Bone Morphogenetic Protein," 35 *Arch. Oral Biol.* 7:493–497.

Ozkaynak et al. (1990), "OP–1 cDNA Encodes an Osteogenic Protein in the TGF–$\beta$ Family," *EMBO J.* 9 (No. 7):2085–2093.

Panaganiban et al. (1990), "Biochemical Characterization of the *Drosophila dpp* Protein, a Member of the Transforming Growth Factor $\beta$ Family of Growth Factors," *Molecular and Cellular Biology* 10, (No. 6) 2669–2677.

Rosen et al.; Celeste et al. (1990), *J. Cell. Biochem.*; Supplement 14E 33 (Abstr. No. 0–004); 54 (Abstr No. 0–105).

Sampath et al. (1990), "Bovine Osteogenic Protein Is Composed of Dimers of OP–1 and BMP–2A, Two Members of the Transforming Growth Factor–$\beta$ Superfamily," *J. Biol. Chem.* 265:13198–13205.

Schubert et al. (1990), "Activin is a Nerve Cell Survival Molecule," *Nature* 344:868–870.

Smith et al. (1990), "Identification of a Potent Xenopus Mesoderm Inducing Factor as a Homologue of Activin A," *Nature* 345:729–731.

Smith et al. (1990), "In vivo Morphogenetic Activity of Dentine Matrix Proteins," 18 *J. Biol. Buccale*:123–129.

Smith et al. (1990), "Preliminary Studies on the in vivo Morphogenetic Properties of Dentine Matrix Proteins," 11 *Biomaterials*.

Sokol et al. (1990), "A Mouse Macrophage Factor Induces Head Structures and Organizes a Body Axis in Xenopus," *Science* 249:561–563.

Wang et al. (1990), "Recombinant Human Bone Morphogenetic Protein Induces Bone Formation," *Proc. Natl. Acad. Sci. USA* 87:2220–2224.

Wozney et al. (1990), "Growth Factors Influencing Bone Development," *J. Cell Sci.* Suppl. 13:149–156.

Wozney (1990), "Bone Morphogenic Proteins," 1 *Prog. In Growth Factor Res.* 267–280.

Yannas (1990), "Biologically Active Analogues of the Extracellular Matrix: Artificial Skin and Nerves," *Angew. Chem. Int. Ed. Engl.* 29:20–35.

Caplan (1991), "Mesenchymal Stem Cells," *J. Orthop. Res.* 9:641–650.

Chen et al. (1991), "Bone Morphogenetic Protein–2b Stimulation of Growth and Osteogenic Phenotypes in Rat Osteoblast–like Cells: Comparison with TGF–$\beta$," *J. Bone Min. Res.* 6:1387–1393.

D'Allessandro et al. (1991), *J. Cell Biochem.* Suppl. 15F (Abstr. No. 105).

Israel et al. (1991),Abstract Q–111 *J. Cell Biochem. Suppl.*

Lee (1991), "Expression of Growth/Differentiation Factor 1 in the Nervous System: Conservation of a Bicistronic Structure," *Proc. Natl. Acad. Sci. USA* 88:4250–4254.

Ozkaynak et al. (1991), "Murine Osteogenic Protein (OP–1): High Levels of mRNA in Kidney," *Biochem. Biophys. Res. Comm.* 179:116–123.

Takuwa et al. (1991), "Bone Morphogenetic Protein–2 Stimulates Alkaline Phosphatase Activity and Collagen Synthesis In Cultured Osteoblastic Cells, MC3T3–E1," *Biochem. Biophys. Res. Comm.* 174:1; 96–101.

Wharton et al. (1991), "Drosophilia 60A Gene, Another Transforming Growth Factor $\beta$ Family Member, is Closely Related to Human Bone Morphogenetic Proteins," *Proc. Natl. Acad. Sci. USA* 88:9214–9218.

Yamaguchi et al. (1991), "Recombinant Human Bone Morphogenetic Protein–2 Stimulates Osteoblastic Maturation and Inhibits Myogenic Differentiation In Vitro," *J. Cell. Biol.* 113:681–687.

Israel et al. (1992), "Expression and Characterization of Bone Morphogenetic Protein–2 in Chinese Hamster Ovary Cells," *Growth Factors* 7:139–150.

Rogers et al. (1992), "Bone Morphogenetic Proteins–2 and –4 are Involved in the Retinoic Acid–Induced Differentiation of Embryonal Carcinoma Cells," *Mol. Biol. Cell* 3:2; 189–196.

Thesleff (1995), "Homeobox Genes and Growth Factors In Regulation of Craniofacial and Tooth Morphogenesis," 53 *Acta Odontol. Scand.* 129–134.

Tureckova et al. (1995), "Comparison of Expression of the msx–1, msx–2, BMP–2 and BMP–4 Genes in the Mouse Upper Diastemal and Molar Tooth Primordia," 39 *Int. J. Dev. Biol.* 459–468.

Thesleff et al. 1995), "Regulation of organogenesis. Common molecular mechanisms regulating the development of teeth and other organs," 39 *Int. J. Dev. Biol.* 35–50.

Vaahtokari et al. (1996), "The enamel knot as a signaling center in the developing mouse tooth," 54 *Mechanisms of Development* 39–43.

MORPHOGEN-INDUCED PERIODONTAL TISSUE REGENERATION

CROSS-REFERENCE TO RELATED APPLICATIONS

This application is a continuation of U.S. Ser. No. 08/155,343, filed Nov. 15, 1993, now U.S. Pat. No. 5,656,593, which is a continuation of U.S. Ser. No. 07/945,285, filed Sep. 15, 1992, now abandoned which is a continuation-in-part of (1) U.S. Ser. No. 07/938,336, filed Aug. 28, 1992, now abandoned, and U.S. Ser. No. 07/938,337, now abandoned, filed Aug. 28, 1992 and U.S. Ser. No. 07/753,059, filed Aug. 30, 1991, now abandoned, which is a continuation-in-part of U.S. Ser. No. 07/667,274, filed Mar. 11, 1991, now abandoned, and (2) U.S. Ser. No. 07/752,764, filed Aug. 30, 1991, now abandoned, which is a continuation-in-part of U.S. Ser. No. 07/667,274, filed Aug. 11, 1991, now abandoned. The disclosures of these applications are incorporated herein by reference.

BACKGROUND OF THE INVENTION

This invention relates generally to the dental arts and more specifically to methods and compositions for treating and regenerating periodontal tissue.

The peridontium is the cushioning tissue which anchors the tooth root to the mandibular or maxillar jawbone tissue by suspending the tooth in the tooth socket ("alveolus"). Periodontal tissue includes both the periodontal ligament, a collagen-containing tissue that is in contact with the bone tissue, and cementum, a mineralized tissue that covers the dental root surface. These two hard tissues are connected through the periodontal ligament fibers that run in a perpendicular direction to the two surfaces and thereby serve to anchor and suspend the tooth in the tooth socket, providing a shock-absorptive cushion between the tooth and the jawbone that accommodates the pressure applied to teeth when food is being chewed.

Periodontal tissue loss may occur as a result of disease, including infectious diseases (e.g., gingivitis, caused by bacteria), nutritional diseases, e.g., scurvy, resulting from a vitamin deficiency, and a number of neoplastic diseases, including acute leukemia and lymphomas. The diseases are characterized by inflammation, bleeding and ulceration. Periodontal disease also may result from an opportunistic infection, e.g., in an immune-compromised individual. Left untreated, these diseases can cause significant periodontal tissue loss which loosen the tooth and ultimately can result in loss of the tooth and the alveolar bone tissue (periodontitis.) Chronic periodontitis is the primary cause of tooth loss in adults. Current treatments include professional cleaning to remove plaque and tartar, use of oral antiseptics, local and/or systemic antibiotic therapies, and/or surgical procedures to remove periodontal pockets formed from periodontal tissue lesions and necrosis. Typically, where a tooth has been lost as a result of periodontitis, a prosthetic tooth or removable bridge is substituted for the natural tooth.

Periodontal tissue loss also may occur as a result of mechanical injury to the tissue or to the tooth itself, particularly one causing tooth loss. Tooth loss also may occur as a result of any of a number of dental diseases, e.g., dental caries, pulpitis, or osteomyelitis.

A viable tooth can be reimplanted if implantation occurs quickly after loss, e.g., within thirty minutes, and if the periodontal tissue within the tooth socket is still healthy. However, if a significant period of time is allowed to elapse, the living periodontal tissue lining the tooth socket will be resorbed. In addition, the tooth itself begins to degenerate and a prosthetic tooth or removable bridge must be implanted. In the absence of healthy periodontal tissue the prosthetic implant is integrated directly into the jaw bone tissue in a condition called ankylosis (bone tissue in direct contact with dentin tissue.) The life of such prosthetic tooth implants often is limited due to the absence of viable periodontal tissue to enhance tooth anchoring and to absorb the impact of mastication on the prosthesis.

It is an object of this invention to provide a means for inhibiting periodontal tissue loss, as well as means for inducing regeneration of damaged periodontal tissue. Another object is to provide means for inhibiting the periodontal tissue damage and tooth loss associated with periodontal and other gum diseases. Yet another object is to enhance integration of an implanted tooth, including a reimplanted natural tooth or tooth prosthesis, in the tooth socket. Still another object is to promote periodontal tissue growth around an implanted tooth. Another object is to inhibit ankylosis of an implanted tooth or tooth prosthesis.

These and other objects and features of the invention will be obvious from the specification, drawings and claims, which follow.

SUMMARY OF THE INVENTION

The invention provides methods and compositions for inhibiting periodontal tissue loss in a mammal, particularly humans, including regenerating damaged tissue and/or inhibiting additional damage thereto. The methods and compositions of this invention may be used to prevent and/or inhibit tooth loss, as well as to enhance integration of an implanted tooth.

As used herein, "implanted tooth" includes a natural tooth which has grown naturally in the tooth socket, a natural tooth which is reimplanted in a tooth socket, and a prosthetic tooth, which includes both natural teeth from which the root has been removed and replaced with an inert, biocompatible material, and "complete" prostheses made of natural or synthetic, non dentin-containing materials. In all cases, "tooth" refers to a natural or synthetic composition essentially defining the shape of a natural tooth, having a solid tooth body, including a crown and tooth root. "Reimplanted natural tooth" includes both an allogenic tooth, e.g., selected from a tooth bank; and a tooth autologous to the mammal, such as a tooth which has fallen out, been knocked out, or otherwise removed from the individual into which it is now being reimplanted. "Integrated tooth" means an implanted tooth with a living, substantially healthy periodontal tissue, including periodontal ligament and cementum, anchoring the tooth to the jaw bone. "Viable" tissue means living, substantially healthy tissue. "Viable tooth" refers to an implanted natural tooth with a living tooth root. "Periodontium" defines the tissues which surround the tooth in the tooth socket and includes both periodontal ligament and cementum. "Inhibit loss" of periodontal tissue, as used herein, means inhibiting damage to, and/or loss of, periodontal tissue, including periodontal ligament and/or cementum, and includes regenerating lost or damaged tissue and/or inhibiting additional damage thereto. "Symptom alleviating cofactor" refers to one or more pharmaceuticals which may be administered together with the therapeutic agents of this invention and which alleviate or mitigate one or more of the symptoms typically associated with periodontal tissue loss. Exemplary cofactors include antibiotics, antiseptics, non-steroidal antiinflammatory agents, anaesthetics and analgesics.

The methods and compositions of this invention include a morphogenic protein ("morphogen"), as described herein, which, when provided to the tooth and/or jawbone surfaces in a tooth socket is capable of inducing periodontal tissue formation where periodontal tissue has been lost or damaged, and enhancing integration of an implanted tooth thereby.

In one aspect, the invention features therapeutic treatment methods and compositions for inhibiting periodontal tissue loss in a mammal which include administering to the individual a therapeutically effective morphogen concentration and for a time sufficient to regenerate damaged periodontal tissue and/or to inhibit additional damage thereto.

In another aspect, the invention features therapeutic treatment methods and compositions for inhibiting periodontal tissue loss in a mammal which include administering to the individual a compound that stimulates in vivo a therapeutically effective concentration of an endogenous morphogen in the body of the mammal sufficient to regenerate damaged periodontal tissue and/or to inhibit additional damage thereto. These compounds are referred to herein as morphogen-stimulating agents, and are understood to include substances which, when administered to a mammal, act on cells of tissue(s) or organ(s) that normally are responsible for, or capable of, producing a morphogen and/or secreting a morphogen, and which cause the endogenous level of the morphogen to be altered. The agent may act, for example, by stimulating expression and/or secretion of an endogenous morphogen. In preferred embodiments, the agent stimulates expression and/or secretion of an endogenous morphogen so as to increase amounts of the morphogen in the alveolar bone, periodontium or cementum tissue cells.

In another aspect, the invention provides methods and compositions for enhancing the integration of an implanted tooth, particularly where the tooth socket is substantially reduced in viable periodontal tissue. In fact, the processes and compositions of the invention work well when a tooth socket has lost 30–50% of the periodontal ligament, and as much as 50–100% of the periodontal ligament. The methods and compositions include providing to the tooth or tooth socket surface a therapeutically effective concentration of a morphogen or morphogen-stimulating agent sufficient to induce morphogenesis of periodontal tissue. The implanted tooth may be an implanted tooth which has grown naturally in the socket and which is loose as a result of, for example, mechanical injury or due to a dental or periodontal disease. Alternatively, the implanted tooth may be a lost tooth or a tooth prosthesis which has been reimplanted in a vacant tooth socket. The tooth prosthesis may include a natural tooth from which a damaged or diseased root has been removed and replaced with a biocompatible, biologically inert material, as is created in a root canal procedure. The prosthetic tooth also may be composed of synthetic, non dentin-containing materials.

The morphogen may be provided directly to the tooth surface to be implanted, and/or to the tooth socket to which the tooth is to be implanted. Where the morphogen is to be provided to the tissue socket, it may be provided by topical administration to the tooth socket surface or by local injection to periodontal or alveolar bone tissue associated with the socket. Alternatively, an agent capable of stimulating the production and/or secretion of a therapeutically effective concentration of an endogenous morphogen also may be provided to the tooth or tooth socket. Where the morphogen or morphogen stimulating agent (referred to herein collectively as "therapeutic agent") is provided to the tooth surface, it preferably is dispersed in a biocompatible, bioresorbable carrier, most preferably a carrier capable of retaining the therapeutic agent at the tissue surface and/or providing a controlled delivery of the agent to the tooth socket. The therapeutic agent also may be provided to the tooth socket itself, also preferably in association with a carrier capable of maintaining the agent in the tooth socket, and/or capable of enhancing the controlled delivery of the agent to the socket. Useful carriers include compositions having a high viscosity, such as that provided by glycerol and the like, as well as carrier materials formulated from extracellular matrices and/or which contain laminin, collagen, and/or biocompatible synthetic polymers, such as polybutyric, polylactic, polyglycolic acids and copolymers thereof. In addition, or alternatively, an acellular carrier material may be formulated from bone, dentin, cementum or periodontal tissue by demineralizing and guanidine-extracting the tissue essentially as described herein and/or in U.S. Ser. No. 752,674. Particularly useful acellular matrices include dentin-derived, periodontal ligament-derived and cementum-derived matrices.

In addition, the tooth to be implanted preferably comprises a porous exterior surface onto which the therapeutic agent may be adsorbed, and into which progenitor and differentiating cementoblasts can infiltrate and proliferate. Useful surfaces include natural tooth root surfaces, and porous prosthetic surfaces, including surfaces composed of matrix materials such as collagen, laminin, biocompatible polymers or metals such as titanium oxide. Where a natural tooth or dentin-containing prosthesis is to be implanted, the surface to be implanted first may be partially demineralized, e.g., by transient exposure to an acid to enhance the porosity of the tooth root surface.

Preferably, where the tooth is to be implanted into a tooth socket, the socket has been freed of fibrous tissue which may have formed following tooth loss and periodontal tissue resorption. For example, the tooth socket may have undergone a healing period of several months after loss or removal of the tooth such that scar tissue has formed over the wound. In this case the healed socket preferably is surgically prepared for tooth implantation by removing the scar and other undesired tissue to expose the alveolar bone surface.

Preferably, where the therapeutic agent is to be provided to enhance periodontal tissue viability surrounding an implanted tooth, the therapeutic agent is provided topically to the tissue surfaces between the tooth and gingiva. Alternatively, the agent may be injected locally, e.g., into the gingiva itself.

The morphogens described herein may be used to inhibit periodontal tissue loss and/or to enhance viability of periodontal tissue at risk of damage due to a periodontal disease. The periodontal disease may be caused by an infectious agent, such as a bacterial, fungal or viral agent, or by a nutritional deficiency, including a vitamin deficiency. The morphogens also may be used to regenerate periodontal tissue lost as a result of a neoplastic disease, including squamous cell carcinomas, acute leukemias, lymphomas and metastatic tumors. A detailed description of diseases which damage or destroy periodontal tissue can be found, for example, in *Harrison's Principles of Internal Medicine*, 243–248, (McGraw-Hill 12th ed. 1991), the disclosure of which is incorporated herein by reference. The efficacy of the morphogens described herein in modulating an inflammatory response and inhibiting tissue damage associated with ulcerations of oral mucosa are described in detail in U.S. Ser. No. 08/462,623, the disclosure of which is incorporated herein by reference.

Although all individuals, and particularly adults, are at risk for periodontal tissue damage due to periodontal disease, a population most particularly at risk are immune-compromised individuals, such as individuals suffering from autoimmune diseases and/or whose immune system has been suppressed as part of a clinical procedure or therapy. Thus, in another aspect, the invention provides methods and compositions for inhibiting periodontal tissue loss in immune-compromised individuals.

As described in copending U.S. Ser. No. 07/752,764, now abandoned, the disclosure of which is incorporated hereinabove by reference, and Example 2, below, the morphogens described herein also can induce formation of damaged or lost dentin tissue. Accordingly, where a natural tooth or dentin-containing prosthesis is to be implanted, a morphogen or morphogen-stimulating agent also may be provided to damaged areas of the tooth to induce dentin regeneration of damaged or lost dentin tissue. The morphogen may be provided topically or otherwise administered to the tooth tissue. For example, the morphogen may be dispersed in a biocompatible, porous carrier material that then is provided topically to the damaged dentin tissue. A useful carrier may be formulated from dentin by demineralizing and guanidine-extracting the tissue to create an acellular matrix.

The morphogens and morphogen-stimulating agents also may be provided to the periodontium together with other molecules ("cofactors") known to have a beneficial effect in treating damaged periodontal tissue, particularly cofactors capable of mitigating or alleviating symptoms typically associated with periodontal tissue damage and/or loss. Examples of such cofactors include antiseptics such as chlorohexidine and tibezonium iodide, antibiotics, including tetracycline, aminoglycosides, macrolides, penicillins and cephalosporins, anaesthetics and analgesics, and other non-steroidal anti-inflammatory agents.

Among the morphogens useful in this invention are proteins originally identified as osteogenic proteins (see U.S. Pat. No. 5,011,691, incorporated herein by reference), such as the OP-1, OP-2 and CBMP2 proteins, as well as amino acid sequence-related proteins such as DPP (from Drosophila), Vgl (from Xenopus), Vgr-1 (from mouse), GDF-1 (from mouse, see Lee (1991) *PNAS* 88:4250–4254), all of which are presented in Table II and Seq. ID Nos.5–14, and the recently identified 60A protein (from Drosophila, Seq. ID No. 24, see Wharton et al. (1991) *PNAS* 88:9214–9218.) The members of this family, which include members of the TGF-β super-family of proteins, share substantial amino acid sequence homology in their C-terminal regions. The proteins are translated as a precursor, having an N-terminal signal peptide sequence, typically less than about 30 residues, followed by a "pro" domain that is cleaved to yield the mature sequence. The "pro" form of the protein includes the pro domain and the mature domain, and forms a soluble species that appears to be the primary form secreted from cultured mammalian cells. The signal peptide is cleaved rapidly upon translation, at a cleavage site that can be predicted in a given sequence using the method of Von Heijne ((1986) *Nucleic Acids Research* 14:4683–4691.) Table I, below, describes the various morphogens identified to date, including their nomenclature as used herein, their Seq. ID references, and publication sources for the amino acid sequences for the full length proteins not included in the Seq. Listing. The disclosure of these publications is incorporated herein by reference.

TABLE I

| | |
|---|---|
| "OP-1" | Refers generically to the group of morphogenically active proteins expressed from part or all of a DNA sequence encoding OP-1 protein, including allelic and species variants thereof, e.g., human OP-1 ("hOP-1", Seq. ID No. 5, mature protein amino acid sequence), or mouse Op-1 ("mOP-1", Seq. ID No. 6, mature protein amino acid sequence.) The conserved seven cysteine skeleton is defined by residues 38 to 139 of Seq. ID Nos. 5 and 6. The cDNA sequences and the amino acids encoding the full length proteins are provided in Seq. Id Nos. 16 and 17 (hOP1) and Seq. ID Nos. 18 and 19 (mOP1.) The mature proteins are defined by residues 293–431 (hOP1) and 292–430 (mOP1). The "pro" regions of the proteins, cleaved to yield the mature, morphogenically active proteins are defined essentially by residues 30–292 (hOP1) and residues 30–291 (mOP1). |
| "OP-2" | Refers generically to the group of active proteins expressed from part or all of a DNA sequence encoding OP-2 protein, including allelic and species variants thereof, e.g., human OP-2 ("hOP-2", Seq. ID No.7, mature protein amino acid sequence) or mouse OP-2 ("mOP-2", Seq. ID No. 8, mature protein amino acid sequence). The conserved seven cysteine skeleton is defined by residues 38 to 139 of Seq. ID Nos. 7 and 8. The cDNA sequences and the amino acids encoding the full length proteins are provided in Seq. ID Nos. 20 and 21 (hOP2) and Seq. ID Nos. 22 and 23 (mOP2.) The mature proteins are defined essentially by residues 264–402 (hOP2) and 261–399 (mOP2). The "pro" regions of the proteins, cleaved to yield the mature, morphogenically active proteins are defined essentially by residues 18–263 (hOP2) and residues 18–260 (mOP1). |
| "CBMP2" | Refers generically to the morphogenically active proteins expressed from a DNA sequence encoding the CBMP2 proteins, including allelic and species variants thereof, e.g., human CBMP2A ("CBMP2A(fx)", Seq. ID No. 9) or human CBMP2B DNA ("CBMP2B(fx)", Seq. ID No. 10). The amino acid sequence for the full length proteins, referred to in the literature as BMP2A and BMP2B, or BMP2 and BMP4, appear in Wozney, et al. (1988) Science 242:1528–1534. The pro domain for BMP2 (BMP2A) likely includes residues 25–248; the mature protein, residues 249–396. The pro domain for BMP4 (BMP2B) likely includes residues 25–256; the mature protein, residues 257–408. |
| "DPP(fx)" | refers to protein sequences encoded by the Drosophila DPP gene and defining the conserved seven cysteine skeleton (Seq. ID No. 11). The amino acid sequence for the full length protein appears in Padgett, et al (1987) Nature 325: 81–84. The pro domain likely extends from the signal peptide cleavage site to residue 456; the mature protein likely is defined by residues 457–588. |
| "Vgl(fx)" | refers to protein sequences encoded by the Xenopus Vgl gene and defining the conserved seven cysteine skeleton (Seq. ID No. 12). The amino acid sequence for the full length protein appears in Weeks (1987) Cell 51: 861–867. The prodomain likely extends from the signal peptide cleavage site to residue 246; the mature protein likely is defined by residues 247–360. |
| "Vgr-1(fx)" | refers to protein sequences encoded by the murine Vgr-1 gene and defining the conserved seven cysteine skeleton (Seq. ID No. 13). The amino acid sequence for the full length protein appears in Lyons, et al, (1989) PNAS 86: 4554–4558. The prodomain likely extends from the signal peptide cleavage site to residue 299; the mature protein likely is defined by |

TABLE I-continued

| | |
|---|---|
| | residues 300–438. |
| "GDF-1(fx)" | refers to protein sequences encoded by the human GDF-1 gene and defining the conserved seven cysteine skeleton (Seq. ID No. 14). The cDNA and encoded amino sequence for the full length protein is provided in Seq. ID No. 32. The prodomain likely extends from the signal peptide clavage site to residue 214; the mature protein likely is defined by residues 215–372. |
| "60A" | refers generically to the morphogenically active proteins expressed from part or all of a DNA sequence (from the Drosophila 60A gene) encoding the 60A proteins (see Seq. ID No. 24 wherein the cDNA and encoded amino acid sequence for the full length protein is provided). "60A(fx)" refers to the protein sequences defining the conserved seven cysteine skeleton (residues 354 to 455 of Seq. ID No. 24.) The prodomain likely extends from the signal peptide cleavage site to residue 324; the mature protein likely is defined by residues 325–455. |
| "BMP3(fx)" | refers to protein sequences encoded by the human BMP3 gene and defining the conserved seven cysteine skeleton (Seq. ID No. 26). The amino acid sequence for the full length protein appears in Wozney et al. (1988) Science 242: 1528–1534. The pro domain likely extends from the signal peptide cleavage site to residue 290; the mature protein likely is defined by residues 291–472. |
| "BMP5(fx)" | refers to protein sequences encoded by the human BMP5 gene and defining the conserved seven cysteine skeleton (Seq. ID No. 27). The amino acid sequence for the full length protein appears in Celeste, et al. (1991) PNAS 87: 9843–9847. The pro domain likely extends from the signal peptide cleavage site to residue 316; the mature protein likely is defined by residues 317–454. |
| "BMP6(fx)" | refers to protein sequences encoded by the human BMP6 gene and defining the conserved seven cysteine skeleton (Seq. ID No. 28). The amino acid sequence for the full length protein appears in Celeste, et al. (1990) PNAS 87: 9843–5847. The pro domain likely includes extends from the signal peptide cleavage site to residue 374; the mature sequence likely includes residues 375–513. |

The OP-2 proteins have an additional cysteine residue in the conserved region (e.g., see residue 41 of Seq. ID Nos. 7 and 8), in addition to the conserved cysteine skeleton in common with the other proteins in this family. The GDF-1 protein has a four amino acid insert within the conserved skeleton (residues 44–47 of Seq. ID No. 14) but this insert likely does not interfere with the relationship of the cysteines in the folded structure. In addition, the CBMP2 proteins are missing one amino acid residue within the cysteine skeleton.

The morphogens are inactive when reduced, but are active as oxidized homodimers and when oxidized in combination with other morphogens of this invention. Thus, as defined herein, a morphogen is a dimeric protein comprising a pair of polypeptide chains, wherein each polypeptide chain comprises at least the C-terminal six cysteine skeleton defined by residues 43–139 of Seq. ID No. 5, including functionally equivalent arrangements of these cysteines (e.g., amino acid insertions or deletions which alter the linear arrangement of the cysteines in the sequence but not their relationship in the folded structure), such that, when the polypeptide chains are folded, the dimeric protein species comprising the pair of polypeptide chains has the appropriate three-dimensional structure, including the appropriate intra- and/or inter-chain disulfide bonds such that the protein is capable of acting as a morphogen as defined herein. Specifically, the morphogens generally are capable of all of the following biological functions in a morphogenically permissive environment: stimulating proliferation of progenitor cells; stimulating the differentiation of progenitor cells; stimulating the proliferation of differentiated cells; and supporting the growth and maintenance of differentiated cells, including the "redifferentiation" of transformed cells. In addition, it is also anticipated that these morphogens are capable of inducing redifferentiation of committed cells under appropriate environmental conditions.

In one preferred aspect, the morphogens of this invention comprise one of two species of generic amino acid sequences: Generic Sequence 1 (Seq. ID No. 1) or Generic Sequence 2 (Seq. ID No. 2); where each Xaa indicates one of the 20 naturally-occurring L-isomer, α-amino acids or a derivative thereof. Generic Sequence 1 comprises the conserved six cysteine skeleton and Generic Sequence 2 comprises the conserved six cysteine skeleton plus the additional cysteine identified in OP-2 (see residue 36, Seq. ID No. 2). In another preferred aspect, these sequences further comprise the following additional sequence at their N-terminus:

Cys Xaa Xaa Xaa Xaa  (Seq. ID No. 15)
 1            5

Preferred amino acid sequences within the foregoing generic sequences include: Generic Sequence 3 (Seq. ID No. 3), Generic Sequence 4 (Seq. ID No. 4), Generic Sequence 5 (Seq. ID No. 30) and Generic Sequence 6 (Seq. ID No. 31), listed below. These Generic Sequences accommodate the homologies shared among the various preferred members of this morphogen family identified in Table II, as well as the amino acid sequence variation among them. Generic Sequences 3 and 4 are composite amino acid sequences of the proteins presented in Table II and identified in Seq. ID Nos. 5–14, specifically: human OP-1 (hOP-1, Seq. ID Nos. 5 and 16–17), mouse OP-1 (mOP-1, Seq. ID Nos. 6 and 18–19), human and mouse OP-2 (Seq. ID Nos. 7, 8, and 20–22), CBMP2A (Seq. ID No. 9), CBMP2B (Seq. ID No. 10), DPP (from Drosophila, Seq. ID No. 11), Vgl, (from Xenopus, Seq. ID No. 12), Vgr-1 (from mouse, Seq. ID No. 13), and GDF-1 (from mouse, Seq. ID No. 14.) The generic sequences include both the amino acid identity shared by the sequences in Table II, as well as alternative residues for the variable positions within the sequence. Note that these generic sequences allow for an additional cysteine at position 41 or 46 in Generic Sequences 3 or 4, respectively, providing an appropriate cysteine skeleton where inter- or intramolecular disulfide bonds can form, and contain certain critical amino acids which influence the tertiary structure of the proteins.

Generic Sequence 3 (SEQ ID NO: 3)

| Leu | Tyr | Val | Xaa | Phe | | | |
| 1 | | | | 5 | | | |
| Xaa | Xaa | Xaa | Gly | Trp | Xaa | Xaa | Trp | Xaa |
| | | | | 10 | | | | |
| Xaa | Ala | Pro | Xaa | Gly | Xaa | Xaa | Ala | |
| 15 | | | | | 20 | | | |
| Xaa | Tyr | Cys | Xaa | Gly | Xaa | Cys | Xaa | |
| | | 25 | | | | | 30 | |

-continued

Generic Sequence 3 (SEQ ID NO: 3)

```
Xaa Pro  Xaa  Xaa  Xaa  Xaa  Xaa
                    35
Xaa Xaa  Xaa  Asn  His  Ala  Xaa  Xaa
         40                        45
Xaa Xaa  Leu  Xaa  Xaa  Xaa  Xaa  Xaa
                    50
Xaa Xaa  Xaa  Xaa  Xaa  Xaa  Xaa  Cys
     55                        60
Cys Xaa  Pro  Xaa  Xaa  Xaa  Xaa  Xaa
               65
Xaa Xaa  Xaa  Leu  Xaa  Xaa  Xaa
 70                       75
Xaa Xaa  Xaa  Xaa  Val  Xaa  Leu  Xaa
                80
Xaa Xaa  Xaa  Xaa  Met  Xaa  Val  Xaa
 85                        90
Xaa Cys  Gly  Cys  Xaa
          95
``` wherein each Xaa is independently selected from a group of one or more specified amino acids defined as follows: "Res." means "residue" and Xaa at res.4=(Ser, Asp or Glu); Xaa at res.6=(Arg, Gln, Ser or Lys); Xaa at res.7=(Asp or Glu); Xaa at res.8=(Leu or Val); Xaa at res.11=(Gln, Leu, Asp, His or Asn); Xaa at res.12=(Asp, Arg or Asn); Xaa at res.14=(Ile or Val); Xaa at res.15=(Ile or Val); Xaa at res.18=(Glu, Gln, Leu, Lys, Pro or Arg); Xaa at res.20=(Tyr or Phe); Xaa at res.21=(Ala, Ser, Asp, Met, His, Leu or Gln); Xaa at res.23=(Tyr, Asn or Phe); Xaa at res.26=(Glu, His, Tyr, Asp or Gln); Xaa at res.28=(Glu, Lys, Asp or Gln); Xaa at res.30=(Ala, Ser, Pro or Gln); Xaa at res.31=(Phe, Leu or Tyr); Xaa at res.33=(Leu or Val); Xaa at res.34=(Asn, Asp, Ala or Thr); Xaa at res.35=(Ser, Asp, Glu, Leu or Ala); Xaa at res.36=(Tyr, Cys, His, Ser or Ile); Xaa at res.37=(Met, Phe, Gly or Leu); Xaa at res.38=(Asn or Ser); Xaa at res.39=(Ala, Ser or Gly); Xaa at res.40=(Thr, Leu or Ser); Xaa at res.44=(Ile or Val); Xaa at res.45=(Val or Leu); Xaa at res.46=(Gln or Arg); Xaa at res.47=(Thr, Ala or Ser); Xaa at res.49=(Val or Met); Xaa at res.50=(His or Asn); Xaa at res.51=(Phe, Leu, Asn, Ser, Ala or Val); Xaa at res.52=(Ile, Met, Asn, Ala or Val); Xaa at res.53=(Asn, Lys, Ala or Glu); Xaa at res.54=(Pro or Ser); Xaa at res.55=(Glu, Asp, Asn, or Gly); Xaa at res.56=(Thr, Ala, Val, Lys, Asp, Tyr, Ser or Ala); Xaa at res.57=(Val, Ala or Ile); Xaa at res.58=(Pro or Asp); Xaa at res.59=(Lys or Leu); Xaa at res.60=(Pro or Ala); Xaa at res.63=(Ala or Val); Xaa at res.65=(Thr or Ala); Xaa at res.66=(Gln, Lys, Arg or Glu); Xaa at res.67=(Leu, Met or Val); Xaa at res.68=(Asn, Ser or Asp); Xaa at res.69=(Ala, Pro or Ser); Xaa at res.70=(Ile, Thr or Val); Xaa at res.71=(Ser or Ala); Xaa at res.72=(Val or Met); Xaa at res.74=(Tyr or Phe); Xaa at res.75=(Phe, Tyr or Leu); Xaa at res.76=(Asp or Asn); Xaa at res.77=(Asp, Glu, Asn or Ser); Xaa at res.78=(Ser, Gln, Asn or Tyr); Xaa at res.79=(Ser, Asn, Asp or Glu); Xaa at res.80=(Asn, Thr or Lys); Xaa at res.82=(Ile or Val); Xaa at res.84=(Lys or Arg); Xaa at res.85=(Lys, Asn, Gln or His); Xaa at res.86=(Tyr or His); Xaa at res.87=(Arg, Gln or Glu); Xaa at res.88=(Asn, Glu or Asp); Xaa at res.90=(Val, Thr or Ala); Xaa at res.92=(Arg, Lys, Val, Asp or Glu); Xaa at res.93=(Ala, Gly or Glu); and Xaa at res.97=(His or Arg);

Generic Sequence 4 (SEQ ID NO: 4)

```
Cys Xaa  Xaa  Xaa  Xaa  Leu  Tyr  Val  Xaa  Phe
 1              5                             10
Xaa Xaa  Xaa  Gly  Trp  Xaa  Xaa  Trp  Xaa
                    15
Xaa Ala  Pro  Xaa  Gly  Xaa  Xaa  Ala
 20                       25
Xaa Tyr  Cys  Xaa  Gly  Xaa  Cys  Xaa
          30                        35
Xaa Pro  Xaa  Xaa  Xaa  Xaa  Xaa
                    40
Xaa Xaa  Xaa  Asn  His  Ala  Xaa  Xaa
               45                    50
Xaa Xaa  Leu  Xaa  Xaa  Xaa  Xaa  Xaa
                    55
Xaa Xaa  Xaa  Xaa  Xaa  Xaa  Xaa  Cys
     60                        65
Cys Xaa  Pro  Xaa  Xaa  Xaa  Xaa  Xaa
               70
Xaa Xaa  Xaa  Leu  Xaa  Xaa  Xaa
 75                       80
Xaa Xaa  Xaa  Xaa  Val  Xaa  Leu  Xaa
                85
Xaa Xaa  Xaa  Xaa  Met  Xaa  Val  Xaa
 90                        95
Xaa Cys  Gly  Cys  Xaa
          100
``` wherein each Xaa is independently selected from a group of one or more specified amino acids as defined by the following: "Res." means "residue" and Xaa at res.2=(Lys or Arg); Xaa at res.3=(Lys or Arg); Xaa at res.4=(His or Arg); Xaa at res.5=(Glu, Ser, His, Gly, Arg or Pro); Xaa at res.9=(Ser, Asp or Glu); Xaa at res.11=(Arg, Gln, Ser or Lys); Xaa at res.12=(Asp or Glu); Xaa at res.13=(Leu or Val); Xaa at res.16=(Gln, Leu, Asp, His or Asn); Xaa at res.17=(Asp, Arg, or Asn); Xaa at res.19=(Ile or Val); Xaa at res.20=(Ile or Val); Xaa at res.23=(Glu, Gln, Leu, Lys, Pro or Arg); Xaa at res.25=(Tyr or Phe); Xaa at res.26=(Ala, Ser, Asp, Met, His, Leu, or Gln); Xaa at res.28=(Tyr, Asn or Phe); Xaa at res.31=(Glu, His, Tyr, Asp or Gln); Xaa at res.33=Glu, Lys, Asp or Gln); Xaa at res.35=(Ala, Ser or Pro); Xaa at res.36=(Phe, Leu or Tyr); Xaa at res.38=(Leu or Val); Xaa at res.39=(Asn, Asp, Ala or Thr); Xaa at res.40=(Ser, Asp, Glu, Leu or Ala); Xaa at res.41=(Tyr, Cys, His, Ser or Ile); Xaa at res.42=(Met, Phe, Gly or Leu); Xaa at res.44=(Ala, Ser or Gly); Xaa at res.45=(Thr, Leu or Ser); Xaa at res.49=(Ile or Val); Xaa at res.50=(Val or Leu); Xaa at res.51=(Gln or Arg); Xaa at res.52=(Thr, Ala or Ser); Xaa at res.54=(Val or Met); Xaa at res.55=(His or Asn); Xaa at res.56=(Phe, Leu, Asn, Ser, Ala or Val); Xaa at res.57=(Ile, Met, Asn, Ala or Val); Xaa at res.58=(Asn, Lys, Ala or Glu); Xaa at res.59=(Pro or Ser); Xaa at res.60=(Glu, Asp, or Gly); Xaa at res.61=(Thr, Ala, Val, Lys, Asp, Tyr, Ser or Ala); Xaa at res.62=(Val, Ala or Ile); Xaa at res.63=(Pro or Asp); Xaa at res.64=(Lys or Leu); Xaa at res.65=(Pro or Ala); Xaa at res.68=(Ala or Val); Xaa at res.70=(Thr or Ala); Xaa at res.71=(Gln, Lys, Arg or Glu); Xaa at res.72=(Leu, Met or Val); Xaa at res.73=(Asn, Ser or Asp); Xaa at res.74=(Ala, Pro or Ser); Xaa at res.75=(Ile, Thr or Val); Xaa at res.76=(Ser or Ala); Xaa at res.77=(Val or Met); Xaa at res.79=(Tyr or Phe); Xaa at res.80=(Phe, Tyr or Leu); Xaa at res.81=(Asp or Asn); Xaa at res.82=(Asp, Glu, Asn or Ser); Xaa at res.83=(Ser, Gln, Asn or Tyr); Xaa at res.84=(Ser, Asn, Asp or Glu); Xaa at res.85=(Asn, Thr or Lys); Xaa at res.87=(Ile or Val); Xaa at res.89=(Lys or Arg); Xaa at res.90=(Lys, Asn, Gln or His); Xaa at res.91=(Tyr or His); Xaa at res.92=(Arg, Gln or Glu); Xaa at res.93=(Asn, Glu or Asp); Xaa at res.95=(Val, Thr or Ala); Xaa at res.97=(Arg, Lys, Val, Asp or Glu); Xaa at res.98=(Ala, Gly or Glu); and Xaa at res.102=(His or Arg).

Similarly, Generic Sequence 5 (Seq. ID No. 30) and Generic Sequence 6 (Seq. ID No. 31) accommodate the homologies shared among all the morphogen protein family members identified in Table II. Specifically, Generic Sequences 5 and 6 are composite amino acid sequences of human OP-1 (hOP-1, Seq. ID Nos. 5 and 16–17), mouse OP-1 (mOP-1, Seq. ID Nos. 6 and 18–19), human and mouse OP-2 (Seq. ID Nos. 7, 8, and 20–22), CBMP2A (Seq. ID No. 9), CBMP2B (Seq. ID No. 10), DPP (from Drosophila, Seq. ID No. 11), Vgl, (from Xenopus, Seq. ID No. 12), Vgr-1 (from mouse, Seq. ID No. 13), and GDF-1 (from mouse, Seq. ID No. 14), human BMP3 (Seq. ID No. 26), human BMP5 (Seq. ID No. 27), human BMP6 (Seq. ID No. 28) and 60(A) (from Drosophila, Seq. ID Nos. 24–25). The generic sequences include both the amino acid identity shared by these sequences in the C-terminal domain, defined by the six and seven cysteine skeletons (Generic Sequences 5 and 6, respectively), as well as alternative residues for the variable positions within the sequence. As for Generic Sequences 3 and 4, Generic Sequences 5 and 6 allow for an additional cysteine at position 41 (Generic Sequence 5) or position 46 (Generic Sequence 6), providing an appropriate cysteine skeleton where inter- or intramolecular disulfide bonds can form, and containing certain critical amino acids which influence the tertiary structure of the proteins.

Generic Sequence 5 (SEQ ID NO: 3)

| Leu 1 | Xaa | Xaa | Xaa | Phe 5 | | | |
|---|---|---|---|---|---|---|---|
| Xaa | Xaa | Xaa | Gly | Trp 10 | Xaa | Xaa | Trp | Xaa |
| Xaa 15 | Xaa | Pro | Xaa | Xaa | Xaa 20 | Xaa | Ala |
| Xaa | Tyr | Cys 25 | Xaa | Gly | Xaa | Cys | Xaa 30 |
| Xaa | Pro | Xaa | Xaa | Xaa 35 | Xaa | Xaa | |
| Xaa | Xaa | Xaa 40 | Asn | His | Ala | Xaa | Xaa 45 |
| Xaa | Xaa | Xaa | Xaa | Xaa 50 | Xaa | Xaa | |
| Xaa | Xaa | Xaa 55 | Xaa | Xaa | Xaa | Xaa 60 | Cys |
| Cys | Xaa | Pro | Xaa 65 | Xaa | Xaa | Xaa | Xaa |
| Xaa 70 | Xaa | Xaa | Leu | Xaa | Xaa 75 | Xaa | |
| Xaa | Xaa | Xaa | Xaa 80 | Val | Xaa | Leu | Xaa |
| Xaa 85 | Xaa | Xaa | Xaa | Met | Xaa 90 | Val | Xaa |
| Xaa | Cys | Xaa | Cys 95 | Xaa | | | | wherein each Xaa is independently selected from a group of one or more specified amino acids defined as follows: "Res." means "residue" and Xaa at res.2=(Tyr or Lys); Xaa at res.3=Val or Ile); Xaa at res.4=(Ser, Asp or Glu); Xaa at res.6=(Arg, Gln, Ser, Lys or Ala); Xaa at res.7=(Asp, Glu or Lys); Xaa at res.8=(Leu, Val or Ile); Xaa at res.11=(Gln, Leu, Asp, His, Asn or Ser); Xaa at res.12=(Asp, Arg, Asn or Glu); Xaa at res.14=(Ile or Val); Xaa at res.15=(Ile or Val); Xaa at res.16 (Ala or Ser); Xaa at res.18=(Glu, Gln, Leu, Lys, Pro or Arg); Xaa at res.19=(Gly or Ser); Xaa at res.20=(Tyr or Phe); Xaa at res.21=(Ala, Ser, Asp, Met, His, Gln, Leu or Gly); Xaa at res.23=(Tyr, Asn or Phe); Xaa at res.26=(Glu, His, Tyr, Asp, Gln or Ser); Xaa at res.28=(Glu, Lys, Asp, Gln or Ala); Xaa at res.30=(Ala, Ser, Pro, Gln or Asn); Xaa at res.31=(Phe, Leu or Tyr); Xaa at res.33=(Leu, Val or Met); Xaa at res.34=(Asn, Asp, Ala, Thr or Pro); Xaa at res.35= (Ser, Asp, Glu, Leu, Ala or Lys); Xaa at res.36=(Tyr, Cys, His, Ser or Ile); Xaa at res.37=(Met, Phe, Gly or Leu); Xaa at res.38=(Asn, Ser or Lys); Xaa at res.39=(Ala, Ser, Gly or Pro); Xaa at res.40=(Thr, Leu or Ser); Xaa at res.44=(Ile, Val or Thr); Xaa at res.45=(Val, Leu or Ile); Xaa at res.46=(Gln or Arg); Xaa at res.47=(Thr, Ala or Ser); Xaa at res.48=(Leu or Ile); Xaa at res.49=(Val or Met); Xaa at res.50=(His, Asn or Arg); Xaa at res.51=(Phe, Leu, Asn, Ser, Ala or Val); Xaa at res.52=(Ile, Met, Asn, Ala, Val or Leu); Xaa at res.53= (Asn, Lys, Ala, Glu, Gly or Phe); Xaa at res.54=(Pro, Ser or Val); Xaa at res.55=(Glu, Asp, Asn, Gly, Val or Lys); Xaa at res.56=(Thr, Ala, Val, Lys, Asp, Tyr, Ser, Ala, Pro or His); Xaa at res.57=(Val, Ala or Ile); Xaa at res.58=(Pro or Asp); Xaa at res.59=(Lys, Leu or Glu); Xaa at res.60=(Pro or Ala); Xaa at res.63=(Ala or Val); Xaa at res.65=(Thr, Ala or Glu); Xaa at res.66=(Gln, Lys, Arg or Glu); Xaa at res.67=(Leu, Met or Val); Xaa at res.68=(Asn, Ser, Asp or Gly); Xaa at res.69=(Ala, Pro or Ser); Xaa at res.70=(Ile, Thr, Val or Leu); Xaa at res.71=(Ser, Ala or Pro); Xaa at res.72=(Val, Met or Ile); Xaa at res.74=(Tyr or Phe); Xaa at res.75=(Phe, Tyr, Leu or His); Xaa at res.76=(Asp, Asn or Leu); Xaa at res.77=(Asp, Glu, Asn or Ser); Xaa at res.78=(Ser, Gln, Asn, Tyr or Asp); Xaa at res.79=(Ser, Asn, Asp, Glu or Lys); Xaa at res.80=(Asn, Thr or Lys); Xaa at res.82=(Ile, Val or Asn); Xaa at res.84=(Lys or Arg); Xaa at res.85=(Lys, Asn, Gln, His or Val); Xaa at res.86=(Tyr or His); Xaa at res.87=(Arg, Gln, Glu or Pro); Xaa at res.88=(Asn, Glu or Asp); Xaa at res.90=(Val, Thr, Ala or Ile); Xaa at res.92=(Arg, Lys, Val, Asp or Glu); Xaa at res.93=(Ala, Gly, Glu or Ser); Xaa at res.95=(Gly or Ala) and Xaa at res.97=(His or Arg).

Generic Sequence 6 (SEQ ID NO: 31)

| Cys 1 | Xaa | Xaa | Xaa | Xaa 5 | Leu | Xaa | Xaa | Xaa | Phe 10 |
|---|---|---|---|---|---|---|---|---|---|
| Xaa | Xaa | Xaa | Gly | Trp 15 | Xaa | Xaa | Trp | Xaa | |
| Xaa 20 | Xaa | Pro | Xaa | Xaa | Xaa 25 | Xaa | Ala | | |
| Xaa | Tyr | Cys 30 | Xaa | Gly | Xaa | Cys | Xaa 35 | | |
| Xaa | Pro | Xaa | Xaa | Xaa 40 | Xaa | Xaa | | | |
| Xaa | Xaa | Xaa | Asn 45 | His | Ala | Xaa | Xaa 50 | | |
| Xaa | Xaa | Xaa | Xaa | Xaa 55 | Xaa | Xaa | | | |
| Xaa | Xaa | Xaa | Xaa 60 | Xaa | Xaa | Xaa | Cys 65 | | |
| Cys | Xaa | Pro | Xaa 70 | Xaa | Xaa | Xaa | Xaa | | |

Generic Sequence 6 (SEQ ID NO: 31)

```
Xaa  Xaa  Xaa  Leu  Xaa  Xaa  Xaa
 75                  80
Xaa  Xaa  Xaa  Xaa  Val  Xaa  Leu  Xaa
               85
Xaa  Xaa  Xaa  Xaa  Met  Xaa  Val  Xaa
 90                       95
Xaa  Cys  Xaa  Cys  Xaa
          100
``` wherein each Xaa is independently selected from a group of one or more specified amino acids as defined by the following: "Res." means "residue" and Xaa at res.2=(Lys, Arg, Ala or Gln); Xaa at res.3=(Lys, Arg or Met); Xaa at res.4=(His, Arg or Gln); Xaa at res.5=(Glu, Ser, His, Gly, Arg, Pro, Thr, or Tyr); Xaa at res.7=(Tyr or Lys); Xaa at res.8=(Val or Ile); Xaa at res.9=(Ser, Asp or Glu); Xaa at res.11=(Arg, Gln, Ser, Lys or Ala); Xaa at res.12=(Asp, Glu, or Lys); Xaa at res.13=(Leu, Val or Ile); Xaa at res.16=(Gln, Leu, Asp, His, Asn or Ser); Xaa at res.17=(Asp, Arg, Asn or Glu); Xaa at res.19=(Ile or Val); Xaa at res.20=(Ile or Val); Xaa at res.21=(Ala or Ser); Xaa at res.23=(Glu, Gln, Leu, Lys, Pro or Arg); Xaa at res.24=(Gly or Ser); Xaa at res.25=(Tyr or Phe); Xaa at res.26=(Ala, Ser, Asp, Met, His, Gln, Leu, or Gly); Xaa at res.28=(Tyr, Asn or Phe); Xaa at res.31=(Glu, His, Tyr, Asp, Gln or Ser); Xaa at res.33=Glu, Lys, Asp, Gln or Ala); Xaa at res.35=(Ala, Ser, Pro, Gln or Asn); Xaa at res.36=(Phe, Leu or Tyr); Xaa at res.38=(Leu, Val or Met); Xaa at res.39=(Asn, Asp, Ala, Thr or Pro); Xaa at res.40=(Ser, Asp, Glu, Leu, Ala or Lys); Xaa at res.41=(Tyr, Cys, His, Ser or Ile); Xaa at res.42=(Met, Phe, Gly or Leu); Xaa at res.43=(Asn, Ser or Lys); Xaa at res.44=(Ala, Ser, Gly or Pro); Xaa at res.45=(Thr, Leu or Ser); Xaa at res.49=(Ile, Val or Thr); Xaa at res.50=(Val, Leu or Ile); Xaa at res.51=(Gln or Arg); Xaa at res.52=(Thr, Ala or Ser); Xaa at res.53=(Leu or Ile); Xaa at res.54=(Val or Met); Xaa at res.55=(His, Asn or Arg); Xaa at res.56=(Phe, Leu, Asn, Ser, Ala or Val); Xaa at res.57=(Ile, Met, Asn, Ala, Val or Leu); Xaa at res.58=(Asn, Lys, Ala, Glu, Gly or Phe); Xaa at res.59=(Pro, Ser or Val); Xaa at res.60=(Glu, Asp, Gly, Val or Lys); Xaa at res.61=(Thr, Ala, Val, Lys, Asp, Tyr, Ser, Ala, Pro or His); Xaa at res.62=(Val, Ala or Ile); Xaa at res.63=(Pro or Asp); Xaa at res.64=(Lys, Leu or Glu); Xaa at res.65=(Pro or Ala); Xaa at res.68=(Ala or Val); Xaa at res.70=(Thr, Ala or Glu); Xaa at res.71=(Gln, Lys, Arg or Glu); Xaa at res.72=(Leu, Met or Val); Xaa at res.73=(Asn, Ser, Asp or Gly); Xaa at res.74=(Ala, Pro or Ser); Xaa at res.75=(Ile, Thr, Val or Leu); Xaa at res.76=(Ser, Ala or Pro); Xaa at res.77=(Val, Met or Ile); Xaa at res.79=(Tyr or Phe); Xaa at res.80=(Phe, Tyr, Leu or His); Xaa at res.81=(Asp, Asn or Leu); Xaa at res.82=(Asp, Glu, Asn or Ser); Xaa at res.83=(Ser, Gln, Asn, Tyr or Asp); Xaa at res.84=(Ser, Asn, Asp, Glu or Lys); Xaa at res.85=(Asn, Thr or Lys); Xaa at res.87=(Ile, Val or Asn); Xaa at res.89=(Lys or Arg); Xaa at res.90=(Lys, Asn, Gln, His or Val); Xaa at res.91=(Tyr or His); Xaa at res.92=(Arg, Gln, Glu or Pro); Xaa at res.93=(Asn, Glu or Asp); Xaa at res.95=(Val, Thr, Ala or Ile); Xaa at res.97=(Arg, Lys, Val, Asp or Glu); Xaa at res.98=(Ala, Gly, Glu or Ser); Xaa at res.100=(Gly or Ala); and Xaa at res.102=(His or Arg).

Particularly useful sequences for use as morphogens in this invention include the C-terminal domains, e.g., the C-terminal 96–102 amino acid residues of Vgl, Vgr-1, DPP, OP-1, OP-2, CBMP-2A, CBMP-2B, GDF-1 (see Table II, below, and Seq. ID Nos. 5–14), as well as proteins comprising the C-terminal domains of 60A, BMP3, BMP5 and BMP6 (see Seq. ID Nos. 24–28), all of which include at least the conserved six or seven cysteine skeleton. In addition, biosynthetic constructs designed from the generic sequences, such as COP-1, 3–5, 7, 16, disclosed in U.S. Pat. No. 5,011,691, also are useful. Other sequences include the inhibins/activin proteins (see, for example, U.S. Pat. Nos. 4,968,590 and 5,011,691). Accordingly, other useful sequences are those sharing at least 70% amino acid sequence homology or "similarity", and preferably 80% homology or similarity with any of the sequences above. These are anticipated to include allelic and species variants and mutants, and biosynthetic muteins, as well as novel members of this morphogenic family of proteins. Particularly envisioned in the family of related proteins are those proteins exhibiting morphogenic activity and wherein the amino acid changes from the preferred sequences include conservative changes, e.g., those as defined by Dayoff et al., *Atlas of Protein Sequence and Structure;* vol. 5, Suppl. 3, pp. 345–362, (M. O. Dayoff, ed., Nat'l BioMed. Research Fdn., Washington, D.C. 1979). As used herein, potentially useful sequences are aligned with a known morphogen sequence using the method of Needleman et al. ((1970) *J.Mol.Biol.* 48:443–453) and identities calculated by the Align program (DNAstar, Inc.). "Homology" or "similarity" as used herein includes allowed conservative changes as defined by Dayoff et al.

The currently most preferred protein sequences useful as morphogens in this invention include those having greater than 60% identity, preferably greater than 65% identity, with the amino acid sequence defining the conserved six cysteine skeleton of hOP1 (e.g., residues 43–139 of Seq. ID No. 5). These most preferred sequences include both allelic and species variants of the OP-1 and OP-2 proteins, including the Drosophila 60A protein. Accordingly, in another preferred aspect of the invention, useful morphogens include active proteins comprising species of polypeptide chains having the generic amino acid sequence herein referred to as "OPX" (Seq. ID No. 29), which defines the seven cysteine skeleton and accommodates the homologies between the various identified species of OP1 and OP2. As described therein, each Xaa at a given position independently is selected from the residues occurring at the corresponding position in the C-terminal sequence of mouse or human OP1 or OP2 (see Seq. ID Nos. 5–8 and/or Seq. ID Nos. 16–23).

The morphogens useful in the methods, compositions and devices of this invention include proteins comprising any of the polypeptide chains described above, whether isolated from naturally-occurring sources, or produced by recombinant DNA or other synthetic techniques, and includes allelic and species variants of these proteins, naturally-occurring or biosynthetic mutants thereof, as well as various truncated and fusion constructs. Deletion or addition mutants also are envisioned to be active, including those which may alter the conserved C-terminal cysteine skeleton, provided that the alteration does not functionally disrupt the relationship of these cysteines in the folded structure. Accordingly, such active forms are considered the equivalent of the specifically described constructs disclosed herein. The proteins may include forms having varying glycosylation patterns, varying N-termini, a family of related proteins having regions of amino acid sequence homology, and active truncated or mutated forms of native or biosynthetic proteins, produced by expression of recombinant DNA in host cells.

The morphogenic proteins can be expressed from intact or truncated cDNA or from synthetic DNAs in procaryotic or eucaryotic host cells, and purified, cleaved, refolded, and dimerized to form morphogenically active compositions.

Currently preferred host cells include *E. coli* or mammalian cells, such as CHO, COS or BSC cells. A detailed description of the morphogens useful in the methods, compositions and devices of this invention is disclosed in copending U.S. patent application Ser. Nos. 752,764, filed Aug. 30, 1991, and 667,724, filed Mar. 11, 1991, the disclosures of which are incorporated herein by reference.

Thus, in view of this disclosure, skilled genetic engineers can isolate genes from cDNA or genomic libraries of various different species which encode appropriate amino acid sequences, or construct DNAs from oligonucleotides, and then can express them in various types of host cells, including both procaryotes and eucaryotes, to produce large quantities of active proteins capable of stimulating the morphogenesis of, and/or inhibiting damage to, periodontal tissue.

Other features and advantages of the invention will be apparent from the following description of the preferred embodiments, and from the claims.

BRIEF DESCRIPTION OF THE DRAWINGS

The foregoing and other objects and features of this invention, as well as the invention itself, may be more fully understood from the following description, when read together with the accompanying drawings, in which.

DETAILED DESCRIPTION

It has been discovered that the morphogens described herein can stimulate periodontal tissue formation, including regenerating lost or damaged periodontal ligament and/or cementum. The invention may be used for tooth implant integration as well as to inhibit and/or repair periodontal tissue loss due to disease or mechanical injury. The invention is practiced using a morphogen or morphogen-stimulating agent, as defined herein, and according to the procedures described herein.

Provided below is a description of tooth anatomy and useful morphogens, including methods for their production and formulation, as well as exemplary, non-limiting examples which (1) demonstrate the suitability of the morphogens described herein in the methods of the invention, and (2) provide assays with which to test candidate morphogens for their efficacy.

I. Tooth Anatomy

Figure 1:
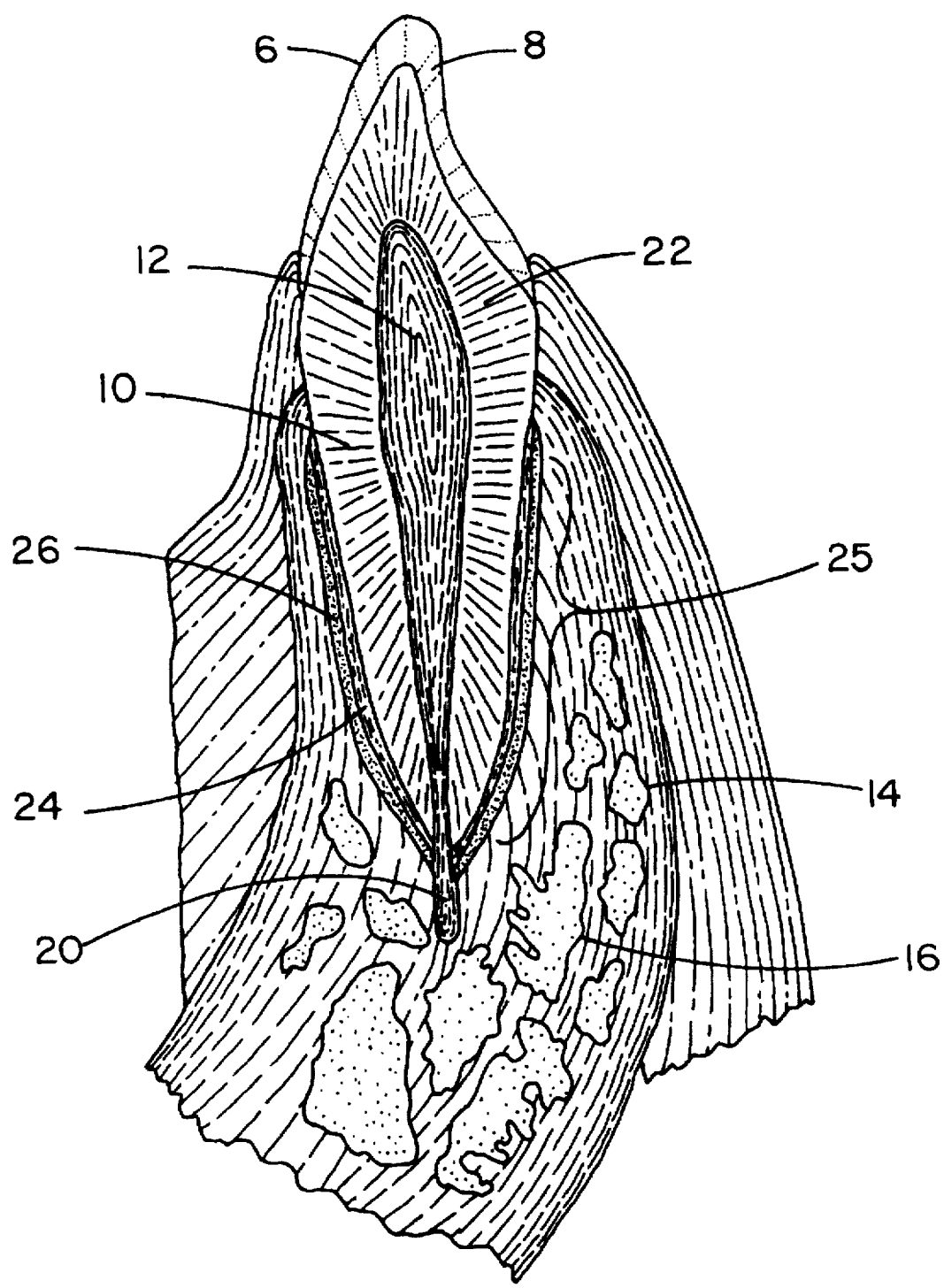
FIG. 1 is a schematic illustration of a healthy tooth in the tooth socket.

A vertical section of a tooth in the tooth socket is shown schematically in FIG. 1. The crown 6 of the tooth is composed of enamel 8 and dentin 22. The pulp chamber 12 is seen in the interior of the crown 6 and the center of the root 10; it extends downward into the bony area 14, 16, 18 and opens by a minute orifice, the apical foramen 20, at the extremity of the root 10. The pulp chamber 12 contains dental pulp, a loose connective tissue richly supplied with vessels and nerves, which enter the cavity through the apical foramen 20. Some of the cells of the pulp, i.e., odontoblasts, the precursors of dentin 22, are arranged as a layer on the wall of the pulp chamber 12. During development of the tooth, odontoblasts are columnar, but later, after the dentin 22 is fully formed, they become flattened and resemble osteoblasts.

The solid portion of the mature tooth includes dentin 22, enamel 8, and a thin layer of cementum 24, which is disposed on the surface of the root 25. Enamel 8 is formed during development of the tooth from amyloblasts, and cementum 24 is formed from cementoblasts. In a fully developed tooth, the principal mass of the tooth comprises dentin 22, which is made up of hydroxyapatite crystals embedded in a strong meshwork of collagen fibers. The dentin includes a number of minute wavy and branching tubes called dental canaliculi, embedded in a dense homogeneous substance, the matrix. The dental canaliculi are parallel with one another and open at their inner ends into the pulp chamber 12. The dentin matrix is translucent and comprises the majority of the inorganic mass of the dentin. It includes a number of fine fibrils, which are continuous with the fibrils of the dental pulp. After the organic matter has been removed by steeping a tooth in weak acid, the remaining organic matter may be torn into laminae that run parallel with the pulp chamber 12 across the direction of the tubes.

The cementum 24 is disposed as a thin mineralized layer covering the tooth root. It extends from where the enamel terminates to the apex of each root, where it is usually very thick. Cementum resembles bone in structure and chemical composition in that it contains, sparingly, the lacunae and canaliculi that characterize true bone; in the thicker portions of the cementum, the lamellae and Haversian canals peculiar to bone are also found. As a result of aging, the cementum increases in thickness and the pulp chamber also becomes partially filled with a hard substance that is intermediate in structure between dentin and bone. It appears to be formed by a slow conversion of the dental pulp, which shrinks or even disappears.

The periodontal ligament, or periodontal membrane 26, is the layer of periodontal tissue which forms a cushion between the cementum 24 and the bone 14, 16, 18; it holds the tooth in position by suspending it in the socket (alveolus) of the jawbone. The periodontal ligament is a highly organized tissue which is formed from periodontal fibroblasts. It organizes the collagen fibers which pass directly from the bone of the jaw into the cementum.

II. Useful Morphogens

As defined herein a protein is morphogenic if it is capable of inducing the developmental cascade of cellular and molecular events that culminate in the formation of new, organ-specific tissue and comprises at least the conserved C-terminal six cysteine skeleton or its functional equivalent (see supra). Specifically, the morphogens generally are capable of all of the following biological functions in a morphogenically permissive environment: stimulating proliferation of progenitor cells; stimulating the differentiation of progenitor cells; stimulating the proliferation of differentiated cells; and supporting the growth and maintenance of differentiated cells, including the "redifferentiation" of transformed cells. Details of how the morphogens useful in the method of this invention first were identified, as well as a description on how to make, use and test them for morphogenic activity are disclosed in U.S. Ser. No. 752,764, filed Aug. 30, 1991, the disclosure of which is incorporated hereinabove by reference. As disclosed therein, the morphogens may be purified from naturally-sourced material or recombinantly produced from procaryotic or eucaryotic host cells, using the genetic sequences disclosed therein. Alternatively, novel morphogenic sequences may be identified following the procedures disclosed therein.

Particularly useful proteins include those which comprise the naturally derived sequences disclosed in Table II. Other useful sequences include biosynthetic constructs such as those disclosed in U.S. Pat. No. 5,011,691, the disclosure of which is incorporated herein by reference (e.g., COP-1, COP-3, COP-4, COP-5, COP-7, and COP-16).

Accordingly, the morphogens useful in the methods and compositions of this invention also may be described by morphogenically active proteins having amino acid sequences sharing 70% or, preferably, 80% homology (similarity) with any of the sequences described above, where "homology" is as defined herein above.

The morphogens useful in the method of this invention also can be described by any of the 6 generic sequences described herein (Generic Sequences 1, 2, 3, 4, 5 and 6). Generic sequences 1 and 2 also may include, at their N-terminus, the sequence Cys Xaa Xaa Xaa Xaa   (Seq. ID No. 15)
 1            5

Table II, set forth below, compares the amino acid sequences of the active regions of native proteins that have been identified as morphogens, including human OP-1 (hOP-1, Seq. ID Nos. 5 and 16–17), mouse OP-1 (mOP-1, Seq. ID Nos. 6 and 18–19), human and mouse OP-2 (Seq. ID Nos. 7, 8, and 20–23), CBMP2A (Seq. ID No. 9), CBMP2B (Seq. ID No. 10), BMP3 (Seq. ID No. 26), DPP (from Drosophila, Seq. ID No. 11), Vgl, (from Xenopus, Seq. ID No. 12), Vgr-1 (from mouse, Seq. ID No. 13), GDF-1 (from mouse, Seq. ID Nos. 14, 32 and 33), 60A protein (from Drosophila, Seq. ID Nos. 24 and 25), BMP5 (Seq. ID No. 27) and BMP6 (Seq. ID No. 28). The sequences are aligned essentially following the method of Needleman et al. (1970) *J. Mol. Biol.*, 48:443–453, calculated using the Align Program (DNAstar, Inc.) In the table, three dots indicates that the amino acid in that position is the same as the amino acid in hOP-1. Three dashes indicates that no amino acid is present in that position, and are included for purposes of illustrating homologies. For example, amino acid residue 60 of CBMP-2A and CBMP-2B is "missing". Of course, both these amino acid sequences in this region comprise Asn-Ser (residues 58, 59), with CBMP-2A then comprising Lys and Ile, whereas CBMP-2B comprises Ser and Ile.

TABLE II

| | | | | | | | | |
|---|---|---|---|---|---|---|---|---|
| hOP-1 | Cys | Lys | Lys | His | Glu | Leu | Tyr | Val |
| mOP-1 | ... | ... | ... | ... | ... | ... | ... | ... |
| hOP-2 | ... | Arg | Arg | ... | ... | ... | ... | ... |
| mOP-2 | ... | Arg | Arg | ... | ... | ... | ... | ... |
| DPP | ... | Arg | Arg | ... | Ser | ... | ... | ... |
| Vgl | ... | ... | Lys | Arg | His | ... | ... | ... |
| Vgr-1 | ... | ... | ... | ... | Gly | ... | ... | ... |
| GDF-1 | Gln | ... | Glu | Asp | ... | ... | ... | Asp |
| 60A | ... | ... | ... | ... | ... | Ile | ... | Lys |
| BMP5 | ... | ... | ... | ... | ... | ... | ... | ... |
| BMP6 | ... | ... | ... | Trp | ... | ... | ... | ... |
| | 90 | | | | 95 | | | |
| hOP-1 | Ala | Cys | Gly | Cys | His | | | |
| mOP-1 | ... | ... | ... | ... | ... | | | |
| hOP-2 | ... | ... | ... | ... | ... | | | |
| mOP-2 | ... | ... | ... | ... | ... | | | |
| DPP | Gly | ... | ... | ... | Arg | | | |
| Vgl | Glu | ... | ... | ... | Arg | | | |
| Vgr-1 | ... | ... | ... | ... | ... | | | |
| CBMP-2A | Gly | ... | ... | ... | Arg | | | |
| CBMP-2B | Gly | ... | ... | ... | Arg | | | |
| BMP3 | Ser | ... | Ala | ... | Arg | | | |
| GDF-1 | Glu | ... | ... | ... | Arg | | | |
| 60A | Ser | ... | ... | ... | ... | | | |

TABLE II-continued

| | | | | | |
|---|---|---|---|---|---|
| BMP5 | Ser | ... | ... | ... | ... |
| BMP6 | ... | ... | 100 | ... | ... |

**Between residues 56 and 57 of BMP3 is a Val residue; between residues 43 and 44 of GDF-1 lies the amino acid sequence Gly-Gly-Pro-Pro.

As is apparent from the foregoing amino acid sequence comparisons, significant amino acid changes can be made within the generic sequences while retaining the morphogenic activity. For example, while the GDF-1 protein sequence depicted in Table II shares only about 50% amino acid identity with the hOP1 sequence described therein, the GDF-1 sequence shares greater than 70% amino acid sequence homology (or "similarity") with the hOP1 sequence, where "homology" or "similarity" includes allowed conservative amino acid changes within the sequence as defined by Dayoff, et al., *Atlas of Protein Sequence and Structure* vol.5, supp.3, pp.345–362, (M. O. Dayoff, ed., Nat'l BioMed. Res. Fd'n, Washington D.C. 1979.)

The currently most preferred protein sequences useful as morphogens in this invention include those having greater than 60% identity, preferably greater than 65% identity, with the amino acid sequence defining the conserved six cysteine skeleton of hOP1 (e.g., residues 43–139 of Seq. ID No. 5). These most preferred sequences include both allelic and species variants of the OP-1 and OP-2 proteins, including the Drosophila 60A protein. Accordingly, in still another preferred aspect, the invention includes morphogens comprising species of polypeptide chains having the generic amino acid sequence referred to herein as "OPX", which defines the seven cysteine skeleton and accommodates the identities between the various identified mouse and human OP1 and OP2 proteins. OPX is presented in Seq. ID No. 29. As described therein, each Xaa at a given position independently is selected from the residues occurring at the corresponding position in the C-terminal sequence of mouse or human OP1 or OP2 (see Seq. ID Nos. 5–8 and/or Seq. ID Nos. 16–23).

Alternatively, an effective amount of an agent capable of stimulating endogenous morphogen levels may be administered by any of the routes described herein below. For example, an agent capable of stimulating morphogen production and/or secretion from periodontal tissue cells, alveolar bone tissue cells in the fresh tooth socket, or dentin tissue, may be provided to a mammal, e.g., by direct administration of the morphogen-stimulating agent to the tooth root and/or tooth socket bone surface. Alternatively, the morphogen-stimulating agent may induce morphogen expression and/or secretion at a distant site (e.g., at a tissue locus other than periodontal, dental or alveolar bone tissue), with the expressed morphogen targeting itself to periodontal tissue. A method for identifying and testing agents capable of modulating the levels of endogenous morphogens in a given tissue is described generally herein in Example 3, and in detail in copending U.S. Ser. No. 08/278,729, filed Aug. 28, 1992 and U.S. Ser. No. 752,859, filed Aug. 30, 1991, the disclosures of which are incorporated herein by reference.

Briefly, candidate compounds can be identified and tested by incubating the compound in vitro with a test tissue or cells thereof, for a time sufficient to allow the compound to affect the production, i.e., the expression and/or secretion, of a morphogen produced by the cells of that tissue. Here, suitable tissue, or cultured cells of a tissue, preferably comprise periodontal fibroblasts, cementoblasts, odontoblasts or osteoblasts.

III. Formulations and Methods for Administration

1. Therapeutic Agent Considerations

The morphogens may be provided to the tooth root and/or tooth socket surface by any suitable means. Preferably, the morphogen, or a morphogen-stimulating agent, (collectively, the therapeutic agent) is provided directly to the tissue surface by topical administration. Alternatively, the therapeutic agent may be provided to the tissue by, for example, local injection. While not currently preferred, systemic injection also may be a viable administration route for certain applications, such as periodontal tissue maintenance in older adults, immuno-suppressed individuals, or others at chronic risk for periodontal tissue loss. A detailed description of considerations for systemic administration, including oral and parenteral administration, is disclosed, for example, in copending U.S. Ser. No. 08/445,467, incorporated hereinabove by reference.

Where the therapeutic agent is provided directly to the tooth socket, the therapeutic agent may be provided to the socket surface as part of a biocompatible formulation that may be a liquid, gel or solid. The therapeutic agent further may be dispersed in and associated with a carrier capable of maintaining the morphogen at the administered locus. Useful formulations include viscous compositions. Biocompatible compositions that increase the viscosity of the formulation include glycerol, polyalkylene glycols such as polyethylene glycol, oils of vegetable origin, hydrogenated naphthalenes, and the like.

The formulation also may include an in vivo bioresorbable carrier material that acts as a controlled release delivery vehicle. Useful carriers may include biocompatible, preferably biodegradable structural components from, e.g., an extracellular matrix, such as collagen, laminin, hyaluronic acid, and the like, or polymeric materials, such as polylactic, polybutyric and polyglycolic acids. The carrier also may comprise an acellular tissue matrix, substantially depleted in nonstructural components, such as a demineralized, guanidine-extracted dentin, periodontal ligament or cementum matrix. Details for preparing such matrices are disclosed in U.S. Ser. No. 752,764, incorporated hereinabove by reference. Other useful controlled release carriers in which the therapeutic agent may be dispersed are described in U.S. Pat. Nos. 4,975,526 and 4,919,939, the disclosures of which are incorporated herein by reference.

Where the morphogen is to be provided to a tooth root surface, it may be formulated in a composition for controlled delivery as described above and applied topically to the tooth root surface as described below. Alternatively, or in addition, the therapeutic agent may be dispersed in a liquid formulation into which at least the tooth root surface is placed and the liquid lyophilized to adsorb the therapeutic agent onto the tooth surface.

Where the agent is administered to inhibit periodontal tissue loss and/or to regenerate periodontal tissue surrounding an implanted tooth, the agent may be provided to the area between the tooth and gum (gingiva) by injection or by topical application.

Where the morphogen is to be provided directly (e.g., locally, as by injection, e.g., to a periodontal or alveolar tissue site), the morphogen preferably comprises part of an aqueous solution which also may contain a carrier material. The solution is physiologically acceptable so that in addition to delivery of the desired morphogen to the patient, the solution does not otherwise adversely affect the patient's electrolyte and volume balance. The aqueous medium for the morphogen thus may comprise normal physiologic saline (0.85% NaCl, 0.15M), pH 7–7.4. The aqueous solution containing the morphogen can be made, for example, by dissolving the protein in 50% ethanol containing acetonitrile in 0.1% trifluoroacetic acid (TFA) or 0.1% HCl, or equivalent solvents. One volume of the resultant solution then is added, for example, to ten volumes of phosphate buffered saline (PBS), which further may include 0.1–0.2% human serum albumin (HSA). The resultant solution preferably is vortexed extensively. If desired, a given morphogen may be made more soluble in the solution by association with a suitable molecule. For example, the pro form of the morphogenic protein comprises a species that is soluble in physiological solutions. In fact, the endogenous protein is thought to be transported (e.g., secreted and circulated) in this form. This soluble form of the protein may be obtained from the culture medium of morphogen-secreting mammalian cells. Alternatively, a soluble species may be formulated by complexing the mature dimer (or an active fragment thereof) with part or all of a pro domain. Other components, including various serum proteins, also may be useful.

Finally, the morphogens or morphogen-stimulating agents provided herein may be administered alone or in combination with other molecules, particularly symptom alleviating cofactors. Useful pharmaceutical cofactors include antiseptics, antibiotics, anaesthetics and analgesics. Preferred antiseptics for use in the present system include chlorhexidine and tibezonium iodide; preferred antibiotics include tetracycline, aminoglycosides such as neomycin, gentamycin, kanamycin, tobramycin, netilmicin, sisomicin, amicamycin, their sulfates or other derivatives, macrolides such as erythromycin, its salts and other derivatives, spiramycin, josamicin or miocamicin, penicillins such as ampicillin, amoxicillin and the like, and cephalosporins, for example, cefaclor, cefadroxil, cefazolin, cefoperazone, cefotaxime, cephalothin, cefalexin, ceforanide, cefonicide or ceftriaxone. Preferred anaesthetics/analgesics include amide-type local anaesthetics such as lidocaine, mepivacaine, pyrrocaine, bupivacaine, prilocaine, etidocaine, or other widely used anaesthetics such as procaine.

Other cofactors include non-steroidal anti-inflammatory agents. However, the morphogens described herein themselves modulate the body's imflammatory/immune response to an initial tissue injury. Specifically, and as described in detail in U.S. Ser. No. 08/445,467 disclosed hereinabove by reference, in the presence of a morphogen, progenitor inflammatory effector cells induced to migrate to a site of tissue injury do not become significantly activated. Without being limited to any given theory, it is thought that, in the presence of the morphogen, damaged tissue is induced to undergo a recapitulation of tissue morphogenesis, where progenitor cells are induced to proliferate and differentiate in a tissue-specific manner, and new, functional, organized tissue is formed to replace the damaged or lost tissue, rather than disorganized, fibrous scar tissue.

The formulated compositions contain therapeutically effective amounts of the morphogen, e.g., amounts which provide appropriate concentrations of the morphogen to the tooth surface for a time sufficient to stimulate growth and development of periodontal tissues, including morphogenesis of periodontal ligament and/or cementum, and/or to substantially inhibit periodontal tissue loss.

As will be appreciated by those skilled in the art, the concentration of the compounds described in a therapeutic composition will vary depending upon a number of factors, including the biological efficacy of the selected morphogen, the chemical characteristics (e.g., hydrophobicity) of the compounds employed, the formulation of the compound excipients, the administration route, and the treatment envisioned. The preferred dosage to be administered also is likely to depend on such variables such as the condition of the tissues within the tooth socket, the size of the tooth or tooth socket, the length of time after tooth loss, extent of periodontal tissue loss and the overall health status of the particular patient. The amount of morphogen applied also will depend on the tooth size. In general, 0.1–1000 µg of morphogen are sufficient with 1–100 µg being preferable. For example, for a large tooth, e.g., an incisor or large molar, about 10–100 µg, and preferably 50 µg of morphogen, may be used to advantage; a medium tooth may be treated with approximately 5–50 µg, and preferably 25 µg; and a small tooth, with approximately 1–25, preferably 5–10 µg morphogen. No obvious morphogen induced pathological lesions are induced when mature morphogen (e.g., OP-1, 20 µg) is administered daily to normal growing rats for 21 consecutive days. Moreover, 10 µg systemic injections of morphogen (e.g., OP-1) injected daily for 10 days into normal newborn mice does not produce any gross abnormalities.

2. Tooth Preparation

Tooth loss may be repaired by implanting a viable tooth having a healthy root and pulp system or by implanting a tooth prosthesis. The prosthesis may be a tooth from which the root has been removed and replaced with a biocompatible, biologically inert material, e.g., as typically is replaced in a root canal procedure, or may be a completely synthetic prosthesis coated, for example, with a porous material to enhance tooth integration in the tooth socket. Useful prosthesis coating materials include collagen fibers, ceramics and metals, such as titanium oxide. The root of the implanted tooth first may be partially demineralized as described below. Alternatively, a clean, mineralized natural tooth or dentin-containing prosthetic tooth may be implanted.

A tooth to be implanted first is obtained, e.g., by loss or removal of a natural tooth from the tooth socket, e.g., using standard tooth extraction means well known to one skilled in the dentistry art. Alternatively, an allogenic tooth may be obtained from a tooth bank. The natural, mineralized tooth or tooth root may be coated as is with a morphogen and implanted as described below. Alternatively, the mineralized, natural tooth root surface first may be scored or scraped to expose dentin tissue beneath the enamel. Natural, mineralized teeth also may be treated briefly with an acidic solution (e.g., sodium citrate, about pH 3.5) to remove a thin external layer, e.g., about 1–5 cells in thickness from at least the root surface. Preferred treatment times are from about 0.5 to 5 minutes. The treated teeth preferably then are washed, dried and coated with morphogen as described below. Alternatively, the tooth root portion may be at least partially demineralized according to any conventional procedure prior to implantation. A currently preferred demineralization method is to soak the tooth in a demineralizing solution for a length of time sufficient to remove at least some mineral components from the tooth. For example, at least the root portion of the tooth may be placed in a volume, e.g., 0.025–1 liter of a demineralizing agent such as hydrochloric acid (HCl) at a cool temperature for a time sufficient to achieve partial demineralization, e.g., 0.5–0.6M HCl at 4° C. for a prescribed number of minutes (e.g., preferably within the range of about 10–200 minutes.) Essentially complete demineralization may be achieved by acid exposure for 1–7 days. If desired, several changes of the demineralizing agent may be performed. The partially demineralized tooth will be of the same shape as prior to demineralization, but will weigh less due to the absence of the mineral content. The tooth then may be dried by lyophilization.

The tooth or tooth prosthesis may be treated with morphogenic protein as follows. The morphogen may be applied to the tooth or tooth prosthesis root surface by any means known in the art for adsorbing a protein to a surface. A currently preferred method is to suspend the morphogen in a small volume sufficient to cover the tooth surface, e.g., 200–300 µl, freeze the tooth in solution, and then lyophilize the frozen liquid. A currently preferred solution is ethanol (e.g. 50%) or acetonitrile/trifluroactic acid (TFA), other solutions include HCL/TFA, buffered saline, and the like. Alternatively, or in addition, the therapeutic agent may be provided to the tooth root surface dispersed in a suitable carrier material as described above. Similarly, and as described above, the therapeutic agent may be provided to the tooth socket surface and the tooth to be implanted embedded in the morphogen composition on the socket surface. Also as described above, the morphogen may be provided to the tooth root surface in admixture with one or more cofactors.

The tooth then is implanted into a fresh or surgically prepared tooth socket. A surgically prepared surface is prepared by extracting the tooth and removing any scar or other undesired fibrous tissue built up in the socket by standard mechanical and/or chemical procedures well known on the surgical and dental arts. The tooth then is implanted in the site using standard dental and surgical procedures.

The implanted tooth is allowed to grow in the prepared socket for a time sufficient to allow the periodontium to regenerate, e.g., one to several months. The integrity and health of the integrated tooth then may be assessed by a dentist by radiography and visual examination.

For experimental purposes, the integration of an implanted tooth following morphogen treatment can be assessed for integrity and health by removing the entire mandibular area, including the tooth socket and tooth, and examining cross sections of the mandibular area. 5–10 µm cross sections may be prepared for histological evaluation by standard histology procedures, e.g., fixing tissue with formalin, preparing sections for slides and staining with eosin and hematoxylin. The growth and integrity of hard tissues, such as bone, cementum and dentin, also can evaluated radiographically.

Finally, and as described in detail in U.S. Ser. No. 752,674 and in Example 2 below, the morphogens of this invention also induce dentin tissue morphogenesis when provided to an area of lost or damaged dentin. Accordingly, using the procedures described herein and in U.S. Ser. No. 752,674, the morphogen described herein also may be used to repair and regenerate damaged and/or lost dentin tissue in an implanted tooth.

IV. EXAMPLES

Example 1

Experimental Regeneration of Peridontium in a Dog Model

The following experiment demonstrates successful integration of an implanted demineralized, protein-extracted morpohgen-treated tooth in a mammal. Premolar teeth were extracted from a dog and divided into three experimental groups: (a) demineralized teeth; (b) demineralized and guanidine extracted teeth; and (c) demineralized, guanidine extracted, and morphogen-treated teeth. Teeth from each group were tested in "fresh" sockets, e.g., tooth sockets from which the teeth had just been removed, as well as surgically prepared sockets, e.g., sockets from which teeth had been extracted 2 months previously and in which scar tissue had formed. These "healed" sockets were surgically prepared for tooth implantation by removing (e.g., by scraping) scar tissue build up to reveal fresh alveolar bone.

The teeth from all three groups were completely demineralized by placing them in 4 liters of 0.5M HCl at 4° C. for 5 days. The 0.5M HCl solution was changed every 24 hours during the 5 day period. The teeth then were washed in 4 liters of deionized water at 4° C. for 5 days. The water solution was also changed every 24 hours during the 5 day period. Teeth from group (a) then were lyophilized until dry and set aside and maintained at 4° C. until ready for use.

Teeth from groups (b) and (c) then were protein-extracted by multiple extractions in 6M quanidine Hcl, followed by washes with distilled water. Specifically, the teeth were placed in in 2–4 liters of 6M guanidine-HCl/Tris HCl pH 7.0 at 4° C. for 72 hours; then washed and further extracted in 200 ml of the guanidine-HCl solution for 4 hours. The teeth were washed again with 4 liters of distilled $dH_2O$ at 4° C. for 48 hours, and 4 liters of $dH_2O$ for an additional 12 hours with 3 changes of $dH_2O$. The teeth were then lyophilized until dry. Teeth from group (b) were then set aside and maintained at 4° C. until ready for use.

Teeth from group (c) then were treated with the morphogen OP-1 as follows. 1.15 mg of OP-1 was resuspended in 4 ml of 47.5% ethanol/0.09% trifluoroacetic acid (TFA). The concentration was determined to be 0.273 mg/ml. Approximately 50 µg of OP-1 (183 µl of the OP-1 solution) was dispensed into an eppendorf tube, and the total volume brought to 300 µl of 47.5% ethanol/0.09% TFA. Each tooth then was placed in an eppendorf tube such that the OP-1 solution just covered the tooth. The tube was placed at −70° C. until the OP-1 solution was frozen, and lyophilized until dry. During lyophilization, care was taken to keep the tube cold. Approximately 50–70% of the OP-1 can be expected to remain in or on the tooth after lyophilization.

The teeth from each of groups (a), (b), and (c) were then implanted into a freshly prepared tooth socket or surgically prepared socket using standard dental surgery procedures known in the art.

The implanted teeth in all three groups were allowed to remain in the socket for two months. The dog then was sacrificed, the mandible cross-sectioned and x-rayed, and histology performed. The results are described below and follows.

Figure 2A:
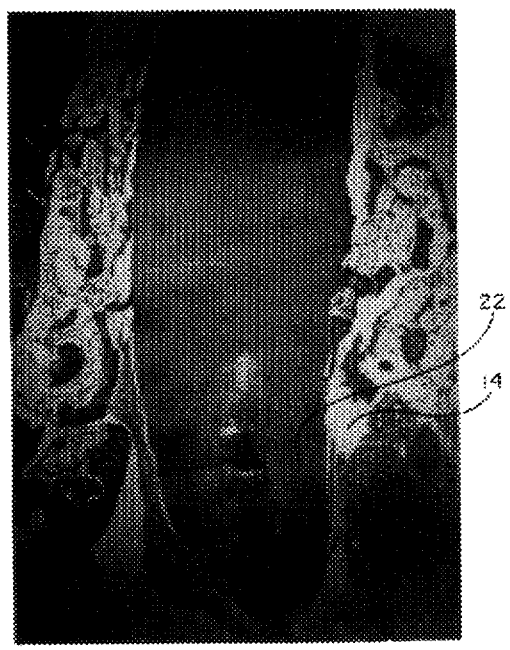
FIG. 2 (A and B) are photomicrographs demonstrating the effect of morphogen (2A) or carrier alone (2B) on periodontal tissue regeneration in a surgically prepared canine tooth socket.

Ankylosis formed in the group (a) implants, where demineralized tooth matrix was implanted alone. Cross-sections of the group (a) mandible revealed that the demineralized tooth was surrounded by bone directly attaching to the root or dentin surface. In addition, there was little new tissue growth between the tooth and the bone. Representative histology is illustrated in the photomicrograph of FIG. 2A where bone tissue 14 grows directly into dental tissue 22 in the implanted tooth.

In the group (b) implants, cross-sections revealed formation of unorganized fibrous tissue around the implanted demineralized, guanidine extracted tooth. The periodontal ligament was loose and disorganized, as was the surrounding bony tissue. Examination of the tooth root surface where cementum matrix normally appears revealed resorption of cementum in the upper coronal surface of the tooth. Histological sections also revealed inflammation as evidenced by the presence of macrophages.

Figure 2B:
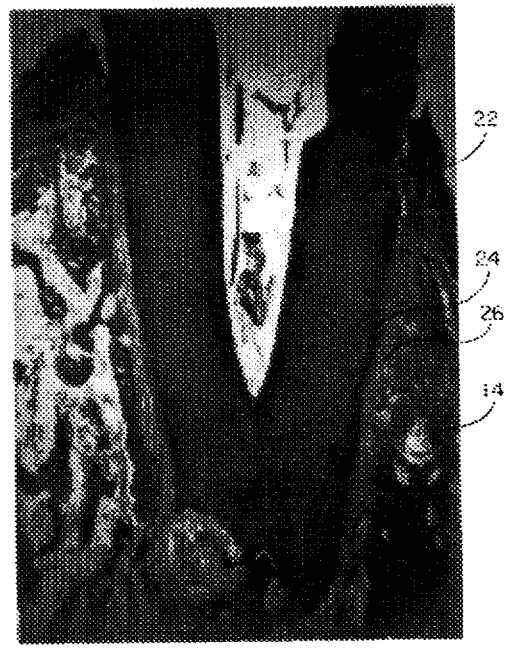

As is evident in FIG. 2b, group (c) implant cross-sections revealed formation of newly formed, organized cementum 24 and periodontal ligament tissue 26 around the morphogen-treated tooth matrix, and growth of new bone connecting the newly formed periodontium to the mandible. The tooth was firmly anchored in the tooth socket. The tissues surrounding the tooth, i.e., the newly-formed cementum growing perpendicular to the newly-formed periodontal ligament, and the alveolar bony tissue, all were healthy and organized much as the tooth and tooth socket shown schematically in FIG. 1. The newly-formed cementum comprised immature columnar cell layers which were beginning to flatten into mature cementoblasts, and the newly-formed periodontal ligament comprised a thick layer of tissue to anchor and cushion the tooth within the tooth socket.

The results of this experiment demonstrate that morphogens promote tooth integration into a tooth socket, and induce morphogenesis of periodontium, including morphogenesis of the regeneration and formation of the periodontium, new cementum and periodontal ligament.

Without being limited to any particular theory, the morphogens may act in the tooth socket environment by inducing a differentiation of primary fibroblasts on the alveolar surface to differentiate into cementoblasts which then induct other primary fibroblasts to form periodontal ligament.

Example 2

Morphogen-Induced Dentinogenesis

The example presented below demonstrates the efficacy of morphogens in inducing dentin tissue morphogenesis in an animal model. Further details of the experiment and the implications of this biological activity of morphogens are diclosed in U.S. Ser. No. 752,674.

To date, the unpredictable response of dental pulp tissue to injury is a basic clinical problem in dentistry. Cynomolgus monkeys were chosen as primate models as monkeys are presumed to be more indicative of human dental biology than models based on lower non-primate mammals.

Using standard dental surgical procedures, small areas (e.g., 2 mm) of dental pulps were surgically exposed by removing the enamel and dentin immediately above the pulp (by drilling) of sample teeth, performing a partial amputation of the coronal pulp tissue, inducing hemostasis, application of the pulp treatment, and sealing and filling the cavity by standard procedures.

Pulp treatments used were: OP-1 dispersed in a carrier matrix; carrier matrix alone and no treatment. Twelve teeth per animal (four for each treatment) were prepared, and two animals were used. At four weeks, teeth were extracted and processed histologically for analysis of dentin formation, and/or ground to analyze dentin mineralization. Morphogen treatment produced dramatic effects: Control treatments with carrier alone (PBS) and showed little or no reparation of the lost tissue. By contrast, morphogen-treated teeth showed significant dentin tissue formation in the area where dentin tissue had been surgically removed. The experimental results show that morphogen treatment reliably induced formation of reparative or osteodentin bridges on surgically exposed healthy dental pulps. By contrast, pulps treated with carrier matrix alone, or not treated, failed to form reparative dentin.

Example 3

Screening Assay for Candidate Compounds which Alter Endogenous Morphogen Levels

Candidate compound(s) which may be administered to affect the level of a given morphogen hay be found using the following screening assay, in which the level of morphogen production by a cell type which produces measurable levels of the morphogen is determined with and without incubating the cell in culture with the compound, in order to assess the effects of the compound on the cell. This can be accomplished by detection of the morphogen either at the protein or RNA level. A more detailed description also may be found in U.S. Ser. No. 752,861, incorporated hereinabove by reference.

3.1 Growth of Cells in Culture

Cell cultures of kidney, adrenals, urinary bladder, brain, or other organs, may be prepared as described widely in the literature. For example, kidneys may be explanted from neonatal or new born or young or adult rodents (mouse or rat) and used in organ culture as whole or sliced (1—4 mm) tissues. Primary tissue cultures and established cell lines, also derived from kidney, adrenals, urinary, bladder, brain, mammary, or other tissues may be established in multiwell plates (6 well or 24 well) according to conventional cell culture techniques, and are cultured in the absence or presence of serum for a period of time (1–7 days). Cells may be cultured, for example, in Dulbecco's Modified Eagle medium (Gibco, Long Island, N.Y.) containing serum (e.g., fetal calf serum at 1%–10%, Gibco) or in serum-deprived medium, as desired, or in defined medium (e.g., containing insulin, transferrin, glucose, albumin, or other growth factors).

Samples for testing the level of morphogen production includes culture supernatants or cell lysates, collected periodically and evaluated for OP-1 production by immunoblot analysis (Sambrook et al., eds., 1989, Molecular Cloning, Cold Spring Harbor Press, Cold Spring Harbor, N.Y.), or a portion of the cell culture itself, collected periodically and used to prepare polyA+ RNA for RNA analysis. To monitor de novo OP-1 synthesis, some cultures are labeled according to conventional procedures with an $^{35}$S-methionine/$^{35}$S-cysteine mixture for 6–24 hours and then evaluated for OP-1 synthesis by conventional immunoprecipitation methods.

3.2 Determination of Level of Morphogenic Protein

In order to quantitate the production of a morphogenic protein by a cell type, an immunoassay may be performed to detect the morphogen using a polyclonal or monoclonal antibody specific for that protein. For example, OP-1 may be detected using a polyclonal antibody specific for OP-1 in an ELISA, as follows.

1 µg/100 µl of affinity-purified polyclonal rabbit IgG specific for OP-1 is added to each well of a 96-well plate and incubated at 37° C. for an hour. The wells are washed four times with 0.167M sodium borate buffer with 0.15M NaCl (BSB), pH 8.2, containing 0.1% Tween 20. To minimize non-specific binding, the wells are blocked by filling completely with 1% bovine serum albumin (BSA) in BSB and incubating for 1 hour at 37° C. The wells are then washed four times with BSB containing 0.1% Tween 20. A 100 µl aliquot of an appropriate dilution of each of the test samples of cell culture supernatant is added to each well in triplicate and incubated at 37° C. for 30 min. After incubation, 100 µl biotinylated rabbit anti-OP-1 serum (stock solution is about 1 mg/ml and diluted 1:400 in BSB containing 1% BSA before use) is added to each well and incubated at 37° C. for 30 min. The wells are then washed four times with BSB containing 0.1% Tween 20. 100 µl strepavidin-alkaline (Southern Biotechnology Associates, Inc. Birmingham, Ala., diluted 1:2000 in BSB containing 0.1% Tween 20 before use) is added to each well and incubated at 37° C. for 30 min. The plates are washed four times with 0.5M Tris buffered Saline (TBS), pH 7.2. 50 µl substrate (ELISA Amplification System Kit, Life Technologies, Inc., Bethesda, Md.) is added to each well incubated at room temperature for 15 min. Then, 50 µl amplifier (from the same amplification system kit) is added and incubated for another 15 min at room temperature. The reaction is stopped by the addition of 50 µl 0.3M sulphuric acid. The OD at 490 nm of the solution in each well is recorded. To quantitate OP-1 in culture media, a OP-1 standard curve is performed in parallel with the test samples.

Polyclonal antibody may be prepared as follows. Each rabbit is given a primary immunization of 100 ug/500 µl E. coli produced OP-1 monomer (amino acids 328–431 in SEQ ID NO:5) in 0.1% SDS mixed with 500 µl Complete Freund's Adjuvant. The antigen is injected subcutaneously at multiple sites on the back and flanks of the animal. The rabbit is boosted after a month in the same manner using incomplete Freund's Adjuvant. Test bleeds are taken from the ear vein seven days later. Additional boosts and test bleeds are performed at monthly intervals until antibody against OP-1 is detected in the serum using an ELISA assay. Then, the rabbit is boosted with 100 µg of antigen and bled (15 ml per bleed) at days seven and ten after boosting.

Monoclonal antibody specific for a given morphogen may be prepared as follows. A mouse is given two injections of E. coli produced OP-1 monomer. The first injection contains 100 µg of OP-1 in complete Freund's adjuvant and is given subcutaneously. The second injection contains 50 µg of OP-1 in incomplete adjuvant and is given intraperitoneally. The mouse then receives a total of 230 µg of OP-1 (amino acids 307–431 in SEQ ID NO:5) in four intraperitoneal injections at various times over an eight month period. One week prior to fusion, the mouse is boosted intraperitoneally with 100 µg of OP-1 (307–431) and 30 µg of the N-terminal peptide ($Ser_{293}$-$Asn_{309}$-Cys) conjugated through the added cysteine to bovine serum albumin with SMCC crosslinking agent. This boost was repeated five days (IP), four days (IP), three days (IP) and one day (IV) prior to fusion. The mouse spleen cells are then fused to myeloma (e.g., 653) cells at a ratio of 1:1 using PEG 1500 (Boeringer Mannheim), and the cell fusion is plated and screened for OP-1-specific antibodies using OP-1 (307–431) as antigen. The cell fusion and monoclonal screening then are according to standard procedures well described in standard texts widely available in the art.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method for enhancing integration of a tooth in a mammalian tooth socket, comprising the step of administering a morphogen to a surface of said tooth socket or to an exterior root surface of said tooth, in an amount effective for inducing proliferation or differentiation of cementoblasts or periodontal fibroblasts, said morphogen comprising a dimeric protein that, when disposed in a mammalian tooth socket, induces periodontal tissue morphogenesis therein, said dimeric protein comprising a pair of folded polypeptides, the amino acid sequence of each of which comprises (i) a sequence sharing at least 70% homology with the C-terminal seven cysteine domain of human OP-1, residues 38–139 of Seq. ID No. 5; or (ii) a sequence defined by Generic Sequence 6, Seq. ID No. 31.

2. The method of claim 1 wherein said tooth socket comprises lost, damaged or nonviable periodontal tissue.

3. The method of claim 2 wherein said morphogen is administered to said surface prior to implantation of said tooth in said tooth socket.

4. The method of claim 3 comprising the additional preparative step of surgically removing scar tissue from an alveolar bone surface of said tooth socket prior to implantation of said tooth in said tooth socket.

5. The method of claim 3 comprising the additional preparative step of treating said surface with a demineralizing solution.

6. The method of claim 1 wherein said tooth is an implanted tooth.

7. The method of claim 1 wherein said tooth is a prosthetic tooth.

8. The method of claim 7 wherein said prosthetic tooth is an allogenic or autologous tooth.

9. A method for regenerating periodontal tissue in a mammalian tooth socket, or for inhibiting loss thereof, comprising the step of administering a morphogen to said tooth socket, in an amount effective for stimulating regeneration of periodontal ligament or cementum, or for preserving the differentiated phenotype of existing periodontal tissue, said morphogen comprising a dimeric protein that, when disposed in a mammalian tooth socket, induces periodontal tissue morphogenesis therein, said dimeric protein comprising a pair of folded polypeptides, the amino acid sequence of each of which comprises (i) a sequence sharing at least 70% homology with the C-terminal seven cysteine domain of human OP-1, residues 38–139 of Seq. ID No. 5; or (ii) a sequence defined by Generic Sequence 6, Seq. ID No. 31.

10. A method for inhibiting tissue damage associated with periodontal disease in a mammal, comprising the step of administering a morphogen to mammalian periodontal tissue at risk of said tissue damage, in an amount effective for inhibiting intimation or scarring, or for preserving the differentiated periodontal phenotype thereof, said morphogen comprising a dimeric protein that, when disposed in a mammalian tooth socket, induces periodontal tissue morphogenesis therein, said dimeric protein comprising a pair of folded polypeptides, the amino acid sequence of each of which comprises (i) a sequence sharing at least 70% homology with the C-terminal seven cysteine domain of human OP-1, residues 38–139 of Seq. ID No. 5; or (ii) a sequence defined by Generic Sequence 6, Seq. ID No. 31.

11. The method of claim 10 wherein said morphogen is administered systemically to said mammal.

12. A method for preparing a tooth or a mammalian tooth socket for implantation of said tooth into said socket, said socket being significantly reduced in viable periodontal tissue, the method comprising the steps of:

(a) preparing said tooth socket to receive said tooth by exposing a surface of fresh alveolar bone therein; and (b) administering a morphogen to either the exterior root surface of said tooth or to the exposed surface of fresh alveolar bone in said prepared socket, said morphogen being administered to said surface in an amount effective for inducing proliferation or differentiation of cementoblasts or periodontal fibroblasts, said morphogen comprising a dimeric protein that, when disposed in a mammalian tooth socket, induces periodontal tissue morphogenesis therein, said dimeric protein comprising a pair of folded polypeptides, the amino acid sequence of each of which comprises (i) a sequence sharing at least 70% homology with the C-terminal seven cysteine domain of human OP-1, residues 38–139 of Seq. ID No. 5; or (ii) a sequence defined by Generic Sequence 6, Seq. ID No. 31.

13. A method for implanting a tooth in a mammalian tooth socket, said socket being significantly reduced in viable periodontal tissue, comprising the steps of:

(a) preparing said socket to receive a tooth by exposing a fresh surface of alveolar bone therein;

(b) administering a morphogen either to the exterior root surface of said tooth or to the exposed fresh surface of alveolar bone in said tooth socket, in an amount effective for inducing proliferation or differentiation of cementoblasts or periodontal fibroblasts, said morphogen comprising a dimeric protein that, when disposed in a mammalian tooth socket, induces periodontal tissue morphogenesis therein, said dimeric protein comprising a pair of folded polypeptides, the amino acid sequence of each of which comprises (i) a sequence sharing at least 70% homology with the C-terminal seven cysteine domain of human OP-1, residues 38–139 of Seq. ID No. 5; or (ii) a sequence defined by Generic Sequence 6, Seq. ID No. 31; and (c) implanting said tooth in said prepared socket.

14. The method of claim 12 or 13 wherein said tooth root surface is partially demineralized before contact with said morphogen.

15. The method of claim 1, 9, 10, 12, or 13 wherein said morphogen is administered topically or by local injection.

16. The method of claim 15 wherein said morphogen is administered topically in a biocompatible acellular matrix.

17. The method of claim 16 wherein said matrix is derived from periodontal ligament, bone or cementum tissue.

18. The method of claim 16 wherein the amount of said morphogen administered is less than about 50 µg.

19. The method of claim 18 wherein the amount of said morphogen administered is less than about 25 µg.

20. The method of claim 15 wherein morphogen is administered topically in a viscous solution that maintains said morphogen at the locus of administration.

21. The method of claim 1, 9, 10, 12, or 13 wherein the amino acid sequence of each of said polypeptides comprises an approximately 102 amino acid sequence having cysteine residues at relative positions 1, 30, 34, 66, 67, 99 and 101 therein, wherein at least 70% of amino acid residues within said sequence are selected independently from residues occupying the corresponding positions within the sequence spanning residues 38–139 of Seq. ID No. 5, and conservative substitutions of said residues.

22. The method of claim 21 wherein said approximately 102 amino acid sequence has at least 101 amino acids.

23. The method of claim 21 wherein said approximately 102 amino acid sequence has at most 106 amino acids.

24. The method of claim 1, 9, 10, 12 or 13 wherein the amino acid sequence of each of said polypeptides comprises a sequence having greater than 60% amino acid identity with said C-terminal seven cysteine domain of human OP-1.

25. The method of claim 1, 9, 10, 12 or 13 wherein the amino acid sequence of at least one of said morphogen polypeptides comprises a sequence defined by OPX, Seq. ID No. 29.

26. The method of claim 1, 9, 10, 12 or 13 wherein the amino acid sequence of at least one of said morphogen polypeptides is identical to said C-terminal seven cysteine domain of human OP-1, or a conservative substitution variant thereof, provided that any said variant, when disposed in a mammalian tooth socket, induces periodontal tissue morphogenesis therein.

27. The method of claim 1, 9, 10, 12 or 13 wherein said morphogen is solubilized by association with a morphogen prodomain polypeptide.

28. The method of claim 1, 9, 10, 12 or 13 wherein said morphogen is obtained from culture medium of morphogen-secreting mammalian cells.

29. The method of claim 28 wherein the amino acid sequence of at least one of said morphogen polypeptides comprises the pro form of human OP-1, residues 30–43 of Seq. ID No. 17, or a conservative substitution variant thereof, provided that any said variant, when disposed in a mammalian tooth socket, induces periodontal tissue morphogenesis therein.

30. A composition comprising:
   (a) a morphogen comprising a dimeric protein that, when disposed in a mammalian tooth socket, induces morphogenesis of periodontal tissue, said dimeric protein comprising a pair of folded polypeptides, the amino acid sequence of each of which comprises
      (i) a sequence sharing at least 70% homology with the C-terminal seven cysteine domain of human OP-1, residues 38–139 of Seq. ID No. 5; or
      (ii) a sequence defined by Generic Sequence 6, Seq. ID No. 31, and
   (b) a cofactor that mitigates symptoms associated with periodontal tissue damage, the concentration of said morphogen in said composition being effective for inducing proliferation or differentiation of mammalian periodontal fibroblasts or cementoblasts.

31. The composition of claim 30 wherein the concentration of said morphogen is effective for inducing regeneration of periodontal ligament or cementum.

32. The composition of claim 30 wherein the concentration of said morphogen is effective for enhancing integration of an implanted tooth in a mammalian tooth socket.

33. The composition of claim 30 wherein said cofactor is selected from an antibiotic, antiseptic, anesthetic, analgesic or a non-steroidal anti-inflammatory agent.

34. The composition of claim 30 wherein said morphogen and said cofactor are dispersed in a biocompatible acellular matrix.

35. The composition of claim wherein said matrix is derived from mammalian periodontal ligament or from demineralized mammalian bone or cementum.

36. The composition of claim 30 comprising a viscous solution effective for maintaining a topically administered morphogen at a periodontal tissue locus.

37. The composition of claim 30 wherein the amino acid sequence of each of said polypeptides comprises an approximately 102 amino acid sequence having cysteine residues at relative positions 1, 30, 34, 66, 67, 99 and 101 therein, wherein at least 70% of amino acid residues within said sequence are selected independently from residues occupying the corresponding positions within the sequence spanning residues 38–139 of Seq. ID No. 5, and conservative substitutions of said residues.

38. The composition of claim 37 wherein said approximately 102 amino acid sequence has at least 101 amino acids.

39. The composition of claim 37 wherein said approximately 102 amino acid sequence has at most 106 amino acids.

40. The composition of claim 30 wherein the amino acid sequences of said morphogen polypeptides comprise a sequence sharing at least 80% homology with said C-terminal seven cysteine domain of human OP-1.

41. The composition of claim 30 wherein the amino acid sequences of said polypeptides comprise a sequence having greater than 60% amino acid identity with said C-terminal seven cysteine domain of human OP-1.

42. The composition of claim 41 whereto the amino acid sequences of said polypeptides comprise a sequence having greater than 65% amino acid identity with said C-terminal seven cysteine domain of human OP-1.

43. The composition of claim 30 wherein the amino acid sequences of said polypeptides comprise a sequence defined by OPX, Seq. ID No. 29.

44. The composition of claim 30 wherein the amino acid sequence of at least one of said morphogen polypeptides is identical to said C-terminal seven cysteine domain of human OP-1, or a conservative substitution variant thereof, provided that any said variant, when disposed in a mammalian tooth socket, induces periodontal tissue morphogenesis therein.

45. The composition of claim 30 wherein said morphogen is solubilized by association with a morphogen prodomain polypeptide.

46. The composition of claim 30 wherein said morphogen is obtained from culture medium of morphogen-secreting mammalian cells.

47. The composition of claim 30 wherein the amino acid sequence of at least one of said morphogen polypeptides comprises the pro form of human OP-1, residues 30–431 of Seq. ID No. 17, or a conservative substitution variant thereof, provided that any said variant, when disposed in a mammalian tooth socket, induces periodontal tissue morphogenesis therein.

48. A prosthetic tooth for implantation in a mammalian tooth socket, the exterior root surface of said tooth having a morphogen adsorbed thereon, said morphogen comprising a dimeric protein comprising a pair of folded polypeptides, the amino acid sequence of each of which comprises
   (i) a sequence sharing at least 70% homology with the C-terminal seven cysteine domain of human OP-1, residues 38–139 of Seq. ID No. 5; or
   (ii) a sequence defined by Generic Sequence 6, Seq. ID No. 31, further wherein, when disposed in a mammalian tooth socket, said dimeric protein induces morphogenesis of periodontal tissue.

49. The prosthetic tooth of claim 48, prepared by absorption of said morphogen onto an exterior root surface of a naturally-derived allogenic or autologous tooth.

50. The prosthetic tooth of claim 49, prepared by exposing the exterior root surface of said tooth to demineralizing conditions, prior to absorbing said morphogen thereon.

51. The prosthetic tooth of claim 48, prepared by replacing the root of a naturally-derived allogenic or autologous tooth with a biologically inert synthetic root.

52. The prosthetic tooth of claim 51 wherein said biologically inert synthetic root comprises collagen, ceramic or metal.

53. The prosthetic tooth of claim 48, prepared by adsorption of said morphogen onto the exterior root surface of a synthetic tooth.

54. The prosthetic tooth of claim 53 wherein said synthetic tooth comprises collagen, ceramic or metal.

* * * * *

UNITED STATES PATENT AND TRADEMARK OFFICE
CERTIFICATE OF CORRECTION

PATENT NO.   : 5,733,878
DATED        : March 31, 1998
INVENTOR(S)  : Thangavel Kuberasampath et al.

It is certified that error appears in the above-identified patent and that said Letters Patent is hereby corrected as shown below:

<u>Title page,</u>
After Item [73], Assignee, please add:
-- [*] Notice: This patent is subject to a terminal disclaimer. --

Signed and Sealed this

First Day of July, 2003

JAMES E. ROGAN
*Director of the United States Patent and Trademark Office*

SEQUENCE LISTING ( 1 ) GENERAL INFORMATION:

( i i i ) NUMBER OF SEQUENCES: 33

( 2 ) INFORMATION FOR SEQ ID NO:1:

( i ) SEQUENCE CHARACTERISTICS:
    ( A ) LENGTH: 97 amino acids
    ( B ) TYPE: amino acid
    ( C ) STRANDEDNESS: single
    ( D ) TOPOLOGY: linear ( i i ) MOLECULE TYPE: protein ( i x ) FEATURE:
    ( A ) NAME/KEY: Protein
    ( B ) LOCATION: 1..97
    ( D ) OTHER INFORMATION: /label=GENERIC-SEQ-1
      / note= "EACH XAA INDICATES ONE OF THE 20 NATURALLY
      OCCURRING L- ISOMER, ALPHA-AMINO ACIDS, OR A
      DERIVATIVE THEREOF"

( x i ) SEQUENCE DESCRIPTION: SEQ ID NO:1:

| Xaa | Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|---|
| 1 | | | | 5 | | | | | 10 | | | | | 15 | |
| Xaa | Xaa | Xaa | Xaa | Xaa | Xaa | Xaa | Xaa | Cys | Xaa | Xaa | Xaa | Cys | Xaa | Xaa | Xaa |
| | | | 20 | | | | | 25 | | | | | | 30 | |
| Xaa | Xaa | Xaa | Xaa | Xaa | Xaa | Xaa | Xaa | Xaa | Xaa | Xaa | Xaa | Xaa | Xaa | Xaa | Xaa |
| | | 35 | | | | | | 40 | | | | | | 45 | |
| Xaa | Xaa | Xaa | Xaa | Xaa | Xaa | Xaa | Xaa | Xaa | Xaa | Xaa | Xaa | Cys | Cys | Xaa | Xaa |
| | 50 | | | | | | 55 | | | | | 60 | | | |
| Xaa | Xaa | Xaa | Xaa | Xaa | Xaa | Xaa | Xaa | Xaa | Xaa | Xaa | Xaa | Xaa | Xaa | Xaa | Xaa |
| 65 | | | | | | 70 | | | | | 75 | | | | 80 |
| Xaa | Xaa | Xaa | Xaa | Xaa | Xaa | Xaa | Xaa | Xaa | Xaa | Xaa | Xaa | Xaa | Cys | Xaa | Cys |
| | | | | 85 | | | | | 90 | | | | | 95 | |
| Xaa | | | | | | | | | | | | | | | |

( 2 ) INFORMATION FOR SEQ ID NO:2:

( i ) SEQUENCE CHARACTERISTICS:
    ( A ) LENGTH: 97 amino acids
    ( B ) TYPE: amino acid
    ( C ) STRANDEDNESS: single
    ( D ) TOPOLOGY: linear ( i i ) MOLECULE TYPE: protein ( i x ) FEATURE:
    ( A ) NAME/KEY: Protein
    ( B ) LOCATION: 1..97
    ( D ) OTHER INFORMATION: /label=GENERIC-SEQ-2
      / note= "EACH XAA INDICATES ONE OF THE 20 NATURALLY
      OCCURING L-ISOMER, ALPHA-AMINO ACIDS, OR A
      DERIVATIVE THEREOF"

( x i ) SEQUENCE DESCRIPTION: SEQ ID NO:2:

| Xaa | Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|---|
| 1 | | | | 5 | | | | | 10 | | | | | 15 | |
| Xaa | Xaa | Xaa | Xaa | Xaa | Xaa | Xaa | Xaa | Cys | Xaa | Xaa | Xaa | Cys | Xaa | Xaa | Xaa |
| | | | 20 | | | | | 25 | | | | | | 30 | |
| Xaa | Xaa | Xaa | Cys | Xaa | Xaa | Xaa | Xaa | Xaa | Xaa | Xaa | Xaa | Xaa | Xaa | Xaa | Xaa |
| | | 35 | | | | | | 40 | | | | | | 45 | |
| Xaa | Xaa | Xaa | Xaa | Xaa | Xaa | Xaa | Xaa | Xaa | Xaa | Xaa | Xaa | Cys | Cys | Xaa | Xaa |
| | 50 | | | | | | 55 | | | | | 60 | | | |

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Cys Xaa Cys
            85                  90                  95

Xaa ( 2 ) INFORMATION FOR SEQ ID NO:3:

( i ) SEQUENCE CHARACTERISTICS:
        ( A ) LENGTH: 97 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..97
        ( D ) OTHER INFORMATION: /label=GENERIC-SEQ-3
            / note= "WHEREIN EACH XAA IS INDEPENDENTLY SELECTED FROM
            A GROUP OF ONE OR MORE SPECIFIED AMINO ACIDS AS DEFINED
            IN THE SPECIFICATION "

( x i ) SEQUENCE DESCRIPTION: SEQ ID NO:3:

Leu Tyr Val Xaa Phe Xaa Xaa Xaa Gly Trp Xaa Xaa Trp Xaa Xaa Ala
1               5                   10                  15

Pro Xaa Gly Xaa Xaa Ala Xaa Tyr Cys Xaa Gly Xaa Cys Xaa Xaa Pro
            20                  25                  30

Xaa Xaa Xaa Xaa Xaa Xaa Xaa Xaa Asn His Ala Xaa Xaa Xaa Xaa Leu
            35                  40                  45

Xaa Xaa Xaa Xaa Xaa Xaa Xaa Xaa Xaa Xaa Xaa Cys Cys Xaa Pro
        50                  55                  60

Xaa Xaa Xaa Xaa Xaa Xaa Xaa Xaa Leu Xaa Xaa Xaa Xaa Xaa Xaa Xaa
65                  70                  75                  80

Val Xaa Leu Xaa Xaa Xaa Xaa Xaa Met Xaa Val Xaa Xaa Cys Gly Cys
            85                  90                  95

Xaa ( 2 ) INFORMATION FOR SEQ ID NO:4:

( i ) SEQUENCE CHARACTERISTICS:
        ( A ) LENGTH: 102 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..102
        ( D ) OTHER INFORMATION: /label=GENERIC-SEQ-4
            / note= "WHEREIN EACH XAA IS INDEPENDENTLY SELECTED FROM
            A GROUP OF ONE OR MORE SPECIFIED AMINO ACIDS AS DEFINED
            IN THE SPECIFICATION"

( x i ) SEQUENCE DESCRIPTION: SEQ ID NO:4:

Cys Xaa Xaa Xaa Xaa Leu Tyr Val Xaa Phe Xaa Xaa Xaa Gly Trp Xaa
1               5                   10                  15

Xaa Trp Xaa Xaa Ala Pro Xaa Gly Xaa Xaa Ala Xaa Tyr Cys Xaa Gly
            20                  25                  30

Xaa Cys Xaa Xaa Pro Xaa Xaa Xaa Xaa Xaa Xaa Xaa Xaa Asn His Ala
        35                  40                  45

```
           Xaa  Xaa  Xaa  Xaa  Leu  Xaa  Xaa  Xaa  Xaa  Xaa  Xaa  Xaa  Xaa  Xaa  Xaa
                     50                  55                       60

Xaa  Cys  Cys  Xaa  Pro  Xaa  Xaa  Xaa  Xaa  Xaa  Xaa  Xaa  Xaa  Leu  Xaa  Xaa
           65                       70                       75                       80

Xaa  Xaa  Xaa  Xaa  Xaa  Val  Xaa  Leu  Xaa  Xaa  Xaa  Xaa  Xaa  Met  Xaa  Val
                               85                       90                       95

Xaa  Xaa  Cys  Gly  Cys  Xaa
                          100
```

( 2 ) INFORMATION FOR SEQ ID NO:5:

( i ) SEQUENCE CHARACTERISTICS:
        ( A ) LENGTH: 139 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..139
        ( D ) OTHER INFORMATION: /note= "HOP-1 (MATURE FORM)"

( x i ) SEQUENCE DESCRIPTION: SEQ ID NO:5:

```
           Ser  Thr  Gly  Ser  Lys  Gln  Arg  Ser  Gln  Asn  Arg  Ser  Lys  Thr  Pro  Lys
           1                   5                        10                      15

Asn  Gln  Glu  Ala  Leu  Arg  Met  Ala  Asn  Val  Ala  Glu  Asn  Ser  Ser  Ser
                          20                       25                       30

Asp  Gln  Arg  Gln  Ala  Cys  Lys  Lys  His  Glu  Leu  Tyr  Val  Ser  Phe  Arg
                          35                       40                       45

Asp  Leu  Gly  Trp  Gln  Asp  Trp  Ile  Ile  Ala  Pro  Glu  Gly  Tyr  Ala  Ala
                     50                       55                       60

Tyr  Tyr  Cys  Glu  Gly  Glu  Cys  Ala  Phe  Pro  Leu  Asn  Ser  Tyr  Met  Asn
           65                       70                       75                       80

Ala  Thr  Asn  His  Ala  Ile  Val  Gln  Thr  Leu  Val  His  Phe  Ile  Asn  Pro
                               85                       90                       95

Glu  Thr  Val  Pro  Lys  Pro  Cys  Cys  Ala  Pro  Thr  Gln  Leu  Asn  Ala  Ile
                          100                      105                      110

Ser  Val  Leu  Tyr  Phe  Asp  Asp  Ser  Ser  Asn  Val  Ile  Leu  Lys  Lys  Tyr
                     115                      120                      125

Arg  Asn  Met  Val  Val  Arg  Ala  Cys  Gly  Cys  His
                     130                      135
```

( 2 ) INFORMATION FOR SEQ ID NO:6:

( i ) SEQUENCE CHARACTERISTICS:
        ( A ) LENGTH: 139 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..139
        ( D ) OTHER INFORMATION: /note= "MOP-1 (MATURE FORM)"

( x i ) SEQUENCE DESCRIPTION: SEQ ID NO:6:

```
           Ser  Thr  Gly  Gly  Lys  Gln  Arg  Ser  Gln  Asn  Arg  Ser  Lys  Thr  Pro  Lys
           1                   5                        10                      15

Asn  Gln  Glu  Ala  Leu  Arg  Met  Ala  Ser  Val  Ala  Glu  Asn  Ser  Ser  Ser
                          20                       25                       30
```

```
Asp Gln Arg Gln Ala Cys Lys Lys His Glu Leu Tyr Val Ser Phe Arg
         35                  40                  45
Asp Leu Gly Trp Gln Asp Trp Ile Ile Ala Pro Glu Gly Tyr Ala Ala
     50                  55                  60
Tyr Tyr Cys Glu Gly Glu Cys Ala Phe Pro Leu Asn Ser Tyr Met Asn
 65              70                  75                      80
Ala Thr Asn His Ala Ile Val Gln Thr Leu Val His Phe Ile Asn Pro
                 85                  90                  95
Asp Thr Val Pro Lys Pro Cys Cys Ala Pro Thr Gln Leu Asn Ala Ile
             100                 105                 110
Ser Val Leu Tyr Phe Asp Asp Ser Ser Asn Val Ile Leu Lys Lys Tyr
             115                 120                 125
Arg Asn Met Val Val Arg Ala Cys Gly Cys His
             130             135
```

(2) INFORMATION FOR SEQ ID NO:7:

(i) SEQUENCE CHARACTERISTICS:
        (A) LENGTH: 139 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..139
        (D) OTHER INFORMATION: /note= "HOP-2 (MATURE FORM)"

(xi) SEQUENCE DESCRIPTION: SEQ ID NO:7:

```
Ala Val Arg Pro Leu Arg Arg Arg Gln Pro Lys Lys Ser Asn Glu Leu
 1               5                  10                  15
Pro Gln Ala Asn Arg Leu Pro Gly Ile Phe Asp Asp Val His Gly Ser
             20                  25                  30
His Gly Arg Gln Val Cys Arg Arg His Glu Leu Tyr Val Ser Phe Gln
         35                  40                  45
Asp Leu Gly Trp Leu Asp Trp Val Ile Ala Pro Gln Gly Tyr Ser Ala
     50                  55                  60
Tyr Tyr Cys Glu Gly Glu Cys Ser Phe Pro Leu Asp Ser Cys Met Asn
 65              70                  75                      80
Ala Thr Asn His Ala Ile Leu Gln Ser Leu Val His Leu Met Lys Pro
                 85                  90                  95
Asn Ala Val Pro Lys Ala Cys Cys Ala Pro Thr Lys Leu Ser Ala Thr
             100                 105                 110
Ser Val Leu Tyr Tyr Asp Ser Ser Asn Asn Val Ile Leu Arg Lys His
             115                 120                 125
Arg Asn Met Val Val Lys Ala Cys Gly Cys His
             130             135
```

(2) INFORMATION FOR SEQ ID NO:8:

(i) SEQUENCE CHARACTERISTICS:
        (A) LENGTH: 139 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein (B) LOCATION: 1..139
(D) OTHER INFORMATION: /note= "MOP-2 (MATURE FORM)"

(xi) SEQUENCE DESCRIPTION: SEQ ID NO:8:

| Ala | Ala | Arg | Pro | Leu | Lys | Arg | Arg | Gln | Pro | Lys | Lys | Thr | Asn | Glu | Leu |
|---|---|---|---|---|---|---|---|---|---|---|---|---|---|---|---|
| 1 | | | | 5 | | | | | 10 | | | | | 15 | |

| Pro | His | Pro | Asn | Lys | Leu | Pro | Gly | Ile | Phe | Asp | Asp | Gly | His | Gly | Ser |
|---|---|---|---|---|---|---|---|---|---|---|---|---|---|---|---|
| | | | 20 | | | | | 25 | | | | | 30 | | |

| Arg | Gly | Arg | Glu | Val | Cys | Arg | Arg | His | Glu | Leu | Tyr | Val | Ser | Phe | Arg |
|---|---|---|---|---|---|---|---|---|---|---|---|---|---|---|---|
| | | 35 | | | | | 40 | | | | | 45 | | | |

| Asp | Leu | Gly | Trp | Leu | Asp | Trp | Val | Ile | Ala | Pro | Gln | Gly | Tyr | Ser | Ala |
|---|---|---|---|---|---|---|---|---|---|---|---|---|---|---|---|
| | 50 | | | | | 55 | | | | | 60 | | | | |

| Tyr | Tyr | Cys | Glu | Gly | Glu | Cys | Ala | Phe | Pro | Leu | Asp | Ser | Cys | Met | Asn |
|---|---|---|---|---|---|---|---|---|---|---|---|---|---|---|---|
| 65 | | | | | 70 | | | | | 75 | | | | | 80 |

| Ala | Thr | Asn | His | Ala | Ile | Leu | Gln | Ser | Leu | Val | His | Leu | Met | Lys | Pro |
|---|---|---|---|---|---|---|---|---|---|---|---|---|---|---|---|
| | | | | 85 | | | | | 90 | | | | | 95 | |

| Asp | Val | Val | Pro | Lys | Ala | Cys | Cys | Ala | Pro | Thr | Lys | Leu | Ser | Ala | Thr |
|---|---|---|---|---|---|---|---|---|---|---|---|---|---|---|---|
| | | | 100 | | | | | 105 | | | | | 110 | | |

| Ser | Val | Leu | Tyr | Tyr | Asp | Ser | Ser | Asn | Asn | Val | Ile | Leu | Arg | Lys | His |
|---|---|---|---|---|---|---|---|---|---|---|---|---|---|---|---|
| | | 115 | | | | | 120 | | | | | 125 | | | |

| Arg | Asn | Met | Val | Val | Lys | Ala | Cys | Gly | Cys | His |
|---|---|---|---|---|---|---|---|---|---|---|
| 130 | | | | | 135 | | | | | |

(2) INFORMATION FOR SEQ ID NO:9:

(i) SEQUENCE CHARACTERISTICS:
  (A) LENGTH: 101 amino acids
  (B) TYPE: amino acid
  (C) STRANDEDNESS: single
  (D) TOPOLOGY: linear (ii) MOLECULE TYPE: protein (ix) FEATURE:
  (A) NAME/KEY: Protein
  (B) LOCATION: 1..101
  (D) OTHER INFORMATION: /note= "CBMP-2A(FX)"

(xi) SEQUENCE DESCRIPTION: SEQ ID NO:9:

| Cys | Lys | Arg | His | Pro | Leu | Tyr | Val | Asp | Phe | Ser | Asp | Val | Gly | Trp | Asn |
|---|---|---|---|---|---|---|---|---|---|---|---|---|---|---|---|
| 1 | | | | 5 | | | | | 10 | | | | | 15 | |

| Asp | Trp | Ile | Val | Ala | Pro | Pro | Gly | Tyr | His | Ala | Phe | Tyr | Cys | His | Gly |
|---|---|---|---|---|---|---|---|---|---|---|---|---|---|---|---|
| | | | 20 | | | | | 25 | | | | | 30 | | |

| Glu | Cys | Pro | Phe | Pro | Leu | Ala | Asp | His | Leu | Asn | Ser | Thr | Asn | His | Ala |
|---|---|---|---|---|---|---|---|---|---|---|---|---|---|---|---|
| | | 35 | | | | | 40 | | | | | 45 | | | |

| Ile | Val | Gln | Thr | Leu | Val | Asn | Ser | Val | Asn | Ser | Lys | Ile | Pro | Lys | Ala |
|---|---|---|---|---|---|---|---|---|---|---|---|---|---|---|---|
| | 50 | | | | | 55 | | | | | 60 | | | | |

| Cys | Cys | Val | Pro | Thr | Glu | Leu | Ser | Ala | Ile | Ser | Met | Leu | Tyr | Leu | Asp |
|---|---|---|---|---|---|---|---|---|---|---|---|---|---|---|---|
| 65 | | | | | 70 | | | | | 75 | | | | | 80 |

| Glu | Asn | Glu | Lys | Val | Val | Leu | Lys | Asn | Tyr | Gln | Asp | Met | Val | Val | Glu |
|---|---|---|---|---|---|---|---|---|---|---|---|---|---|---|---|
| | | | | 85 | | | | | 90 | | | | | 95 | |

| Gly | Cys | Gly | Cys | Arg |
|---|---|---|---|---|
| | | | | 100 |

(2) INFORMATION FOR SEQ ID NO:10:

(i) SEQUENCE CHARACTERISTICS:
  (A) LENGTH: 101 amino acids
  (B) TYPE: amino acid
  (C) STRANDEDNESS: single
  (D) TOPOLOGY: linear (ii) MOLECULE TYPE: protein (ix) FEATURE:
(A) NAME/KEY: Protein
(B) LOCATION: 1..101
(D) OTHER INFORMATION: /note= "CBMP-2B(FX)"

(xi) SEQUENCE DESCRIPTION: SEQ ID NO:10:

| Cys | Arg | Arg | His | Ser | Leu | T ( i x ) FEATURE:
    ( A ) NAME/KEY: Protein
    ( B ) LOCATION: 1..102
    ( D ) OTHER INFORMATION: /note= "VGL(FX)"

( x i ) SEQUENCE DESCRIPTION: SEQ ID NO:12:

```
Cys Lys Lys Arg His Leu Tyr Val Glu Phe Lys Asp Val Gly Trp Gln
 1               5                  10                 15

Asn Trp Val Ile Ala Pro Gln Gly Tyr Met Ala Asn Tyr Cys Tyr Gly
                20                  25                 30

Glu Cys Pro Tyr Pro Leu Thr Glu Ile Leu Asn Gly Ser Asn His Ala
            35                  40              45

Ile Leu Gln Thr Leu Val His Ser Ile Glu Pro Glu Asp Ile Pro Leu
        50                  55              60

Pro Cys Cys Val Pro Thr Lys Met Ser Pro Ile Ser Met Leu Phe Tyr
65                  70                  75                  80

Asp Asn Asn Asp Asn Val Val Leu Arg His Tyr Glu Asn Met Ala Val
                85                  90                  95

Asp Glu Cys Gly Cys Arg
            100
```

( 2 ) INFORMATION FOR SEQ ID NO:13:

( i ) SEQUENCE CHARACTERISTICS:
        ( A ) LENGTH: 102 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..102
        ( D ) OTHER INFORMATION: /note= "VGR-1(FX)"

( x i ) SEQUENCE DESCRIPTION: SEQ ID NO:13:

```
Cys Lys Lys His Glu Leu Tyr Val Ser Phe Gln Asp Val Gly Trp Gln
 1               5                  10                 15

Asp Trp Ile Ile Ala Pro Lys Gly Tyr Ala Ala Asn Tyr Cys Asp Gly
                20                  25                 30

Glu Cys Ser Phe Pro Leu Asn Ala His Met Asn Ala Thr Asn His Ala
            35                  40              45

Ile Val Gln Thr Leu Val His Val Met Asn Pro Glu Tyr Val Pro Lys
        50                  55              60

Pro Cys Cys Ala Pro Thr Lys Val Asn Ala Ile Ser Val Leu Tyr Phe
65                  70                  75                  80

Asp Asp Asn Ser Asn Val Ile Leu Lys Lys Tyr Arg Asn Met Val Val
                85                  90                  95

Arg Ala Cys Gly Cys His
            100
```

( 2 ) INFORMATION FOR SEQ ID NO:14:

( i ) SEQUENCE CHARACTERISTICS:
        ( A ) LENGTH: 106 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein (B) LOCATION: 1..106
(D) OTHER INFORMATION: /note= "GDF-1 (FX)"

(x i) SEQUENCE DESCRIPTION: SEQ ID NO:14:

| Cys | Arg | Ala | Arg | Arg | Leu | Tyr | Val | Ser | Phe | Arg | Glu | Val | Gly | Trp | His |
|---|---|---|---|---|---|---|---|---|---|---|---|---|---|---|---|
| 1 | | | | 5 | | | | | 10 | | | | | 15 | |

| Arg | Trp | Val | Ile | Ala | Pro | Arg | Gly | Phe | Leu | Ala | Asn | Tyr | Cys | Gln | Gly |
|---|---|---|---|---|---|---|---|---|---|---|---|---|---|---|---|
| | | | 20 | | | | | 25 | | | | | 30 | | |

| Gln | Cys | Ala | Leu | Pro | Val | Ala | Leu | Ser | Gly | Ser | Gly | Gly | Pro | Pro | Ala |
|---|---|---|---|---|---|---|---|---|---|---|---|---|---|---|---|
| | | 35 | | | | | 40 | | | | | 45 | | | |

| Leu | Asn | His | Ala | Val | Leu | Arg | Ala | Leu | Met | His | Ala | Ala | Ala | Pro | Gly |
|---|---|---|---|---|---|---|---|---|---|---|---|---|---|---|---|
| | 50 | | | | | 55 | | | | | 60 | | | | |

| Ala | Ala | Asp | Leu | Pro | Cys | Cys | Val | Pro | Ala | Arg | Leu | Ser | Pro | Ile | Ser |
|---|---|---|---|---|---|---|---|---|---|---|---|---|---|---|---|
| 65 | | | | | 70 | | | | | 75 | | | | | 80 |

| Val | Leu | Phe | Phe | Asp | Asn | Ser | Asp | Asn | Val | Val | Leu | Arg | Gln | Tyr | Glu |
|---|---|---|---|---|---|---|---|---|---|---|---|---|---|---|---|
| | | | | 85 | | | | | 90 | | | | | 95 | |

| Asp | Met | Val | Val | Asp | Glu | Cys | Gly | Cys | Arg |
|---|---|---|---|---|---|---|---|---|---|
| | | | 100 | | | | | 105 | |

(2) INFORMATION FOR SEQ ID NO:15:

(i) SEQUENCE CHARACTERISTICS:
(A) LENGTH: 5 amino acids
(B) TYPE: amino acid
(C) STRANDEDNESS: single
(D) TOPOLOGY: linear (ii) MOLECULE TYPE: peptide (x i) SEQUENCE DESCRIPTION: SEQ ID NO:15:

| Cys | Xaa | Xaa | Xaa | Xaa |
|---|---|---|---|---|
| 1 | | | | 5 |

(2) INFORMATION FOR SEQ ID NO:16:

(i) SEQUENCE CHARACTERISTICS:
(A) LENGTH: 1822 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 49..1341
(D) OTHER INFORMATION: /product="HOP-1"

(x i) SEQUENCE DESCRIPTION: SEQ ID NO:16:

```
GGTGCGGGCC CGGAGCCCGG AGCCCGGGTA GCGCGTAGAG CCGGCGCG ATG CAC GTG      57
                                                       Met His Val
                                                        1

CGC TCA CTG CGA GCT GCG GCG CCG CAC AGC TTC GTG GCG CTC TGG GCA     105
Arg Ser Leu Arg Ala Ala Ala Pro His Ser Phe Val Ala Leu Trp Ala
     5              10                  15

CCC CTG TTC CTG CTG CGC TCC GCC CTG GCC GAC TTC AGC CTG GAC AAC     153
Pro Leu Phe Leu Leu Arg Ser Ala Leu Ala Asp Phe Ser Leu Asp Asn
 20              25                  30                  35

GAG GTG CAC TCG AGC TTC ATC CAC CGG CGC CTC CGC AGC CAG GAG CGG     201
Glu Val His Ser Ser Phe Ile His Arg Arg Leu Arg Ser Gln Glu Arg
                 40                  45                  50

CGG GAG ATG CAG CGC GAG ATC CTC TCC ATT TTG GGC TTG CCC CAC CGC     249
Arg Glu Met Gln Arg Glu Ile Leu Ser Ile Leu Gly Leu Pro His Arg
             55                  60                  65
```

```
CCG CGC CCG CAC CTC CAG GGC AAG CAC AAC TCG GCA CCC ATG TTC ATG                     297
Pro Arg Pro His Leu Gln Gly Lys His Asn Ser Ala Pro Met Phe Met
        70                      75                  80

CTG GAC CTG TAC AAC GCC ATG GCG GTG GAG GAG GGC GGC GGG CCC GGC                     345
Leu Asp Leu Tyr Asn Ala Met Ala Val Glu Glu Gly Gly Gly Pro Gly
        85                      90                  95

GGC CAG GGC TTC TCC TAC CCC TAC AAG GCC GTC TTC AGT ACC CAG GGC                     393
Gly Gln Gly Phe Ser Tyr Pro Tyr Lys Ala Val Phe Ser Thr Gln Gly
100             105                     110                     115

CCC CCT CTG GCC AGC CTG CAA GAT AGC CAT TTC CTC ACC GAC GCC GAC                     441
Pro Pro Leu Ala Ser Leu Gln Asp Ser His Phe Leu Thr Asp Ala Asp
                120                     125                 130

ATG GTC ATG AGC TTC GTC AAC CTC GTG GAA CAT GAC AAG GAA TTC TTC                     489
Met Val Met Ser Phe Val Asn Leu Val Glu His Asp Lys Glu Phe Phe
                135                     140                 145

CAC CCA CGC TAC CAC CAT CGA GAG TTC CGG TTT GAT CTT TCC AAG ATC                     537
His Pro Arg Tyr His His Arg Glu Phe Arg Phe Asp Leu Ser Lys Ile
            150                     155                 160

CCA GAA GGG GAA GCT GTC ACG GCA GCC GAA TTC CGG ATC TAC AAG GAC                     585
Pro Glu Gly Glu Ala Val Thr Ala Ala Glu Phe Arg Ile Tyr Lys Asp
        165                     170                     175

TAC ATC CGG GAA CGC TTC GAC AAT GAG ACG TTC CGG ATC AGC GTT TAT                     633
Tyr Ile Arg Glu Arg Phe Asp Asn Glu Thr Phe Arg Ile Ser Val Tyr
180                 185                     190                 195

CAG GTG CTC CAG GAG CAC TTG GGC AGG GAA TCG GAT CTC TTC CTG CTC                     681
Gln Val Leu Gln Glu His Leu Gly Arg Glu Ser Asp Leu Phe Leu Leu
                200                     205                 210

GAC AGC CGT ACC CTC TGG GCC TCG GAG GAG GGC TGG CTG GTG TTT GAC                     729
Asp Ser Arg Thr Leu Trp Ala Ser Glu Glu Gly Trp Leu Val Phe Asp
            215                     220                 225

ATC ACA GCC ACC AGC AAC CAC TGG GTG GTC AAT CCG CGG CAC AAC CTG                     777
Ile Thr Ala Thr Ser Asn His Trp Val Val Asn Pro Arg His Asn Leu
        230                     235                     240

GGC CTG CAG CTC TCG GTG GAG ACG CTG GAT GGG CAG AGC ATC AAC CCC                     825
Gly Leu Gln Leu Ser Val Glu Thr Leu Asp Gly Gln Ser Ile Asn Pro
        245                     250                     255

AAG TTG GCG GGC CTG ATT GGG CGG CAC GGG CCC CAG AAC AAG CAG CCC                     873
Lys Leu Ala Gly Leu Ile Gly Arg His Gly Pro Gln Asn Lys Gln Pro
260                 265                     270                 275

TTC ATG GTG GCT TTC TTC AAG GCC ACG GAG GTC CAC TTC CGC AGC ATC                     921
Phe Met Val Ala Phe Phe Lys Ala Thr Glu Val His Phe Arg Ser Ile
                280                     285                 290

CGG TCC ACG GGG AGC AAA CAG CGC AGC CAG AAC CGC TCC AAG ACG CCC                     969
Arg Ser Thr Gly Ser Lys Gln Arg Ser Gln Asn Arg Ser Lys Thr Pro
            295                     300                 305

AAG AAC CAG GAA GCC CTG CGG ATG GCC AAC GTG GCA GAG AAC AGC AGC                     1017
Lys Asn Gln Glu Ala Leu Arg Met Ala Asn Val Ala Glu Asn Ser Ser
        310                     315                     320

AGC GAC CAG AGG CAG GCC TGT AAG AAG CAC GAG CTG TAT GTC AGC TTC                     1065
Ser Asp Gln Arg Gln Ala Cys Lys Lys His Glu Leu Tyr Val Ser Phe
        325                     330                     335

CGA GAC CTG GGC TGG CAG GAC TGG ATC ATC GCG CCT GAA GGC TAC GCC                     1113
Arg Asp Leu Gly Trp Gln Asp Trp Ile Ile Ala Pro Glu Gly Tyr Ala
340                 345                     350                 355

GCC TAC TAC TGT GAG GGG GAG TGT GCC TTC CCT CTG AAC TCC TAC ATG                     1161
Ala Tyr Tyr Cys Glu Gly Glu Cys Ala Phe Pro Leu Asn Ser Tyr Met
                360                     365                 370

AAC GCC ACC AAC CAC GCC ATC GTG CAG ACG CTG GTC CAC TTC ATC AAC                     1209
Asn Ala Thr Asn His Ala Ile Val Gln Thr Leu Val His Phe Ile Asn
            375                     380                 385
```

| | | | | | | | | | | | | | | |
|---|---|---|---|---|---|---|---|---|---|---|---|---|---|---|
| CCG | GAA | ACG | GTG | CCC | AAG | CCC | TGC | TGT | GCG | CCC | ACG | CAG | CTC | AAT | GCC | 1257 |
| Pro | Glu | Thr | Val | Pro | Lys | Pro | Cys | Cys | Ala | Pro | Thr | Gln | Leu | Asn | Ala | |
| | | 390 | | | | | 395 | | | | 400 | | | | | |
| ATC | TCC | GTC | CTC | TAC | TTC | GAT | GAC | AGC | TCC | AAC | GTC | ATC | CTG | AAG | AAA | 1305 |
| Ile | Ser | Val | Leu | Tyr | Phe | Asp | Asp | Ser | Ser | Asn | Val | Ile | Leu | Lys | Lys | |
| | 405 | | | | | 410 | | | | | 415 | | | | | |
| TAC | AGA | AAC | ATG | GTG | GTC | CGG | GCC | TGT | GGC | TGC | CAC | TAGCTCCTCC | | | | 1351 |
| Tyr | Arg | Asn | Met | Val | Val | Arg | Ala | Cys | Gly | Cys | His | | | | | |
| 420 | | | | | 425 | | | | | 430 | | | | | | |

```
GAGAATTCAG ACCCTTTGGG GCCAAGTTTT TCTGGATCCT CCATTGCTCG CCTTGGCCAG    1411
GAACCAGCAG ACCAACTGCC TTTTGTGAGA CCTTCCCCTC CCTATCCCCA ACTTTAAAGG    1471
TGTGAGAGTA TTAGGAAACA TGAGCAGCAT ATGGCTTTTG ATCAGTTTTT CAGTGGCAGC    1531
ATCCAATGAA CAAGATCCTA CAAGCTGTGC AGGCAAAACC TAGCAGGAAA AAAAAACAAC    1591
GCATAAAGAA AAATGGCCGG GCCAGGTCAT GGCTGGGAA GTCTCAGCCA TGCACGGACT     1651
CGTTTCCAGA GGTAATTATG AGCGCCTACC AGCCAGGCCA CCCAGCCGTG GGAGGAAGGG    1711
GGCGTGGCAA GGGGTGGGCA CATTGGTGTC TGTGCGAAAG GAAAATTGAC CCGGAAGTTC    1771
CTGTAATAAA TGTCACAATA AACGAATGA ATGAAAAAAA AAAAAAAAA A               1822
```

( 2 ) INFORMATION FOR SEQ ID NO:17:

( i ) SEQUENCE CHARACTERISTICS:
        ( A ) LENGTH: 431 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

```
Met His Val Arg Ser Leu Arg Ala Ala Ala Pro His Ser Phe Val Ala
 1               5                  10                 15

Leu Trp Ala Pro Leu Phe Leu Leu Arg Ser Ala Leu Ala Asp Phe Ser
                20                 25                 30

Leu Asp Asn Glu Val His Ser Ser Phe Ile His Arg Arg Leu Arg Ser
             35                 40                 45

Gln Glu Arg Arg Glu Met Gln Arg Glu Ile Leu Ser Ile Leu Gly Leu
     50                 55                 60

Pro His Arg Pro Arg Pro His Leu Gln Gly Lys His Asn Ser Ala Pro
 65                 70                 75                 80

Met Phe Met Leu Asp Leu Tyr Asn Ala Met Ala Val Glu Glu Gly Gly
                85                 90                 95

Gly Pro Gly Gly Gln Gly Phe Ser Tyr Pro Tyr Lys Ala Val Phe Ser
            100                105                110

Thr Gln Gly Pro Pro Leu Ala Ser Leu Gln Asp Ser His Phe Leu Thr
        115                120                125

Asp Ala Asp Met Val Met Ser Phe Val Asn Leu Val Glu His Asp Lys
130                135                140

Glu Phe Phe His Pro Arg Tyr His His Arg Glu Phe Arg Phe Asp Leu
145                150                155                160

Ser Lys Ile Pro Glu Gly Glu Ala Val Thr Ala Ala Glu Phe Arg Ile
                165                170                175

Tyr Lys Asp Tyr Ile Arg Glu Arg Phe Asp Asn Glu Thr Phe Arg Ile
            180                185                190

Ser Val Tyr Gln Val Leu Gln Glu His Leu Gly Arg Glu Ser Asp Leu
        195                200                205

Phe Leu Leu Asp Ser Arg Thr Leu Trp Ala Ser Glu Glu Gly Trp Leu
```

|        |        |        |        |        | 210    |        |        |        |        | 215    |        |        |        |        | 220    |        |        |        |        |
|--------|--------|--------|--------|--------|--------|--------|--------|--------|--------|--------|--------|--------|--------|--------|--------|--------|--------|--------|--------|

Val Phe Asp Ile Thr Ala Thr Ser Asn His Trp Val Val Asn Pro Arg
225             230                 235             240

His Asn Leu Gly Leu Gln Leu Ser Val Glu Thr Leu Asp Gly Gln Ser
            245                 250             255

Ile Asn Pro Lys Leu Ala Gly Leu Ile Gly Arg His Gly Pro Gln Asn
        260                 265             270

Lys Gln Pro Phe Met Val Ala Phe Phe Lys Ala Thr Glu Val His Phe
        275             280              285

Arg Ser Ile Arg Ser Thr Gly Ser Lys Gln Arg Ser Gln Asn Arg Ser
    290             295             300

Lys Thr Pro Lys Asn Gln Glu Ala Leu Arg Met Ala Asn Val Ala Glu
305             310             315             320

Asn Ser Ser Ser Asp Gln Arg Gln Ala Cys Lys Lys His Glu Leu Tyr
                325             330             335

Val Ser Phe Arg Asp Leu Gly Trp Gln Asp Trp Ile Ile Ala Pro Glu
            340             345             350

Gly Tyr Ala Ala Tyr Tyr Cys Glu Gly Glu Cys Ala Phe Pro Leu Asn
        355             360             365

Ser Tyr Met Asn Ala Thr Asn His Ala Ile Val Gln Thr Leu Val His
    370             375             380

Phe Ile Asn Pro Glu Thr Val Pro Lys Pro Cys Cys Ala Pro Thr Gln
385             390             395             400

Leu Asn Ala Ile Ser Val Leu Tyr Phe Asp Asp Ser Ser Asn Val Ile
            405             410             415

Leu Lys Lys Tyr Arg Asn Met Val Val Arg Ala Cys Gly Cys His
            420             425             430

( 2 ) INFORMATION FOR SEQ ID NO:18:

( i ) SEQUENCE CHARACTERISTICS:
        ( A ) LENGTH: 1873 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 104..1393
        ( D ) OTHER INFORMATION: /product="MOP1 (CDNA)"

( x i ) SEQUENCE DESCRIPTION: SEQ ID NO:18:

```
CTGCAGCAAG TGACCTCGGG TCGTGGACCG CTGCCCTGCC CCCTCCGCTG CCACCTGGGG        60

CGGCGCGGGC CCGGTGCCCC GGATCGCGCG TAGAGCCGGC GCG ATG CAC GTG CGC        115
                                              Met His Val Arg
                                              1

TCG CTG CGC GCT GCG GCG CCA CAC AGC TTC GTG GCG CTC TGG GCG CCT        163
Ser Leu Arg Ala Ala Ala Pro His Ser Phe Val Ala Leu Trp Ala Pro
  5               10                  15                  20

CTG TTC TTG CTG CGC TCC GCC CTG GCC GAT TTC AGC CTG GAC AAC GAG        211
Leu Phe Leu Leu Arg Ser Ala Leu Ala Asp Phe Ser Leu Asp Asn Glu
            25                  30                  35

GTG CAC TCC AGC TTC ATC CAC CGG CGC CTC CGC AGC CAG GAG CGG CGG        259
Val His Ser Ser Phe Ile His Arg Arg Leu Arg Ser Gln Glu Arg Arg
        40                  45                  50

GAG ATG CAG CGG GAG ATC CTG TCC ATC TTA GGG TTG CCC CAT CGC CCG        307
Glu Met Gln Arg Glu Ile Leu Ser Ile Leu Gly Leu Pro His Arg Pro
    55                  60                  65
```

| | | | | | | | | | | | | | | | | |
|---|---|---|---|---|---|---|---|---|---|---|---|---|---|---|---|---|
| CGC | CCG | CAC | CTC | CAG | GGA | AAG | CAT | AAT | TCG | GCG | CCC | ATG | TTC | ATG | TTG | 355 |
| Arg | Pro | His | Leu | Gln | Gly | Lys | His | Asn | Ser | Ala | Pro | Met | Phe | Met | Leu | |
| | 70 | | | | 75 | | | | | 80 | | | | | | |
| GAC | CTG | TAC | AAC | GCC | ATG | GCG | GTG | GAG | GAG | AGC | GGG | CCG | GAC | GGA | CAG | 403 |
| Asp | Leu | Tyr | Asn | Ala | Met | Ala | Val | Glu | Glu | Ser | Gly | Pro | Asp | Gly | Gln | |
| 85 | | | | | 90 | | | | | 95 | | | | | 100 | |
| GGC | TTC | TCC | TAC | CCC | TAC | AAG | GCC | GTC | TTC | AGT | ACC | CAG | GGC | CCC | CCT | 451 |
| Gly | Phe | Ser | Tyr | Pro | Tyr | Lys | Ala | Val | Phe | Ser | Thr | Gln | Gly | Pro | Pro | |
| | | | | 105 | | | | | 110 | | | | | 115 | | |
| TTA | GCC | AGC | CTG | CAG | GAC | AGC | CAT | TTC | CTC | ACT | GAC | GCC | GAC | ATG | GTC | 499 |
| Leu | Ala | Ser | Leu | Gln | Asp | Ser | His | Phe | Leu | Thr | Asp | Ala | Asp | Met | Val | |
| | | | 120 | | | | | 125 | | | | | 130 | | | |
| ATG | AGC | TTC | GTC | AAC | CTA | GTG | GAA | CAT | GAC | AAA | GAA | TTC | TTC | CAC | CCT | 547 |
| Met | Ser | Phe | Val | Asn | Leu | Val | Glu | His | Asp | Lys | Glu | Phe | Phe | His | Pro | |
| | | 135 | | | | 140 | | | | | 145 | | | | | |
| CGA | TAC | CAC | CAT | CGG | GAG | TTC | CGG | TTT | GAT | CTT | TCC | AAG | ATC | CCC | GAG | 595 |
| Arg | Tyr | His | His | Arg | Glu | Phe | Arg | Phe | Asp | Leu | Ser | Lys | Ile | Pro | Glu | |
| | 150 | | | | | 155 | | | | | 160 | | | | | |
| GGC | GAA | CGG | GTG | ACC | GCA | GCC | GAA | TTC | AGG | ATC | TAT | AAG | GAC | TAC | ATC | 643 |
| Gly | Glu | Arg | Val | Thr | Ala | Ala | Glu | Phe | Arg | Ile | Tyr | Lys | Asp | Tyr | Ile | |
| 165 | | | | | 170 | | | | | 175 | | | | | 180 | |
| CGG | GAG | CGA | TTT | GAC | AAC | GAG | ACC | TTC | CAG | ATC | ACA | GTC | TAT | CAG | GTG | 691 |
| Arg | Glu | Arg | Phe | Asp | Asn | Glu | Thr | Phe | Gln | Ile | Thr | Val | Tyr | Gln | Val | |
| | | | | 185 | | | | | 190 | | | | | 195 | | |
| CTC | CAG | GAG | CAC | TCA | GGC | AGG | GAG | TCG | GAC | CTC | TTC | TTG | CTG | GAC | AGC | 739 |
| Leu | Gln | Glu | His | Ser | Gly | Arg | Glu | Ser | Asp | Leu | Phe | Leu | Leu | Asp | Ser | |
| | | | | 200 | | | | | 205 | | | | | 210 | | |
| CGC | ACC | ATC | TGG | GCT | TCT | GAG | GAG | GGC | TGG | TTG | GTG | TTT | GAT | ATC | ACA | 787 |
| Arg | Thr | Ile | Trp | Ala | Ser | Glu | Glu | Gly | Trp | Leu | Val | Phe | Asp | Ile | Thr | |
| | | 215 | | | | | 220 | | | | | 225 | | | | |
| GCC | ACC | AGC | AAC | CAC | TGG | GTG | GTC | AAC | CCT | CGG | CAC | AAC | CTG | GGC | TTA | 835 |
| Ala | Thr | Ser | Asn | His | Trp | Val | Val | Asn | Pro | Arg | His | Asn | Leu | Gly | Leu | |
| | 230 | | | | | 235 | | | | | 240 | | | | | |
| CAG | CTC | TCT | GTG | GAG | ACC | CTG | GAT | GGG | CAG | AGC | ATC | AAC | CCC | AAG | TTG | 883 |
| Gln | Leu | Ser | Val | Glu | Thr | Leu | Asp | Gly | Gln | Ser | Ile | Asn | Pro | Lys | Leu | |
| 245 | | | | | 250 | | | | | 255 | | | | | 260 | |
| GCA | GGC | CTG | ATT | GGA | CGG | CAT | GGA | CCC | CAG | AAC | AAG | CAA | CCC | TTC | ATG | 931 |
| Ala | Gly | Leu | Ile | Gly | Arg | His | Gly | Pro | Gln | Asn | Lys | Gln | Pro | Phe | Met | |
| | | | | 265 | | | | | 270 | | | | | 275 | | |
| GTG | GCC | TTC | TTC | AAG | GCC | ACG | GAA | GTC | CAT | CTC | CGT | AGT | ATC | CGG | TCC | 979 |
| Val | Ala | Phe | Phe | Lys | Ala | Thr | Glu | Val | His | Leu | Arg | Ser | Ile | Arg | Ser | |
| | | | 280 | | | | | 285 | | | | | 290 | | | |
| ACG | GGG | GGC | AAG | CAG | CGC | AGC | CAG | AAT | CGC | TCC | AAG | ACG | CCA | AAG | AAC | 1027 |
| Thr | Gly | Gly | Lys | Gln | Arg | Ser | Gln | Asn | Arg | Ser | Lys | Thr | Pro | Lys | Asn | |
| | | 295 | | | | | 300 | | | | | 305 | | | | |
| CAA | GAG | GCC | CTG | AGG | ATG | GCC | AGT | GTG | GCA | GAA | AAC | AGC | AGC | AGT | GAC | 1075 |
| Gln | Glu | Ala | Leu | Arg | Met | Ala | Ser | Val | Ala | Glu | Asn | Ser | Ser | Ser | Asp | |
| | 310 | | | | | 315 | | | | | 320 | | | | | |
| CAG | AGG | CAG | GCC | TGC | AAG | AAA | CAT | GAG | CTG | TAC | GTC | AGC | TTC | CGA | GAC | 1123 |
| Gln | Arg | Gln | Ala | Cys | Lys | Lys | His | Glu | Leu | Tyr | Val | Ser | Phe | Arg | Asp | |
| 325 | | | | | 330 | | | | | 335 | | | | | 340 | |
| CTT | GGC | TGG | CAG | GAC | TGG | ATC | ATT | GCA | CCT | GAA | GGC | TAT | GCT | GCC | TAC | 1171 |
| Leu | Gly | Trp | Gln | Asp | Trp | Ile | Ile | Ala | Pro | Glu | Gly | Tyr | Ala | Ala | Tyr | |
| | | | | 345 | | | | | 350 | | | | | 355 | | |
| TAC | TGT | GAG | GGA | GAG | TGC | GCC | TTC | CCT | CTG | AAC | TCC | TAC | ATG | AAC | GCC | 1219 |
| Tyr | Cys | Glu | Gly | Glu | Cys | Ala | Phe | Pro | Leu | Asn | Ser | Tyr | Met | Asn | Ala | |
| | | | | 360 | | | | | 365 | | | | | 370 | | |
| ACC | AAC | CAC | GCC | ATC | GTC | CAG | ACA | CTG | GTT | CAC | TTC | ATC | AAC | CCA | GAC | 1267 |
| Thr | Asn | His | Ala | Ile | Val | Gln | Thr | Leu | Val | His | Phe | Ile | Asn | Pro | Asp | |
| | | 375 | | | | | 380 | | | | | 385 | | | | |

```
ACA GTA CCC AAG CCC TGC TGT GCG CCC ACC CAG CTC AAC GCC ATC TCT       1315
Thr Val Pro Lys Pro Cys Cys Ala Pro Thr Gln Leu Asn Ala Ile Ser
    390             395                 400

GTC CTC TAC TTC GAC GAC AGC TCT AAT GTC ATC CTG AAG AAG TAC AGA       1363
Val Leu Tyr Phe Asp Asp Ser Ser Asn Val Ile Leu Lys Lys Tyr Arg
405             410                 415                 420

AAC ATG GTG GTC CGG GCC TGT GGC TGC CAC TAGCTCTTCC TGAGACCCTG         1413
Asn Met Val Val Arg Ala Cys Gly Cys His
            425             430

ACCTTTGCGG GGCCACACCT TTCCAAATCT TCGATGTCTC ACCATCTAAG TCTCTCACTG     1473

CCCACCTTGG CGAGGAGAAC AGACCAACCT CTCCTGAGCC TTCCCTCACC TCCCAACCGG     1533

AAGCATGTAA GGGTTCCAGA AACCTGAGCG TGCAGCAGCT GATGAGCGCC CTTTCCTTCT     1593

GGCACGTGAC GGACAAGATC CTACCAGCTA CCACAGCAAA CGCCTAAGAG CAGGAAAAAT     1653

GTCTGCCAGG AAAGTGTCCA GTGTCCACAT GGCCCCTGGC GCTCTGAGTC TTTGAGGAGT     1713

AATCGCAAGC CTCGTTCAGC TGCAGCAGAA GGAAGGGCTT AGCCAGGGTG GGCGCTGGCG     1773

TCTGTGTTGA AGGGAAACCA AGCAGAAGCC ACTGTAATGA TATGTCACAA TAAAACCCAT     1833

GAATGAAAAA AAAAAAAAAA AAAAAAAAAA AAAAGAATTC                           1873
```

( 2 ) INFORMATION FOR SEQ ID NO:19:

( i ) SEQUENCE CHARACTERISTICS:
    ( A ) LENGTH: 430 amino acids
    ( B ) TYPE: amino acid
    ( D ) TOPOLOGY: linear ( i i ) MOLECULE TYPE: protein ( x i ) SEQUENCE DESCRIPTION: SEQ ID NO:19:

```
Met His Val Arg Ser Leu Arg Ala Ala Ala Pro His Ser Phe Val Ala
 1               5                  10                  15

Leu Trp Ala Pro Leu Phe Leu Leu Arg Ser Ala Leu Ala Asp Phe Ser
             20                  25                  30

Leu Asp Asn Glu Val His Ser Ser Phe Ile His Arg Arg Leu Arg Ser
         35                  40                  45

Gln Glu Arg Arg Glu Met Gln Arg Glu Ile Leu Ser Ile Leu Gly Leu
     50                  55                  60

Pro His Arg Pro Arg Pro His Leu Gln Gly Lys His Asn Ser Ala Pro
 65                  70                  75                  80

Met Phe Met Leu Asp Leu Tyr Asn Ala Met Ala Val Glu Glu Ser Gly
                 85                  90                  95

Pro Asp Gly Gln Gly Phe Ser Tyr Pro Tyr Lys Ala Val Phe Ser Thr
            100                 105                 110

Gln Gly Pro Pro Leu Ala Ser Leu Gln Asp Ser His Phe Leu Thr Asp
        115                 120                 125

Ala Asp Met Val Met Ser Phe Val Asn Leu Val Glu His Asp Lys Glu
130                 135                 140

Phe Phe His Pro Arg Tyr His His Arg Glu Phe Arg Phe Asp Leu Ser
145                 150                 155                 160

Lys Ile Pro Glu Gly Glu Arg Val Thr Ala Ala Glu Phe Arg Ile Tyr
                165                 170                 175

Lys Asp Tyr Ile Arg Glu Arg Phe Asp Asn Glu Thr Phe Gln Ile Thr
            180                 185                 190

Val Tyr Gln Val Leu Gln Glu His Ser Gly Arg Glu Ser Asp Leu Phe
        195                 200                 205
```

| | | | | | | | | | | | | | | |
|---|---|---|---|---|---|---|---|---|---|---|---|---|---|---|
|Leu|Leu|Asp|Ser|Arg|Thr|Ile|Trp|Ala|Ser|Glu|Glu|Gly|Trp|Leu|Val|
| |210| | | | |215| | | |220| | | | |

| | | | | | | | | | | | | | | |
|---|---|---|---|---|---|---|---|---|---|---|---|---|---|---|
|Phe|Asp|Ile|Thr|Ala|Thr|Ser|Asn|His|Trp|Val|Val|Asn|Pro|Arg|His|
|225| | | | |230| | | | |235| | | | |240|

| | | | | | | | | | | | | | | |
|---|---|---|---|---|---|---|---|---|---|---|---|---|---|---|
|Asn|Leu|Gly|Leu|Gln|Leu|Ser|Val|Glu|Thr|Leu|Asp|Gly|Gln|Ser|Ile|
| | | | |245| | | | |250| | | | |255| |

| | | | | | | | | | | | | | | |
|---|---|---|---|---|---|---|---|---|---|---|---|---|---|---|
|Asn|Pro|Lys|Leu|Ala|Gly|Leu|Ile|Gly|Arg|His|Gly|Pro|Gln|Asn|Lys|
| | | |260| | | | |265| | | | |270| | |

| | | | | | | | | | | | | | | |
|---|---|---|---|---|---|---|---|---|---|---|---|---|---|---|
|Gln|Pro|Phe|Met|Val|Ala|Phe|Phe|Lys|Ala|Thr|Glu|Val|His|Leu|Arg|
| | |275| | | | |280| | | | |285| | | |

| | | | | | | | | | | | | | | |
|---|---|---|---|---|---|---|---|---|---|---|---|---|---|---|
|Ser|Ile|Arg|Ser|Thr|Gly|Gly|Lys|Gln|Arg|Ser|Gln|Asn|Arg|Ser|Lys|
| |290| | | | |295| | | |300| | | | | |

| | | | | | | | | | | | | | | |
|---|---|---|---|---|---|---|---|---|---|---|---|---|---|---|
|Thr|Pro|Lys|Asn|Gln|Glu|Ala|Leu|Arg|Met|Ala|Ser|Val|Ala|Glu|Asn|
|305| | | | |310| | | | |315| | | | |320|

| | | | | | | | | | | | | | | |
|---|---|---|---|---|---|---|---|---|---|---|---|---|---|---|
|Ser|Ser|Ser|Asp|Gln|Arg|Gln|Ala|Cys|Lys|Lys|His|Glu|Leu|Tyr|Val|
| | | | |325| | | | |330| | | | |335| |

| | | | | | | | | | | | | | | |
|---|---|---|---|---|---|---|---|---|---|---|---|---|---|---|
|Ser|Phe|Arg|Asp|Leu|Gly|Trp|Gln|Asp|Trp|Ile|Ile|Ala|Pro|Glu|Gly|
| | | |340| | | | |345| | | | |350| | |

| | | | | | | | | | | | | | | |
|---|---|---|---|---|---|---|---|---|---|---|---|---|---|---|
|Tyr|Ala|Ala|Tyr|Tyr|Cys|Glu|Gly|Glu|Cys|Ala|Phe|Pro|Leu|Asn|Ser|
| | |355| | | | |360| | | | |365| | | |

| | | | | | | | | | | | | | | |
|---|---|---|---|---|---|---|---|---|---|---|---|---|---|---|
|Tyr|Met|Asn|Ala|Thr|Asn|His|Ala|Ile|Val|Gln|Thr|Leu|Val|His|Phe|
| |370| | | | |375| | | | |380| | | | |

| | | | | | | | | | | | | | | |
|---|---|---|---|---|---|---|---|---|---|---|---|---|---|---|
|Ile|Asn|Pro|Asp|Thr|Val|Pro|Lys|Pro|Cys|Cys|Ala|Pro|Thr|Gln|Leu|
|385| | | | |390| | | | |395| | | | |400|

| | | | | | | | | | | | | | | |
|---|---|---|---|---|---|---|---|---|---|---|---|---|---|---|
|Asn|Ala|Ile|Ser|Val|Leu|Tyr|Phe|Asp|Asp|Ser|Ser|Asn|Val|Ile|Leu|
| | | | |405| | | | |410| | | | |415| |

| | | | | | | | | | | |
|---|---|---|---|---|---|---|---|---|---|---|---|
|Lys|Lys|Tyr|Arg|Asn|Met|Val|Val|Arg|Ala|Cys|Gly|Cys|His|
| | | |420| | | | |425| | | | |430|

(2) INFORMATION FOR SEQ ID NO:20:

(i) SEQUENCE CHARACTERISTICS:
        (A) LENGTH: 1723 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 490..1695

(xi) SEQUENCE DESCRIPTION: SEQ ID NO:20:

```
GGCGCCGGCA GAGCAGGAGT GGCTGGAGGA GCTGTGGTTG GAGCAGGAGG TGGCACGGCA      60

GGGCTGGAGG GCTCCCTATG AGTGGCGGAG ACGGCCCAGG AGGCGCTGGA GCAACAGCTC     120

CCACACCGCA CCAAGCGGTG GCTGCAGGAG CTCGCCCATC GCCCCTGCGC TGCTCGGACC     180

GCGGCCACAG CCGGACTGGC GGGTACGGCG GCGACAGAGG CATTGGCCGA GAGTCCCAGT     240

CCGCAGAGTA GCCCCGGCCT CGAGGCGGTG GCGTCCCGGT CCTCTCCGTC CAGGAGCCAG     300

GACAGGTGTC GCGCGGCGGG GCTCCAGGGA CCGCGCCTGA GGCCGGCTGC CCGCCCGTCC     360

CGCCCCGCCC CGCCGCCCGC CGCCCGCCGA GCCCAGCCTC CTTGCCGTCG GGGCGTCCCC     420

AGGCCCTGGG TCGGCCGCGG AGCCGATGCG CGCCCGCTGA GCGCCCCAGC TGAGCGCCCC     480

CGGCCTGCC ATG ACC GCG CTC CCC GGC CCG CTC TGG CTC CTG GGC CTG         528
           Met Thr Ala Leu Pro Gly Pro Leu Trp Leu Leu Gly Leu
             1               5                  10

GCG CTA TGC GCG CTG GGC GGG GGC GGC CCC GGC CTG CGA CCC CCG CCC         576
```

-continued

```
                    Ala Leu Cys Ala Leu Gly Gly Gly Pro Gly Leu Arg Pro Pro Pro
                         15                  20                  25

GGC TGT CCC CAG CGA CGT CTG GGC GCG CGC GAG CGC CGG GAC GTG CAG             624
Gly Cys Pro Gln Arg Arg Leu Gly Ala Arg Glu Arg Arg Asp Val Gln
 30                  35                  40                      45

CGC GAG ATC CTG GCG GTG CTC GGG CTG CCT GGG CGG CCC CGG CCC CGC             672
Arg Glu Ile Leu Ala Val Leu Gly Leu Pro Gly Arg Pro Arg Pro Arg
                     50                  55                  60

GCG CCA CCC GCC GCC TCC CGG CTG CCC GCG TCC GCG CCG CTC TTC ATG             720
Ala Pro Pro Ala Ala Ser Arg Leu Pro Ala Ser Ala Pro Leu Phe Met
             65                  70                  75

CTG GAC CTG TAC CAC GCC ATG GCC GGC GAC GAC GAC GAG GAC GGC GCG             768
Leu Asp Leu Tyr His Ala Met Ala Gly Asp Asp Asp Glu Asp Gly Ala
         80                  85                  90

CCC GCG GAG CGG CGC CTG GGC CGC GCC GAC CTG GTC ATG AGC TTC GTT             816
Pro Ala Glu Arg Arg Leu Gly Arg Ala Asp Leu Val Met Ser Phe Val
     95                  100                 105

AAC ATG GTG GAG CGA GAC CGT GCC CTG GGC CAC CAG GAG CCC CAT TGG             864
Asn Met Val Glu Arg Asp Arg Ala Leu Gly His Gln Glu Pro His Trp
110                  115                 120                 125

AAG GAG TTC CGC TTT GAC CTG ACC CAG ATC CCG GCT GGG GAG GCG GTC             912
Lys Glu Phe Arg Phe Asp Leu Thr Gln Ile Pro Ala Gly Glu Ala Val
                 130                 135                 140

ACA GCT GCG GAG TTC CGG ATT TAC AAG GTG CCC AGC ATC CAC CTG CTC             960
Thr Ala Ala Glu Phe Arg Ile Tyr Lys Val Pro Ser Ile His Leu Leu
             145                 150                 155

AAC AGG ACC CTC CAC GTC AGC ATG TTC CAG GTG GTC CAG GAG CAG TCC            1008
Asn Arg Thr Leu His Val Ser Met Phe Gln Val Val Gln Glu Gln Ser
         160                 165                 170

AAC AGG GAG TCT GAC TTG TTC TTT TTG GAT CTT CAG ACG CTC CGA GCT            1056
Asn Arg Glu Ser Asp Leu Phe Phe Leu Asp Leu Gln Thr Leu Arg Ala
     175                 180                 185

GGA GAC GAG GGC TGG CTG GTG CTG GAT GTC ACA GCA GCC AGT GAC TGC            1104
Gly Asp Glu Gly Trp Leu Val Leu Asp Val Thr Ala Ala Ser Asp Cys
190                 195                 200                 205

TGG TTG CTG AAG CGT CAC AAG GAC CTG GGA CTC CGC CTC TAT GTG GAG            1152
Trp Leu Leu Lys Arg His Lys Asp Leu Gly Leu Arg Leu Tyr Val Glu
                 210                 215                 220

ACT GAG GAC GGG CAC AGC GTG GAT CCT GGC CTG GCC GGC CTG CTG GGT            1200
Thr Glu Asp Gly His Ser Val Asp Pro Gly Leu Ala Gly Leu Leu Gly
             225                 230                 235

CAA CGG GCC CCA CGC TCC CAA CAG CCT TTC GTG GTC ACT TTC TTC AGG            1248
Gln Arg Ala Pro Arg Ser Gln Gln Pro Phe Val Val Thr Phe Phe Arg
         240                 245                 250

GCC AGT CCG AGT CCC ATC CGC ACC CCT CGG GCA GTG AGG CCA CTG AGG            1296
Ala Ser Pro Ser Pro Ile Arg Thr Pro Arg Ala Val Arg Pro Leu Arg
     255                 260                 265

AGG AGG CAG CCG AAG AAA AGC AAC GAG CTG CCG CAG GCC AAC CGA CTC            1344
Arg Arg Gln Pro Lys Lys Ser Asn Glu Leu Pro Gln Ala Asn Arg Leu
270                 275                 280                 285

CCA GGG ATC TTT GAT GAC GTC CAC GGC TCC CAC GGC CGG CAG GTC TGC            1392
Pro Gly Ile Phe Asp Asp Val His Gly Ser His Gly Arg Gln Val Cys
                 290                 295                 300

CGT CGG CAC GAG CTC TAC GTC AGC TTC CAG GAC CTC GGC TGG CTG GAC            1440
Arg Arg His Glu Leu Tyr Val Ser Phe Gln Asp Leu Gly Trp Leu Asp
             305                 310                 315

TGG GTC ATC GCT CCC CAA GGC TAC TCG GCC TAT TAC TGT GAG GGG GAG            1488
Trp Val Ile Ala Pro Gln Gly Tyr Ser Ala Tyr Tyr Cys Glu Gly Glu
         320                 325                 330

TGC TCC TTC CCA CTG GAC TCC TGC ATG AAT GCC ACC AAC CAC GCC ATC            1536
```

|  |  |  |  |  |  |  |  |  |  |  |  |  |  |  |  |
|---|---|---|---|---|---|---|---|---|---|---|---|---|---|---|---|
| Cys | Ser | Phe | Pro | Leu | Asp | Ser | Cys | Met | Asn | Ala | Thr | Asn | His | Ala | Ile |
|  | 335 |  |  |  | 340 |  |  |  |  | 345 |  |  |  |  |  |

| CTG | CAG | TCC | CTG | GTG | CAC | CTG | ATG | AAG | CCA | AAC | GCA | GTC | CCC | AAG | GCG | 1584 |
|---|---|---|---|---|---|---|---|---|---|---|---|---|---|---|---|---|
| Leu | Gln | Ser | Leu | Val | His | Leu | Met | Lys | Pro | Asn | Ala | Val | Pro | Lys | Ala |  |
| 350 |  |  |  |  | 355 |  |  |  | 360 |  |  |  |  |  | 365 |  |

| TGC | TGT | GCA | CCC | ACC | AAG | CTG | AGC | GCC | ACC | TCT | GTG | CTC | TAC | TAT | GAC | 1632 |
|---|---|---|---|---|---|---|---|---|---|---|---|---|---|---|---|---|
| Cys | Cys | Ala | Pro | Thr | Lys | Leu | Ser | Ala | Thr | Ser | Val | Leu | Tyr | Tyr | Asp |  |
|  |  |  |  | 370 |  |  |  |  | 375 |  |  |  |  |  | 380 |  |

| AGC | AGC | AAC | AAC | GTC | ATC | CTG | CGC | AAA | CAC | CGC | AAC | ATG | GTG | GTC | AAG | 1680 |
|---|---|---|---|---|---|---|---|---|---|---|---|---|---|---|---|---|
| Ser | Ser | Asn | Asn | Val | Ile | Leu | Arg | Lys | His | Arg | Asn | Met | Val | Val | Lys |  |
|  |  |  |  | 385 |  |  |  |  | 390 |  |  |  |  | 395 |  |  |

| GCC | TGC | GGC | TGC | CAC | TGAGTCAGCC | CGCCCAGCCC | TACTGCAG | 1723 |
|---|---|---|---|---|---|---|---|---|
| Ala | Cys | Gly | Cys | His |  |  |  |  |
|  |  |  | 400 |  |  |  |  |  |

( 2 ) INFORMATION FOR SEQ ID NO:21:

( i ) SEQUENCE CHARACTERISTICS:
( A ) LENGTH: 402 amino acids
( B ) TYPE: amino acid
( D ) TOPOLOGY: linear ( i i ) MOLECULE TYPE: protein ( x i ) SEQUENCE DESCRIPTION: SEQ ID NO:21:

| Met | Thr | Ala | Leu | Pro | Gly | Pro | Leu | Trp | Leu | Leu | Gly | Leu | Ala | Leu | Cys |
|---|---|---|---|---|---|---|---|---|---|---|---|---|---|---|---|
| 1 |  |  |  | 5 |  |  |  |  | 10 |  |  |  |  | 15 |  |
| Ala | Leu | Gly | Gly | Gly | Gly | Pro | Gly | Leu | Arg | Pro | Pro | Pro | Gly | Cys | Pro |
|  |  |  | 20 |  |  |  |  | 25 |  |  |  | 30 |  |  |  |
| Gln | Arg | Arg | Leu | Gly | Ala | Arg | Glu | Arg | Arg | Asp | Val | Gln | Arg | Glu | Ile |
|  |  | 35 |  |  |  |  | 40 |  |  |  |  | 45 |  |  |  |
| Leu | Ala | Val | Leu | Gly | Leu | Pro | Gly | Arg | Pro | Arg | Pro | Arg | Ala | Pro | Pro |
|  | 50 |  |  |  |  | 55 |  |  |  |  | 60 |  |  |  |  |
| Ala | Ala | Ser | Arg | Leu | Pro | Ala | Ser | Ala | Pro | Leu | Phe | Met | Leu | Asp | Leu |
| 65 |  |  |  |  | 70 |  |  |  |  | 75 |  |  |  |  | 80 |
| Tyr | His | Ala | Met | Ala | Gly | Asp | Asp | Asp | Glu | Asp | Gly | Ala | Pro | Ala | Glu |
|  |  |  |  | 85 |  |  |  |  | 90 |  |  |  |  | 95 |  |
| Arg | Arg | Leu | Gly | Arg | Ala | Asp | Leu | Val | Met | Ser | Phe | Val | Asn | Met | Val |
|  |  |  | 100 |  |  |  |  | 105 |  |  |  |  | 110 |  |  |
| Glu | Arg | Asp | Arg | Ala | Leu | Gly | His | Gln | Glu | Pro | His | Trp | Lys | Glu | Phe |
|  |  | 115 |  |  |  |  | 120 |  |  |  |  | 125 |  |  |  |
| Arg | Phe | Asp | Leu | Thr | Gln | Ile | Pro | Ala | Gly | Glu | Ala | Val | Thr | Ala | Ala |
| 130 |  |  |  |  | 135 |  |  |  |  | 140 |  |  |  |  |  |
| Glu | Phe | Arg | Ile | Tyr | Lys | Val | Pro | Ser | Ile | His | Leu | Leu | Asn | Arg | Thr |
| 145 |  |  |  |  | 150 |  |  |  |  | 155 |  |  |  |  | 160 |
| Leu | His | Val | Ser | Met | Phe | Gln | Val | Val | Gln | Glu | Gln | Ser | Asn | Arg | Glu |
|  |  |  |  | 165 |  |  |  |  | 170 |  |  |  |  | 175 |  |
| Ser | Asp | Leu | Phe | Phe | Leu | Asp | Leu | Gln | Thr | Leu | Arg | Ala | Gly | Asp | Glu |
|  |  |  | 180 |  |  |  |  | 185 |  |  |  |  | 190 |  |  |
| Gly | Trp | Leu | Val | Leu | Asp | Val | Thr | Ala | Ala | Ser | Asp | Cys | Trp | Leu | Leu |
|  |  | 195 |  |  |  |  | 200 |  |  |  |  | 205 |  |  |  |
| Lys | Arg | His | Lys | Asp | Leu | Gly | Leu | Arg | Leu | Tyr | Val | Glu | Thr | Glu | Asp |
| 210 |  |  |  |  | 215 |  |  |  |  | 220 |  |  |  |  |  |
| Gly | His | Ser | Val | Asp | Pro | Gly | Leu | Ala | Gly | Leu | Leu | Gly | Gln | Arg | Ala |
| 225 |  |  |  |  | 230 |  |  |  |  | 235 |  |  |  |  | 240 |
| Pro | Arg | Ser | Gln | Gln | Pro | Phe | Val | Val | Thr | Phe | Phe | Arg | Ala | Ser | Pro |
|  |  |  |  | 245 |  |  |  |  | 250 |  |  |  |  | 255 |  |
| Ser | Pro | Ile | Arg | Thr | Pro | Arg | Ala | Val | Arg | Pro | Leu | Arg | Arg | Arg | Gln |

|  |  |  | 260 |  |  |  | 265 |  |  |  | 270 |  |  |
|---|---|---|---|---|---|---|---|---|---|---|---|---|---|

Pro Lys Lys Ser Asn Glu Leu Pro Gln Ala Asn Arg Leu Pro Gly Ile
        275             280                 285

Phe Asp Asp Val His Gly Ser His Gly Arg Gln Val Cys Arg Arg His
    290             295                 300

Glu Leu Tyr Val Ser Phe Gln Asp Leu Gly Trp Leu Asp Trp Val Ile
305                 310             315                     320

Ala Pro Gln Gly Tyr Ser Ala Tyr Tyr Cys Glu Gly Glu Cys Ser Phe
            325                 330                 335

Pro Leu Asp Ser Cys Met Asn Ala Thr Asn His Ala Ile Leu Gln Ser
        340             345                 350

Leu Val His Leu Met Lys Pro Asn Ala Val Pro Lys Ala Cys Cys Ala
        355             360                 365

Pro Thr Lys Leu Ser Ala Thr Ser Val Leu Tyr Tyr Asp Ser Ser Asn
    370             375                 380

Asn Val Ile Leu Arg Lys His Arg Asn Met Val Val Lys Ala Cys Gly
385             390                 395                 400

Cys His ( 2 ) INFORMATION FOR SEQ ID NO:22:

( i ) SEQUENCE CHARACTERISTICS:
        ( A ) LENGTH: 1926 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 93..1289
        ( D ) OTHER INFORMATION: /product="MOP2 CDNA"

( x i ) SEQUENCE DESCRIPTION: SEQ ID NO:22:

GCCAGGCACA GGTGCGCCGT CTGGTCCTCC CCGTCTGGCG TCAGCCGAGC CCGACCAGCT    60

ACCAGTGGAT GCGCGCCGGC TGAAAGTCCG AG ATG GCT ATG CGT CCC GGG CCA    113
                                          Met Ala Met Arg Pro Gly Pro
                                                1                    5

CTC TGG CTA TTG GGC CTT GCT CTG TGC GCG CTG GGA GGC GGC CAC GGT    161
Leu Trp Leu Leu Gly Leu Ala Leu Cys Ala Leu Gly Gly Gly His Gly
       10                   15                   20

CCG CGT CCC CCG CAC ACC TGT CCC CAG CGT CGC CTG GGA GCG CGC GAG    209
Pro Arg Pro Pro His Thr Cys Pro Gln Arg Arg Leu Gly Ala Arg Glu
   25                  30                     35

CGC CGC GAC ATG CAG CGT GAA ATC CTG GCG GTG CTC GGG CTA CCG GGA    257
Arg Arg Asp Met Gln Arg Glu Ile Leu Ala Val Leu Gly Leu Pro Gly
40                  45                    50                   55

CGG CCC CGA CCC CGT GCA CAA CCC GCG GCT GCC CGG CAG CCA GCG TCC    305
Arg Pro Arg Pro Arg Ala Gln Pro Ala Ala Ala Arg Gln Pro Ala Ser
               60                     65                   70

GCG CCC CTC TTC ATG TTG GAC CTA TAC CAC GCC ATG ACC GAT GAC GAC    353
Ala Pro Leu Phe Met Leu Asp Leu Tyr His Ala Met Thr Asp Asp Asp
          75                   80                   85

GAC GGC GGG CCA CCA CAG GCT CAC TTA GGC CGT GCC GAC CTG GTC ATG    401
Asp Gly Gly Pro Pro Gln Ala His Leu Gly Arg Ala Asp Leu Val Met
          90                   95                 100

AGC TTC GTC AAC ATG GTG GAA CGC GAC CGT ACC CTG GGC TAC CAG GAG    449
Ser Phe Val Asn Met Val Glu Arg Asp Arg Thr Leu Gly Tyr Gln Glu
   105                  110                     115

| | | | | | | | | | | | | | | | | |
|---|---|---|---|---|---|---|---|---|---|---|---|---|---|---|---|---|
| CCA | CAC | TGG | AAG | GAA | TTC | CAC | TTT | GAC | CTA | ACC | CAG | ATC | CCT | GCT | GGG | 497 |
| Pro | His | Trp | Lys | Glu | Phe | His | Phe | Asp | Leu | Thr | Gln | Ile | Pro | Ala | Gly | |
| 120 | | | | 125 | | | | 130 | | | | | | | 135 | |
| GAG | GCT | GTC | ACA | GCT | GCT | GAG | TTC | CGG | ATC | TAC | AAA | GAA | CCC | AGC | ACC | 545 |
| Glu | Ala | Val | Thr | Ala | Ala | Glu | Phe | Arg | Ile | Tyr | Lys | Glu | Pro | Ser | Thr | |
| | | | | 140 | | | | | 145 | | | | | 150 | | |
| CAC | CCG | CTC | AAC | ACA | ACC | CTC | CAC | ATC | AGC | ATG | TTC | GAA | GTG | GTC | CAA | 593 |
| His | Pro | Leu | Asn | Thr | Thr | Leu | His | Ile | Ser | Met | Phe | Glu | Val | Val | Gln | |
| | | | 155 | | | | | 160 | | | | | 165 | | | |
| GAG | CAC | TCC | AAC | AGG | GAG | TCT | GAC | TTG | TTC | TTT | TTG | GAT | CTT | CAG | ACG | 641 |
| Glu | His | Ser | Asn | Arg | Glu | Ser | Asp | Leu | Phe | Phe | Leu | Asp | Leu | Gln | Thr | |
| | | 170 | | | | | 175 | | | | | 180 | | | | |
| CTC | CGA | TCT | GGG | GAC | GAG | GGC | TGG | CTG | GTG | CTG | GAC | ATC | ACA | GCA | GCC | 689 |
| Leu | Arg | Ser | Gly | Asp | Glu | Gly | Trp | Leu | Val | Leu | Asp | Ile | Thr | Ala | Ala | |
| | 185 | | | | | 190 | | | | | 195 | | | | | |
| AGT | GAC | CGA | TGG | CTG | CTG | AAC | CAT | CAC | AAG | GAC | CTG | GGA | CTC | CGC | CTC | 737 |
| Ser | Asp | Arg | Trp | Leu | Leu | Asn | His | His | Lys | Asp | Leu | Gly | Leu | Arg | Leu | |
| 200 | | | | 205 | | | | | 210 | | | | | | 215 | |
| TAT | GTG | GAA | ACC | GCG | GAT | GGG | CAC | AGC | ATG | GAT | CCT | GGC | CTG | GCT | GGT | 785 |
| Tyr | Val | Glu | Thr | Ala | Asp | Gly | His | Ser | Met | Asp | Pro | Gly | Leu | Ala | Gly | |
| | | | | 220 | | | | | 225 | | | | | 230 | | |
| CTG | CTT | GGA | CGA | CAA | GCA | CCA | CGC | TCC | AGA | CAG | CCT | TTC | ATG | GTA | ACC | 833 |
| Leu | Leu | Gly | Arg | Gln | Ala | Pro | Arg | Ser | Arg | Gln | Pro | Phe | Met | Val | Thr | |
| | | | 235 | | | | | 240 | | | | | 245 | | | |
| TTC | TTC | AGG | GCC | AGC | CAG | AGT | CCT | GTG | CGG | GCC | CCT | CGG | GCA | GCG | AGA | 881 |
| Phe | Phe | Arg | Ala | Ser | Gln | Ser | Pro | Val | Arg | Ala | Pro | Arg | Ala | Ala | Arg | |
| | | 250 | | | | | 255 | | | | | 260 | | | | |
| CCA | CTG | AAG | AGG | AGG | CAG | CCA | AAG | AAA | ACG | AAC | GAG | CTT | CCG | CAC | CCC | 929 |
| Pro | Leu | Lys | Arg | Arg | Gln | Pro | Lys | Lys | Thr | Asn | Glu | Leu | Pro | His | Pro | |
| | 265 | | | | | 270 | | | | | 275 | | | | | |
| AAC | AAA | CTC | CCA | GGG | ATC | TTT | GAT | GAT | GGC | CAC | GGT | TCC | CGC | GGC | AGA | 977 |
| Asn | Lys | Leu | Pro | Gly | Ile | Phe | Asp | Asp | Gly | His | Gly | Ser | Arg | Gly | Arg | |
| 280 | | | | | 285 | | | | | 290 | | | | | 295 | |
| GAG | GTT | TGC | CGC | AGG | CAT | GAG | CTC | TAC | GTC | AGC | TTC | CGT | GAC | CTT | GGC | 1025 |
| Glu | Val | Cys | Arg | Arg | His | Glu | Leu | Tyr | Val | Ser | Phe | Arg | Asp | Leu | Gly | |
| | | | | 300 | | | | | 305 | | | | | 310 | | |
| TGG | CTG | GAC | TGG | GTC | ATC | GCC | CCC | CAG | GGC | TAC | TCT | GCC | TAT | TAC | TGT | 1073 |
| Trp | Leu | Asp | Trp | Val | Ile | Ala | Pro | Gln | Gly | Tyr | Ser | Ala | Tyr | Tyr | Cys | |
| | | | 315 | | | | | 320 | | | | | 325 | | | |
| GAG | GGG | GAG | TGT | GCT | TTC | CCA | CTG | GAC | TCC | TGT | ATG | AAC | GCC | ACC | AAC | 1121 |
| Glu | Gly | Glu | Cys | Ala | Phe | Pro | Leu | Asp | Ser | Cys | Met | Asn | Ala | Thr | Asn | |
| | | 330 | | | | | 335 | | | | | 340 | | | | |
| CAT | GCC | ATC | TTG | CAG | TCT | CTG | GTG | CAC | CTG | ATG | AAG | CCA | GAT | GTT | GTC | 1169 |
| His | Ala | Ile | Leu | Gln | Ser | Leu | Val | His | Leu | Met | Lys | Pro | Asp | Val | Val | |
| | 345 | | | | | 350 | | | | | 355 | | | | | |
| CCC | AAG | GCA | TGC | TGT | GCA | CCC | ACC | AAA | CTG | AGT | GCC | ACC | TCT | GTG | CTG | 1217 |
| Pro | Lys | Ala | Cys | Cys | Ala | Pro | Thr | Lys | Leu | Ser | Ala | Thr | Ser | Val | Leu | |
| 360 | | | | | 365 | | | | | 370 | | | | | 375 | |
| TAC | TAT | GAC | AGC | AGC | AAC | AAT | GTC | ATC | CTG | CGT | AAA | CAC | CGT | AAC | ATG | 1265 |
| Tyr | Tyr | Asp | Ser | Ser | Asn | Asn | Val | Ile | Leu | Arg | Lys | His | Arg | Asn | Met | |
| | | | | 380 | | | | | 385 | | | | | 390 | | |
| GTG | GTC | AAG | GCC | TGT | GGC | TGC | CAC | TGAGGCCCCG | | | CCCAGCATCC | | TGCTTCTACT | | | 1319 |
| Val | Val | Lys | Ala | Cys | Gly | Cys | His | | | | | | | | | |
| | | | 395 | | | | | | | | | | | | | |

| | | | | |
|---|---|---|---|---|
| ACCTTACCAT | CTGGCCGGGC | CCCTCTCCAG | AGGCAGAAAC | CCTTCTATGT | TATCATAGCT | 1379 |
| CAGACAGGGG | CAATGGGAGG | CCCTTCACTT | CCCCTGGCCA | CTTCCTGCTA | AAATTCTGGT | 1439 |
| CTTTCCCAGT | TCCTCTGTCC | TTCATGGGGT | TTCGGGGCTA | TCACCCCGCC | CTCTCCATCC | 1499 |
| TCCTACCCCA | AGCATAGACT | GAATGCACAC | AGCATCCCAG | AGCTATGCTA | ACTGAGAGGT | 1559 |

-continued

```
CTGGGGTCAG  CACTGAAGGC  CCACATGAGG  AAGACTGATC  CTTGGCCATC  CTCAGCCCAC      1619
AATGGCAAAT  TCTGGATGGT  CTAAGAAGGC  CGTGGAATTC  TAAACTAGAT  GATCTGGGCT      1679
CTCTGCACCA  TTCATTGTGG  CAGTTGGGAC  ATTTTAGGT   ATAACAGACA  CATACACTTA      1739
GATCAATGCA  TCGCTGTACT  CCTTGAAATC  AGAGCTAGCT  TGTTAGAAAA  AGAATCAGAG      1799
CCAGGTATAG  CGGTGCATGT  CATTAATCCC  AGCGCTAAAG  AGACAGAGAC  AGGAGAATCT      1859
CTGTGAGTTC  AAGGCCACAT  AGAAAGAGCC  TGTCTCGGGA  GCAGGAAAAA  AAAAAAAAAC      1919
GGAATTC                                                                    1926
```

( 2 ) INFORMATION FOR SEQ ID NO:23:

( i ) SEQUENCE CHARACTERISTICS:
        ( A ) LENGTH: 399 amino acids
        ( B ) TYPE: amino acid
        ( D ) TOPOLOGY: linear ( i i ) MOLECULE TYPE: protein ( x i ) SEQUENCE DESCRIPTION: SEQ ID NO:23:

```
Met  Ala  Met  Arg  Pro  Gly  Pro  Leu  Trp  Leu  Gly  Leu  Ala  Leu  Cys
 1              5                    10                       15
Ala  Leu  Gly  Gly  Gly  His  Gly  Pro  Arg  Pro  Pro  His  Thr  Cys  Pro  Gln
              20                   25                       30
Arg  Arg  Leu  Gly  Ala  Arg  Glu  Arg  Arg  Asp  Met  Gln  Arg  Glu  Ile  Leu
              35                   40                       45
Ala  Val  Leu  Gly  Leu  Pro  Gly  Arg  Pro  Arg  Pro  Arg  Ala  Gln  Pro  Ala
         50                        55                   60
Ala  Ala  Arg  Gln  Pro  Ala  Ser  Ala  Pro  Leu  Phe  Met  Leu  Asp  Leu  Tyr
 65                        70                   75                       80
His  Ala  Met  Thr  Asp  Asp  Asp  Gly  Gly  Pro  Pro  Gln  Ala  His  Leu
                   85                   90                   95
Gly  Arg  Ala  Asp  Leu  Val  Met  Ser  Phe  Val  Asn  Met  Val  Glu  Arg  Asp
                  100                  105                      110
Arg  Thr  Leu  Gly  Tyr  Gln  Glu  Pro  His  Trp  Lys  Glu  Phe  His  Phe  Asp
              115                  120                      125
Leu  Thr  Gln  Ile  Pro  Ala  Gly  Glu  Ala  Val  Thr  Ala  Ala  Glu  Phe  Arg
         130                       135                  140
Ile  Tyr  Lys  Glu  Pro  Ser  Thr  His  Pro  Leu  Asn  Thr  Thr  Leu  His  Ile
145                       150                  155                       160
Ser  Met  Phe  Glu  Val  Val  Gln  Glu  His  Ser  Asn  Arg  Glu  Ser  Asp  Leu
                  165                  170                      175
Phe  Phe  Leu  Asp  Leu  Gln  Thr  Leu  Arg  Ser  Gly  Asp  Glu  Gly  Trp  Leu
              180                  185                      190
Val  Leu  Asp  Ile  Thr  Ala  Ala  Ser  Asp  Arg  Trp  Leu  Leu  Asn  His  His
         195                       200                  205
Lys  Asp  Leu  Gly  Leu  Arg  Leu  Tyr  Val  Glu  Thr  Ala  Asp  Gly  His  Ser
210                       215                  220
Met  Asp  Pro  Gly  Leu  Ala  Gly  Leu  Leu  Gly  Arg  Gln  Ala  Pro  Arg  Ser
225                       230                  235                       240
Arg  Gln  Pro  Phe  Met  Val  Thr  Phe  Phe  Arg  Ala  Ser  Gln  Ser  Pro  Val
                       245                  250                      255
Arg  Ala  Pro  Arg  Ala  Ala  Arg  Pro  Leu  Lys  Arg  Arg  Gln  Pro  Lys  Lys
                  260                       265                  270
Thr  Asn  Glu  Leu  Pro  His  Pro  Asn  Lys  Leu  Pro  Gly  Ile  Phe  Asp  Asp
              275                  280                      285
```

```
Gly His Gly Ser Arg Gly Arg Glu Val Cys Arg Arg His Glu Leu Tyr
    290                 295                 300

Val Ser Phe Arg Asp Leu Gly Trp Leu Asp Trp Val Ile Ala Pro Gln
305                 310                 315                 320

Gly Tyr Ser Ala Tyr Tyr Cys Glu Gly Glu Cys Ala Phe Pro Leu Asp
                325                 330                 335

Ser Cys Met Asn Ala Thr Asn His Ala Ile Leu Gln Ser Leu Val His
            340                 345                 350

Leu Met Lys Pro Asp Val Val Pro Lys Ala Cys Cys Ala Pro Thr Lys
        355                 360                 365

Leu Ser Ala Thr Ser Val Leu Tyr Tyr Asp Ser Ser Asn Asn Val Ile
370                 375                 380

Leu Arg Lys His Arg Asn Met Val Val Lys Ala Cys Gly Cys His
385                 390                 395
```

( 2 ) INFORMATION FOR SEQ ID NO:24:

( i ) SEQUENCE CHARACTERISTICS:
        ( A ) LENGTH: 1368 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1365

( x i ) SEQUENCE DESCRIPTION: SEQ ID NO:24:

```
ATG TCG GGA CTG CGA AAC ACC TCG GAG GCC GTT GCA GTG CTC GCC TCC    48
Met Ser Gly Leu Arg Asn Thr Ser Glu Ala Val Ala Val Leu Ala Ser
1               5                   10                  15

CTG GGA CTC GGA ATG GTT CTC CTC ATG TTC GTG GCG ACC ACG CCG CCG    96
Leu Gly Leu Gly Met Val Leu Leu Met Phe Val Ala Thr Thr Pro Pro
            20                  25                  30

GCC GTT GAG GCC ACC CAG TCG GGG ATT TAC ATA GAC AAC GGC AAG GAC   144
Ala Val Glu Ala Thr Gln Ser Gly Ile Tyr Ile Asp Asn Gly Lys Asp
        35                  40                  45

CAG ACG ATC ATG CAC AGA GTG CTG AGC GAG GAC GAC AAG CTG GAC GTC   192
Gln Thr Ile Met His Arg Val Leu Ser Glu Asp Asp Lys Leu Asp Val
    50                  55                  60

TCG TAC GAG ATC CTC GAG TTC CTG GGC ATC GCC GAA CGG CCG ACG CAC   240
Ser Tyr Glu Ile Leu Glu Phe Leu Gly Ile Ala Glu Arg Pro Thr His
65                  70                  75                  80

CTG AGC AGC CAC CAG TTG TCG CTG AGG AAG TCG GCT CCC AAG TTC CTG   288
Leu Ser Ser His Gln Leu Ser Leu Arg Lys Ser Ala Pro Lys Phe Leu
            85                  90                  95

CTG GAC GTC TAC CAC CGC ATC ACG GCG GAG GAG GGT CTC AGC GAT CAG   336
Leu Asp Val Tyr His Arg Ile Thr Ala Glu Glu Gly Leu Ser Asp Gln
        100                 105                 110

GAT GAG GAC GAC GAC TAC GAA CGC GGC CAT CGG TCC AGG AGG AGC GCC   384
Asp Glu Asp Asp Asp Tyr Glu Arg Gly His Arg Ser Arg Arg Ser Ala
    115                 120                 125

GAC CTC GAG GAG GAT GAG GGC GAG CAG CAG AAG AAC TTC ATC ACC GAC   432
Asp Leu Glu Glu Asp Glu Gly Glu Gln Gln Lys Asn Phe Ile Thr Asp
130                 135                 140

CTG GAC AAG CGG GCC ATC GAC GAG AGC GAC ATC ATC ATG ACC TTC CTG   480
Leu Asp Lys Arg Ala Ile Asp Glu Ser Asp Ile Ile Met Thr Phe Leu
145                 150                 155                 160

AAC AAG CGC CAC CAC AAT GTG GAC GAA CTG CGT CAC GAG CAC GGC CGT   528
Asn Lys Arg His His Asn Val Asp Glu Leu Arg His Glu His Gly Arg
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 165 |     |     |     |     | 170 |     |     |     |     |     | 175 |     |     |      |
| CGC | CTG | TGG | TTC | GAC | GTC | TCC | AAC | GTG | CCC | AAC | GAC | AAC | TAC | CTG | GTG | 576  |
| Arg | Leu | Trp | Phe | Asp | Val | Ser | Asn | Val | Pro | Asn | Asp | Asn | Tyr | Leu | Val |      |
|     |     | 180 |     |     |     |     | 185 |     |     |     |     |     | 190 |     |     |      |
| ATG | GCC | GAG | CTG | CGC | ATC | TAT | CAG | AAC | GCC | AAC | GAG | GGC | AAG | TGG | CTG | 624  |
| Met | Ala | Glu | Leu | Arg | Ile | Tyr | Gln | Asn | Ala | Asn | Glu | Gly | Lys | Trp | Leu |      |
|     |     | 195 |     |     |     |     | 200 |     |     |     |     |     | 205 |     |     |      |
| ACC | GCC | AAC | AGG | GAG | TTC | ACC | ATC | ACG | GTA | TAC | GCC | ATT | GGC | ACC | GGC | 672  |
| Thr | Ala | Asn | Arg | Glu | Phe | Thr | Ile | Thr | Val | Tyr | Ala | Ile | Gly | Thr | Gly |      |
|     |     | 210 |     |     |     |     | 215 |     |     |     |     |     | 220 |     |     |      |
| ACG | CTG | GGC | CAG | CAC | ACC | ATG | GAG | CCG | CTG | TCC | TCG | GTG | AAC | ACC | ACC | 720  |
| Thr | Leu | Gly | Gln | His | Thr | Met | Glu | Pro | Leu | Ser | Ser | Val | Asn | Thr | Thr |      |
|     |     | 225 |     |     |     |     | 230 |     |     |     |     |     | 235 |     | 240 |      |
| GGG | GAC | TAC | GTG | GGC | TGG | TTG | GAG | CTC | AAC | GTG | ACC | GAG | GGC | CTG | CAC | 768  |
| Gly | Asp | Tyr | Val | Gly | Trp | Leu | Glu | Leu | Asn | Val | Thr | Glu | Gly | Leu | His |      |
|     |     |     |     | 245 |     |     |     |     | 250 |     |     |     |     | 255 |     |      |
| GAG | TGG | CTG | GTC | AAG | TCG | AAG | GAC | AAT | CAT | GGC | ATC | TAC | ATT | GGA | GCA | 816  |
| Glu | Trp | Leu | Val | Lys | Ser | Lys | Asp | Asn | His | Gly | Ile | Tyr | Ile | Gly | Ala |      |
|     |     |     |     | 260 |     |     |     |     | 265 |     |     |     |     | 270 |     |      |
| CAC | GCT | GTC | AAC | CGA | CCC | GAC | CGC | GAG | GTG | AAG | CTG | GAC | GAC | ATT | GGA | 864  |
| His | Ala | Val | Asn | Arg | Pro | Asp | Arg | Glu | Val | Lys | Leu | Asp | Asp | Ile | Gly |      |
|     |     | 275 |     |     |     |     | 280 |     |     |     |     |     | 285 |     |     |      |
| CTG | ATC | CAC | CGC | AAG | GTG | GAC | GAC | GAG | TTC | CAG | CCC | TTC | ATG | ATC | GGC | 912  |
| Leu | Ile | His | Arg | Lys | Val | Asp | Asp | Glu | Phe | Gln | Pro | Phe | Met | Ile | Gly |      |
|     |     | 290 |     |     |     |     | 295 |     |     |     |     |     | 300 |     |     |      |
| TTC | TTC | CGC | GGA | CCG | GAG | CTG | ATC | AAG | GCG | ACG | GCC | CAC | AGC | AGC | CAC | 960  |
| Phe | Phe | Arg | Gly | Pro | Glu | Leu | Ile | Lys | Ala | Thr | Ala | His | Ser | Ser | His |      |
| 305 |     |     |     |     |     | 310 |     |     |     |     | 315 |     |     |     | 320 |      |
| CAC | AGG | AGC | AAG | CGA | AGC | GCC | AGC | CAT | CCA | CGC | AAG | CGC | AAG | AAG | TCG | 1008 |
| His | Arg | Ser | Lys | Arg | Ser | Ala | Ser | His | Pro | Arg | Lys | Arg | Lys | Lys | Ser |      |
|     |     |     |     | 325 |     |     |     |     | 330 |     |     |     |     | 335 |     |      |
| GTG | TCG | CCC | AAC | AAC | GTG | CCG | CTG | CTG | GAA | CCG | ATG | GAG | AGC | ACG | CGC | 1056 |
| Val | Ser | Pro | Asn | Asn | Val | Pro | Leu | Leu | Glu | Pro | Met | Glu | Ser | Thr | Arg |      |
|     |     |     | 340 |     |     |     |     | 345 |     |     |     |     | 350 |     |     |      |
| AGC | TGC | CAG | ATG | CAG | ACC | CTG | TAC | ATA | GAC | TTC | AAG | GAT | CTG | GGC | TGG | 1104 |
| Ser | Cys | Gln | Met | Gln | Thr | Leu | Tyr | Ile | Asp | Phe | Lys | Asp | Leu | Gly | Trp |      |
|     |     | 355 |     |     |     |     | 360 |     |     |     |     |     | 365 |     |     |      |
| CAT | GAC | TGG | ATC | ATC | GCA | CCA | GAG | GGC | TAT | GGC | GCC | TTC | TAC | TGC | AGC | 1152 |
| His | Asp | Trp | Ile | Ile | Ala | Pro | Glu | Gly | Tyr | Gly | Ala | Phe | Tyr | Cys | Ser |      |
|     |     | 370 |     |     |     |     | 375 |     |     |     |     |     | 380 |     |     |      |
| GGC | GAG | TGC | AAT | TTC | CCG | CTC | AAT | GCG | CAC | ATG | AAC | GCC | ACG | AAC | CAT | 1200 |
| Gly | Glu | Cys | Asn | Phe | Pro | Leu | Asn | Ala | His | Met | Asn | Ala | Thr | Asn | His |      |
| 385 |     |     |     |     | 390 |     |     |     |     | 395 |     |     |     |     | 400 |      |
| GCG | ATC | GTC | CAG | ACC | CTG | GTC | CAC | CTG | CTG | GAG | CCC | AAG | AAG | GTG | CCC | 1248 |
| Ala | Ile | Val | Gln | Thr | Leu | Val | His | Leu | Leu | Glu | Pro | Lys | Lys | Val | Pro |      |
|     |     |     |     | 405 |     |     |     |     | 410 |     |     |     |     | 415 |     |      |
| AAG | CCC | TGC | TGC | GCT | CCG | ACC | AGG | CTG | GGA | GCA | CTA | CCC | GTT | CTG | TAC | 1296 |
| Lys | Pro | Cys | Cys | Ala | Pro | Thr | Arg | Leu | Gly | Ala | Leu | Pro | Val | Leu | Tyr |      |
|     |     |     | 420 |     |     |     |     | 425 |     |     |     |     | 430 |     |     |      |
| CAC | CTG | AAC | GAC | GAG | AAT | GTG | AAC | CTG | AAA | AAG | TAT | AGA | AAC | ATG | ATT | 1344 |
| His | Leu | Asn | Asp | Glu | Asn | Val | Asn | Leu | Lys | Lys | Tyr | Arg | Asn | Met | Ile |      |
|     |     | 435 |     |     |     |     | 440 |     |     |     |     |     | 445 |     |     |      |
| GTG | AAA | TCC | TGC | GGG | TGC | CAT | TGA |     |     |     |     |     |     |     |     | 1368 |
| Val | Lys | Ser | Cys | Gly | Cys | His |     |     |     |     |     |     |     |     |     |      |
| 450 |     |     |     |     | 455 |     |     |     |     |     |     |     |     |     |     |      |

( 2 ) INFORMATION FOR SEQ ID NO:25:

( i ) SEQUENCE CHARACTERISTICS:
        ( A ) LENGTH: 455 amino acids
        ( B ) TYPE: amino acid ( D ) TOPOLOGY: linear ( i i ) MOLECULE TYPE: protein ( x i ) SEQUENCE DESCRIPTION: SEQ ID NO:25:

```
Met Ser Gly Leu Arg Asn Thr Ser Glu Ala Val Ala Val Leu Ala Ser
 1               5                  10                  15
Leu Gly Leu Gly Met Val Leu Leu Met Phe Val Ala Thr Thr Pro Pro
                20                  25                  30
Ala Val Glu Ala Thr Gln Ser Gly Ile Tyr Ile Asp Asn Gly Lys Asp
            35                  40                  45
Gln Thr Ile Met His Arg Val Leu Ser Glu Asp Lys Leu Asp Val
        50                  55                  60
Ser Tyr Glu Ile Leu Glu Phe Leu Gly Ile Ala Glu Arg Pro Thr His
 65                  70                  75                  80
Leu Ser Ser His Gln Leu Ser Leu Arg Lys Ser Ala Pro Lys Phe Leu
                85                  90                  95
Leu Asp Val Tyr His Arg Ile Thr Ala Glu Glu Gly Leu Ser Asp Gln
                100                 105                 110
Asp Glu Asp Asp Asp Tyr Glu Arg Gly His Arg Ser Arg Arg Ser Ala
            115                 120                 125
Asp Leu Glu Glu Asp Glu Gly Glu Gln Gln Lys Asn Phe Ile Thr Asp
    130                 135                 140
Leu Asp Lys Arg Ala Ile Asp Glu Ser Asp Ile Ile Met Thr Phe Leu
145                 150                 155                 160
Asn Lys Arg His His Asn Val Asp Glu Leu Arg His Glu His Gly Arg
                165                 170                 175
Arg Leu Trp Phe Asp Val Ser Asn Val Pro Asn Asp Asn Tyr Leu Val
            180                 185                 190
Met Ala Glu Leu Arg Ile Tyr Gln Asn Ala Asn Glu Gly Lys Trp Leu
    195                 200                 205
Thr Ala Asn Arg Glu Phe Thr Ile Thr Val Tyr Ala Ile Gly Thr Gly
210                 215                 220
Thr Leu Gly Gln His Thr Met Glu Pro Leu Ser Ser Val Asn Thr Thr
225                 230                 235                 240
Gly Asp Tyr Val Gly Trp Leu Glu Leu Asn Val Thr Glu Gly Leu His
                245                 250                 255
Glu Trp Leu Val Lys Ser Lys Asp Asn His Gly Ile Tyr Ile Gly Ala
            260                 265                 270
His Ala Val Asn Arg Pro Asp Arg Glu Val Lys Leu Asp Asp Ile Gly
    275                 280                 285
Leu Ile His Arg Lys Val Asp Asp Glu Phe Gln Pro Phe Met Ile Gly
    290                 295                 300
Phe Phe Arg Gly Pro Glu Leu Ile Lys Ala Thr Ala His Ser Ser His
305                 310                 315                 320
His Arg Ser Lys Arg Ser Ala Ser His Pro Arg Lys Arg Lys Lys Ser
                325                 330                 335
Val Ser Pro Asn Asn Val Pro Leu Leu Glu Pro Met Glu Ser Thr Arg
            340                 345                 350
Ser Cys Gln Met Gln Thr Leu Tyr Ile Asp Phe Lys Asp Leu Gly Trp
        355                 360                 365
His Asp Trp Ile Ile Ala Pro Glu Gly Tyr Gly Ala Phe Tyr Cys Ser
    370                 375                 380
Gly Glu Cys Asn Phe Pro Leu Asn Ala His Met Asn Ala Thr Asn His
385                 390                 395                 400
```

Ala Ile Val Gln Thr Leu Val His Leu Leu Glu Pro Lys Lys Val Pro
            405                     410                     415

Lys Pro Cys Cys Ala Pro Thr Arg Leu Gly Ala Leu Pro Val Leu Tyr
            420                     425                     430

His Leu Asn Asp Glu Asn Val Asn Leu Lys Lys Tyr Arg Asn Met Ile
            435                     440                     445

Val Lys Ser Cys Gly Cys His
450                     455

(2) INFORMATION FOR SEQ ID NO:26:

(i) SEQUENCE CHARACTERISTICS:
      (A) LENGTH: 104 amino acids
      (B) TYPE: amino acid
      (C) STRANDEDNESS: single
      (D) TOPOLOGY: linear (ii) MOLECULE TYPE: protein (ix) FEATURE:
      (A) NAME/KEY: Protein
      (B) LOCATION: 1..104
      (D) OTHER INFORMATION: /label=BMP3

(xi) SEQUENCE DESCRIPTION: SEQ ID NO:26:

Cys Ala Arg Arg Tyr Leu Lys Val Asp Phe Ala Asp Ile Gly Trp Ser
1               5                   10                  15

Glu Trp Ile Ile Ser Pro Lys Ser Phe Asp Ala Tyr Tyr Cys Ser Gly
            20                  25                  30

Ala Cys Gln Phe Pro Met Pro Lys Ser Leu Lys Pro Ser Asn His Ala
            35                  40                  45

Thr Ile Gln Ser Ile Val Ala Arg Ala Val Gly Val Val Pro Gly Ile
            50                  55                  60

Pro Glu Pro Cys Cys Val Pro Glu Lys Met Ser Ser Leu Ser Ile Leu
65                      70                  75                  80

Phe Phe Asp Glu Asn Lys Asn Val Val Leu Lys Val Tyr Pro Asn Met
                    85                  90                  95

Thr Val Glu Ser Cys Ala Cys Arg
            100

(2) INFORMATION FOR SEQ ID NO:27:

(i) SEQUENCE CHARACTERISTICS:
      (A) LENGTH: 102 amino acids
      (B) TYPE: amino acid
      (C) STRANDEDNESS: single
      (D) TOPOLOGY: linear (ii) MOLECULE TYPE: protein (ix) FEATURE:
      (A) NAME/KEY: Protein
      (B) LOCATION: 1..102
      (D) OTHER INFORMATION: /label=BMP5

(xi) SEQUENCE DESCRIPTION: SEQ ID NO:27:

Cys Lys Lys His Glu Leu Tyr Val Ser Phe Arg Asp Leu Gly Trp Gln
1               5                   10                  15

Asp Trp Ile Ile Ala Pro Glu Gly Tyr Ala Ala Phe Tyr Cys Asp Gly
            20                  25                  30

Glu Cys Ser Phe Pro Leu Asn Ala His Met Asn Ala Thr Asn His Ala
            35                  40                  45

Ile Val Gln Thr Leu Val His Leu Met Phe Pro Asp His Val Pro Lys

```
                 50                      55                      60
    Pro  Cys  Cys  Ala  Pro  Thr  Lys  Leu  Asn  Ala  Ile  Ser  Val  Leu  Tyr  Phe
    65                  70                       75                           80

Asp  Asp  Ser  Ser  Asn  Val  Ile  Leu  Lys  Lys  Tyr  Arg  Asn  Met  Val  Val
                        85                       90                      95

Arg  Ser  Cys  Gly  Cys  His
                   100
```

( 2 ) INFORMATION FOR SEQ ID NO:28:

( i ) SEQUENCE CHARACTERISTICS:
        ( A ) LENGTH: 102 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..102
        ( D ) OTHER INFORMATION: /label=BMP6

( x i ) SEQUENCE DESCRIPTION: SEQ ID NO:28:

```
    Cys  Arg  Lys  His  Glu  Leu  Tyr  Val  Ser  Phe  Gln  Asp  Leu  Gly  Trp  Gln
    1              5                        10                          15

Asp  Trp  Ile  Ile  Ala  Pro  Lys  Gly  Tyr  Ala  Ala  Asn  Tyr  Cys  Asp  Gly
                   20                       25                      30

Glu  Cys  Ser  Phe  Pro  Leu  Asn  Ala  His  Met  Asn  Ala  Thr  Asn  His  Ala
              35                       40                      45

Ile  Val  Gln  Thr  Leu  Val  His  Leu  Met  Asn  Pro  Glu  Tyr  Val  Pro  Lys
         50                       55                      60

Pro  Cys  Cys  Ala  Pro  Thr  Lys  Leu  Asn  Ala  Ile  Ser  Val  Leu  Tyr  Phe
    65                  70                       75                           80

Asp  Asp  Asn  Ser  Asn  Val  Ile  Leu  Lys  Lys  Tyr  Arg  Trp  Met  Val  Val
                        85                       90                      95

Arg  Ala  Cys  Gly  Cys  His
                   100
```

( 2 ) INFORMATION FOR SEQ ID NO:29:

( i ) SEQUENCE CHARACTERISTICS:
        ( A ) LENGTH: 102 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..102
        ( D ) OTHER INFORMATION: /label=OPX
            / note= "WHEREIN XAA AT EACH POS'N IS INDEPENDENTLY
              SELECTED FROM THE RESIDUES OCCURING AT THE CORRESPONDING
              POS'N IN THE C-TERMINAL SEQUENCE OF MOUSE OR HUMAN OP1
              OR OP2 (SEQ. ID NOS. 5,6,7&8 OR 16,18, 20&22"

( x i ) SEQUENCE DESCRIPTION: SEQ ID NO:29:

```
    Cys  Xaa  Xaa  His  Glu  Leu  Tyr  Val  Xaa  Phe  Xaa  Asp  Leu  Gly  Trp  Xaa
    1              5                        10                          15

Asp  Trp  Xaa  Ile  Ala  Pro  Xaa  Gly  Tyr  Xaa  Ala  Tyr  Tyr  Cys  Glu  Gly
                   20                       25                      30

Glu  Cys  Xaa  Phe  Pro  Leu  Xaa  Ser  Xaa  Met  Asn  Ala  Thr  Asn  His  Ala
              35                       40                      45
```

```
Ile  Xaa  Gln  Xaa  Leu  Val  His  Xaa  Xaa  Xaa  Pro  Xaa  Xaa  Val  Pro  Lys
     50                  55                      60

Xaa  Cys  Cys  Ala  Pro  Thr  Xaa  Leu  Xaa  Ala  Xaa  Ser  Val  Leu  Tyr  Xaa
65                       70                  75                           80

Asp  Xaa  Ser  Xaa  Asn  Val  Xaa  Leu  Xaa  Lys  Xaa  Arg  Asn  Met  Val  Val
               85                       90                           95

Xaa  Ala  Cys  Gly  Cys  His
               100
```

( 2 ) INFORMATION FOR SEQ ID NO:30:

( i ) SEQUENCE CHARACTERISTICS:
        ( A ) LENGTH: 97 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..97
        ( D ) OTHER INFORMATION: /label=GENERIC-SEQ-5
        / note= "WHEREIN EACH XAA IS INDEPENDENTLY SELECTED FROM A
        GROUP OF ONE OR MORE SPECIFIED AMINO ACIDS AS DEFINED IN
        THE SPECIFICATION"

( x i ) SEQUENCE DESCRIPTION: SEQ ID NO:30:

```
Leu  Xaa  Xaa  Xaa  Phe  Xaa  Xaa  Xaa  Gly  Trp  Xaa  Xaa  Trp  Xaa  Xaa  Xaa
1                   5                        10                      15

Pro  Xaa  Xaa  Xaa  Xaa  Ala  Xaa  Tyr  Cys  Xaa  Gly  Xaa  Cys  Xaa  Xaa  Pro
               20                       25                      30

Xaa  Xaa  Xaa  Xaa  Xaa  Xaa  Xaa  Xaa  Asn  His  Ala  Xaa  Xaa  Xaa  Xaa  Xaa
               35                       40                      45

Xaa  Xaa  Xaa  Xaa  Xaa  Xaa  Xaa  Xaa  Xaa  Xaa  Xaa  Xaa  Cys  Cys  Xaa  Pro
     50                       55                      60

Xaa  Xaa  Xaa  Xaa  Xaa  Xaa  Xaa  Xaa  Leu  Xaa  Xaa  Xaa  Xaa  Xaa  Xaa  Xaa
65                       70                       75                         80

Val  Xaa  Leu  Xaa  Xaa  Xaa  Xaa  Xaa  Met  Xaa  Val  Xaa  Xaa  Cys  Xaa  Cys
               85                       90                      95

Xaa
```

( 2 ) INFORMATION FOR SEQ ID NO:31:

( i ) SEQUENCE CHARACTERISTICS:
        ( A ) LENGTH: 102 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..102
        ( D ) OTHER INFORMATION: /label=GENERIC-SEQ-6
        / note= "WHEREIN EACH XAA IS INDEPENDENTLY SELECTED FROM
        A GROUP OF ONE OR MORE SPECIFIED AMINO ACIDS AS
        DEFINED IN THE SPECIFICATION"

( x i ) SEQUENCE DESCRIPTION: SEQ ID NO:31:

```
Cys  Xaa  Xaa  Xaa  Xaa  Leu  Xaa  Xaa  Xaa  Phe  Xaa  Xaa  Xaa  Gly  Trp  Xaa
1                   5                        10                      15

Xaa  Trp  Xaa  Xaa  Xaa  Pro  Xaa  Xaa  Xaa  Xaa  Ala  Xaa  Tyr  Cys  Xaa  Gly
               20                       25                      30
```

|     |     |     |     |     |     |     |     |     |     |     |     |     |     |
|-----|-----|-----|-----|-----|-----|-----|-----|-----|-----|-----|-----|-----|-----|
| Xaa | Cys | Xaa | Xaa | Pro | Xaa | Xaa | Xaa | Xaa | Xaa | Xaa | Xaa | Asn | His | Ala |
|     |     | 35  |     |     |     |     | 40  |     |     |     | 45  |     |     |     |
| Xaa | Xaa | Xaa | Xaa | Xaa | Xaa | Xaa | Xaa | Xaa | Xaa | Xaa | Xaa | Xaa | Xaa |
|     |     | 50  |     |     |     |     | 55  |     |     |     | 60  |     |     |
| Xaa | Cys | Cys | Xaa | Pro | Xaa | Xaa | Xaa | Xaa | Xaa | Xaa | Xaa | Leu | Xaa | Xaa |
| 65  |     |     |     | 70  |     |     |     |     | 75  |     |     |     |     | 80  |
| Xaa | Xaa | Xaa | Xaa | Xaa | Val | Xaa | Leu | Xaa | Xaa | Xaa | Xaa | Xaa | Met | Xaa | Val |
|     |     |     |     | 85  |     |     |     |     | 90  |     |     |     |     | 95  |
| Xaa | Xaa | Cys | Xaa | Cys | Xaa |
|     |     |     | 100 |     |     |

( 2 ) INFORMATION FOR SEQ ID NO:32:

( i ) SEQUENCE CHARACTERISTICS:
        ( A ) LENGTH: 1247 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 84..1199
        ( D ) OTHER INFORMATION: /product="GDF-1"

( x i ) SEQUENCE DESCRIPTION: SEQ ID NO:32:

```
GGGGACACCG GCCCCGCCCT CAGCCCACTG GTCCCGGGCC GCCGCGGACC CTGCGCACTC           60

TCTGGTCATC GCCTGGGAGG AAG ATG CCA CCG CCG CAG CAA GGT CCC TGC             110
                         Met Pro Pro Pro Gln Gln Gly Pro Cys
                          1                   5

GGC CAC CAC CTC CTC CTC CTC CTG GCC CTG CTG CTG CCC TCG CTG CCC           158
Gly His His Leu Leu Leu Leu Leu Ala Leu Leu Leu Pro Ser Leu Pro
 10              15                  20                  25

CTG ACC CGC GCC CCC GTG CCC CCA GGC CCA GCC GCC GCC CTC CTC CAG           206
Leu Thr Arg Ala Pro Val Pro Pro Gly Pro Ala Ala Ala Leu Leu Gln
             30                  35                  40

GCT CTA GGA CTG CGC GAT GAG CCC CAG GGT GCC CCC AGG CTC CGG CCG           254
Ala Leu Gly Leu Arg Asp Glu Pro Gln Gly Ala Pro Arg Leu Arg Pro
             45                  50                  55

GTT CCC CCG GTC ATG TGG CGC CTG TTT CGA CGC CGG GAC CCC CAG GAG           302
Val Pro Pro Val Met Trp Arg Leu Phe Arg Arg Arg Asp Pro Gln Glu
             60                  65                  70

ACC AGG TCT GGC TCG CGG CGG ACG TCC CCA GGG GTC ACC CTG CAA CCG           350
Thr Arg Ser Gly Ser Arg Arg Thr Ser Pro Gly Val Thr Leu Gln Pro
 75                  80                  85

TGC CAC GTG GAG GAG CTG GGG GTC GCC GGA AAC ATC GTG CGC CAC ATC           398
Cys His Val Glu Glu Leu Gly Val Ala Gly Asn Ile Val Arg His Ile
 90                  95                  100                 105

CCG GAC CGC GGT GCG CCC ACC CGG GCC TCG GAG CCT GTC TCG GCC GCG           446
Pro Asp Arg Gly Ala Pro Thr Arg Ala Ser Glu Pro Val Ser Ala Ala
                 110                 115                 120

GGG CAT TGC CCT GAG TGG ACA GTC GTC TTC GAC CTG TCG GCT GTG GAA           494
Gly His Cys Pro Glu Trp Thr Val Val Phe Asp Leu Ser Ala Val Glu
                 125                 130                 135

CCC GCT GAG CGC CCG AGC CGG GCC CGC CTG GAG CTG CGT TTC GCG GCG           542
Pro Ala Glu Arg Pro Ser Arg Ala Arg Leu Glu Leu Arg Phe Ala Ala
                 140                 145                 150

GCG GCG GCG GCA GCC CCG GAG GGC GGC TGG GAG CTG AGC GTG GCG CAA           590
Ala Ala Ala Ala Ala Pro Glu Gly Gly Trp Glu Leu Ser Val Ala Gln
 155                 160                 165
```

| | | | | | | | | | | | | | | | | |
|---|---|---|---|---|---|---|---|---|---|---|---|---|---|---|---|---|
| GCG | GGC | CAG | GGC | GCG | GGC | GCG | GAC | CCC | GGG | CCG | GTG | CTG | CTC | CGC | CAG | 638 |
| Ala 170 | Gly | Gln | Gly | Ala 175 | Gly | Ala | Asp | Pro | Gly | Pro 180 | Val | Leu | Leu | Arg | Gln 185 | |
| TTG | GTG | CCC | GCC | CTG | GGG | CCG | CCA | GTG | CGC | GCG | GAG | CTG | CTG | GGC | GCC | 686 |
| Leu | Val | Pro | Ala | Leu 190 | Gly | Pro | Pro | Val | Arg 195 | Ala | Glu | Leu | Leu | Gly 200 | Ala | |
| GCT | TGG | GCT | CGC | AAC | GCC | TCA | TGG | CCG | CGC | AGC | CTC | CGC | CTG | GCG | CTG | 734 |
| Ala | Trp | Ala | Arg 205 | Asn | Ala | Ser | Trp | Pro 210 | Arg | Ser | Leu | Arg | Leu 215 | Ala | Leu | |
| GCG | CTA | CGC | CCC | CGG | GCC | CCT | GCC | GCC | TGC | GCG | CGC | CTG | GCC | GAG | GCC | 782 |
| Ala | Leu | Arg 220 | Pro | Arg | Ala | Pro | Ala 225 | Ala | Cys | Ala | Arg | Leu 230 | Ala | Glu | Ala | |
| TCG | CTG | CTG | CTG | GTG | ACC | CTC | GAC | CCG | CGC | CTG | TGC | CAC | CCC | CTG | GCC | 830 |
| Ser | Leu 235 | Leu | Leu | Val | Thr | Leu 240 | Asp | Pro | Arg | Leu | Cys 245 | His | Pro | Leu | Ala | |
| CGG | CCG | CGG | CGC | GAC | GCC | GAA | CCC | GTG | TTG | GGC | GGC | GGC | CCC | GGG | GGC | 878 |
| Arg 250 | Pro | Arg | Arg | Asp | Ala 255 | Glu | Pro | Val | Leu | Gly 260 | Gly | Gly | Pro | Gly | Gly 265 | |
| GCT | TGT | CGC | GCG | CGG | CGG | CTG | TAC | GTG | AGC | TTC | CGC | GAG | GTG | GGC | TGG | 926 |
| Ala | Cys | Arg | Ala | Arg 270 | Arg | Leu | Tyr | Val | Ser 275 | Phe | Arg | Glu | Val | Gly 280 | Trp | |
| CAC | CGC | TGG | GTC | ATC | GCG | CCG | CGC | GGC | TTC | CTG | GCC | AAC | TAC | TGC | CAG | 974 |
| His | Arg | Trp 285 | Val | Ile | Ala | Pro | Arg 290 | Gly | Phe | Leu | Ala | Asn 295 | Tyr | Cys | Gln | |
| GGT | CAG | TGC | GCG | CTG | CCC | GTC | GCG | CTG | TCG | GGG | TCC | GGG | GGG | CCG | CCG | 1022 |
| Gly | Gln | Cys 300 | Ala | Leu | Pro | Val | Ala 305 | Leu | Ser | Gly | Ser | Gly 310 | Gly | Pro | Pro | |
| GCG | CTC | AAC | CAC | GCT | GTG | CTG | CGC | GCG | CTC | ATG | CAC | GCG | GCC | GCC | CCG | 1070 |
| Ala | Leu | Asn 315 | His | Ala | Val | Leu 320 | Arg | Ala | Leu | Met | His 325 | Ala | Ala | Ala | Pro | |
| GGA | GCC | GCC | GAC | CTG | CCC | TGC | TGC | GTG | CCC | GCG | CGC | CTG | TCG | CCC | ATC | 1118 |
| Gly 330 | Ala | Ala | Asp | Leu | Pro 335 | Cys | Cys | Val | Pro | Ala 340 | Arg | Leu | Ser | Pro | Ile 345 | |
| TCC | GTG | CTC | TTC | TTT | GAC | AAC | AGC | GAC | AAC | GTG | GTG | CTG | CGG | CAG | TAT | 1166 |
| Ser | Val | Leu | Phe | Phe 350 | Asp | Asn | Ser | Asp | Asn 355 | Val | Val | Leu | Arg | Gln 360 | Tyr | |
| GAG | GAC | ATG | GTG | GTG | GAC | GAG | TGC | GGC | TGC | CGC | TAACCCGGGG | CGGGCAGGGA | | | | 1219 |
| Glu | Asp | Met | Val 365 | Val | Asp | Glu | Cys | Gly 370 | Cys | Arg | | | | | | |

CCCGGGCCCA ACAATAAATG CCGCGTGG    1247

( 2 ) INFORMATION FOR SEQ ID NO:33:

( i ) SEQUENCE CHARACTERISTICS:
  ( A ) LENGTH: 372 amino acids
  ( B ) TYPE: amino acid
  ( D ) TOPOLOGY: linear ( i i ) MOLECULE TYPE: protein ( x i ) SEQUENCE DESCRIPTION: SEQ ID NO:33:

| | | | | | | | | | | | | | | |
|---|---|---|---|---|---|---|---|---|---|---|---|---|---|---|
| Met 1 | Pro | Pro | Pro | Gln 5 | Gln | Gly | Pro | Cys | Gly 10 | His | His | Leu | Leu | Leu 15 | Leu |
| Leu | Ala | Leu | Leu 20 | Leu | Pro | Ser | Leu | Pro 25 | Leu | Thr | Arg | Ala | Pro 30 | Val | Pro |
| Pro | Gly | Pro 35 | Ala | Ala | Ala | Leu | Leu 40 | Gln | Ala | Leu | Gly | Leu 45 | Arg | Asp | Glu |
| Pro | Gln 50 | Gly | Ala | Pro | Arg | Leu 55 | Arg | Pro | Val | Pro | Pro 60 | Val | Met | Trp | Arg |
| Leu 65 | Phe | Arg | Arg | Arg | Asp 70 | Pro | Gln | Glu | Thr | Arg 75 | Ser | Gly | Ser | Arg | Arg 80 |

```
Thr  Ser  Pro  Gly  Val  Thr  Leu  Gln  Pro  Cys  His  Val  Glu  Glu  Leu  Gly
                    85                       90                      95

Val  Ala  Gly  Asn  Ile  Val  Arg  His  Ile  Pro  Asp  Arg  Gly  Ala  Pro  Thr
                    100                      105                     110

Arg  Ala  Ser  Glu  Pro  Val  Ser  Ala  Ala  Gly  His  Cys  Pro  Glu  Trp  Thr
               115                 120                      125

Val  Val  Phe  Asp  Leu  Ser  Ala  Val  Glu  Pro  Ala  Glu  Arg  Pro  Ser  Arg
     130                           135                 140

Ala  Arg  Leu  Glu  Leu  Arg  Phe  Ala  Ala  Ala  Ala  Ala  Ala  Ala  Pro  Glu
145                      150                      155                      160

Gly  Gly  Trp  Glu  Leu  Ser  Val  Ala  Gln  Ala  Gly  Gln  Gly  Ala  Gly  Ala
                    165                 170                           175

Asp  Pro  Gly  Pro  Val  Leu  Leu  Arg  Gln  Leu  Val  Pro  Ala  Leu  Gly  Pro
               180                 185                           190

Pro  Val  Arg  Ala  Glu  Leu  Leu  Gly  Ala  Ala  Trp  Ala  Arg  Asn  Ala  Ser
          195                 200                      205

Trp  Pro  Arg  Ser  Leu  Arg  Leu  Ala  Leu  Ala  Leu  Arg  Pro  Arg  Ala  Pro
     210                      215                 220

Ala  Ala  Cys  Ala  Arg  Leu  Ala  Glu  Ala  Ser  Leu  Leu  Leu  Val  Thr  Leu
225                      230                 235                           240

Asp  Pro  Arg  Leu  Cys  His  Pro  Leu  Ala  Arg  Pro  Arg  Arg  Asp  Ala  Glu
               245                      250                      255

Pro  Val  Leu  Gly  Gly  Gly  Pro  Gly  Gly  Ala  Cys  Arg  Ala  Arg  Arg  Leu
          260                 265                      270

Tyr  Val  Ser  Phe  Arg  Glu  Val  Gly  Trp  His  Arg  Trp  Val  Ile  Ala  Pro
          275                 280                      285

Arg  Gly  Phe  Leu  Ala  Asn  Tyr  Cys  Gln  Gly  Gln  Cys  Ala  Leu  Pro  Val
     290                 295                      300

Ala  Leu  Ser  Gly  Ser  Gly  Gly  Pro  Pro  Ala  Leu  Asn  His  Ala  Val  Leu
305                      310                      315                      320

Arg  Ala  Leu  Met  His  Ala  Ala  Ala  Pro  Gly  Ala  Ala  Asp  Leu  Pro  Cys
               325                      330                      335

Cys  Val  Pro  Ala  Arg  Leu  Ser  Pro  Ile  Ser  Val  Leu  Phe  Phe  Asp  Asn
               340                 345                      350

Ser  Asp  Asn  Val  Val  Leu  Arg  Gln  Tyr  Glu  Asp  Met  Val  Val  Asp  Glu
          355                 360                      365

Cys  Gly  Cys  Arg
          370
```